US012097258B2

(12) United States Patent
Klein et al.

(10) Patent No.: US 12,097,258 B2
(45) Date of Patent: Sep. 24, 2024

(54) VACCINE ADJUVANT

(71) Applicant: Wisconsin Alumni Research Foundation, Madison, WI (US)

(72) Inventors: Bruce Steven Klein, Madison, WI (US); Huafeng Wang, San Diego, CA (US); Marcel Wuethrich, Madison, WI (US); Tristan Theodore Brandhorst, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 61 days.

(21) Appl. No.: 17/186,366

(22) Filed: Feb. 26, 2021

(65) Prior Publication Data

US 2021/0205445 A1 Jul. 8, 2021

Related U.S. Application Data

(63) Continuation of application No. 15/787,021, filed on Oct. 18, 2017, now abandoned.

(60) Provisional application No. 62/411,281, filed on Oct. 21, 2016.

(51) Int. Cl.
*A61K 39/39* (2006.01)
*A61K 39/00* (2006.01)

(52) U.S. Cl.
CPC .......... *A61K 39/39* (2013.01); *A61K 39/0002* (2013.01); *A61K 2039/55516* (2013.01); *A61K 2039/55566* (2013.01); *A61K 2039/57* (2013.01)

(58) Field of Classification Search
CPC .............. C07K 14/4701; C07K 14/705; C07K 14/7051; C07K 14/70535; C07K 14/70546; C07K 14/7056; C07K 14/70578; C07K 14/70596; C07K 14/7156; C07K 14/7158; C07K 14/723; C07K 2319/00; C07K 2319/02; C07K 2319/03; C12N 7/00; C12N 2710/16234; A61K 2039/53
See application file for complete search history.

(56) References Cited

U.S. PATENT DOCUMENTS

| | | | | |
|---|---|---|---|---|
| 2006/0009419 | A1 | 1/2006 | Ross | |
| 2014/0271720 | A1 | 9/2014 | Klein et al. | |
| 2015/0252080 | A1* | 9/2015 | Stone | C07K 14/70535 435/235.1 |
| 2015/0301044 | A1 | 10/2015 | Klein et al. | |

OTHER PUBLICATIONS

WANG, et al.,(J.ofImmunol.2014;192:1107-1119,prepublishedonlineJa. 3,2014). (Year: 2014).*
Antibodies: A Laboratory Manual, Cold Spring Harbor Laboratory Press, Cold Spring Harbor, N.Y., (1988), 2014 update.
(Continued)

*Primary Examiner* — Jana A Hines
(74) *Attorney, Agent, or Firm* — Quarles & Brady, LLP

(57) ABSTRACT

A Dectin-2 ligand vaccine adjuvant and a method of making and using the Dectin-2 ligand vaccine adjuvant in a vaccine to immunize a patient are disclosed. Also discloses is a vaccine composition comprising a Bl-Eng2 antigen and methods of using the vaccine composition to immunize a subject against a fungal infection.

7 Claims, 26 Drawing Sheets

Specification includes a Sequence Listing.

(56) References Cited

OTHER PUBLICATIONS

Brown GD, Denning DW, Gow NA, Levitz SM, Netea MG, et al. (2012) Hidden killers: human fungal infections. Sci Transl Med 4: 165rv113.
Carrion Sde J, Leal SM, Jr., Ghannoum MA, Aimanianda V, Latge JP, et al. (2013) The RodA hydrophobin on Aspergillus fumigatus spores masks dectin-1- and dectin-2-dependent responses and enhances fungal survival in vivo. J Immunol 191: 2581-2588.
Geijtenbeek TB, Gringhuis SI (2009) Signalling through C-type lectin receptors: shaping immune responses. Nat Rev Immunol 9: 465-479.
Gopal, R. et al. "Unexpected Role for IL-17 in Protective Immunity against Hypervirulent Mycobacterium tuberculosis HN878 Infection." PLoS Pathog., 10.5 (2014): e1004099.
Gringhuis SI, den Dunnen J, Litjens M, van der Vlist M, Wevers B, et al. (2009) Dectin-1 directs T helper cell differentiation by controlling noncanonical NF-kappaB activation through Raf-1 and Syk. Nat Immunol 10: 203-213.
Gringhuis SI, Wevers BA, Kaptein TM, van Capel TM, Theelen B, et al. (2011) Selective C-Rel activation via Malt1 controls antifungal T(H)-17 immunity by dectin-1 and dectin-2. PLoS Pathog 7: e1001259.
Hartl L, Gastebois A, Aimanianda V, Latge JP (2011) Characterization of the GPI-anchored endo beta-1,3-glucanase Eng2 of Aspergillus fumigatus. Fungal Genet Biol 48: 185-191.
Ifrim DC, Bain JM, Reid DM, Oosting M, Verschueren I, et al. (2014) Role of Dectin-2 for host defense against systemic infection with Candida glabrata. Infect Immun 82: 1064-1073.
Ishikawa, et al., (Cell Host & Microbe. vol 13, Issue 4, Apr. 2013. pp. 477-488) (Year: 2013).
Ishikawa T, Itoh F, Yoshida S, Saijo S, Matsuzawa T, et al. (2013) Identification of Distinct Ligands for the C-type Lectin Receptors Mincle and Dectin-2 in the Pathogenic Fungus Malassezia. Cell Host Microbe 13: 477-488.
Jhingran A, Mar KB, Kumasaka DK, Knoblaugh SE, Ngo LY, et al. (2012) Tracing conidial fate and measuring host cell antifungal activity using a reporter of microbial viability in the lung. Cell Rep 2: 1762-1773.
Lam, et al., (J. of Immunol. Dec. 2005. 175(11). pp. 7496-7503). (Year: 2005).
Lam JS, Mansour MK, Specht CA, Levitz SM (2005) A model vaccine exploiting fungal mannosylation to increase antigen immunogenicity. J Immunol 175: 7496-7503.
Leibundgut-Landmann S, Wuthrich M, Hohl TM (2012) Immunity to fungi. Curr Opin Immunol 24: 449-458.
LeibundGut-Landmann S, Gross O, Robinson MJ, Osorio F, Slack EC, et al. (2007) Syk- and CARD9-dependent coupling of innate immunity to the induction of T helper cells that produce interleukin 17. Nat Immunol 8: 630-638.
Levitz SM, Nong S, Mansour MK, Huang C, Specht CA (2001) Molecular characterization of a mannoprotein with homology to chitin deacetylases that stimulates T cell responses to Cryptococcus neoformans. Proc Natl Acad Sci U S A 98: 10422-10427.
Lin L, Ibrahim AS, Xu X, Farber JM, Avanesian V, et al. (2009) Th1-Th17 cells mediate protective adaptive immunity against *Staphylococcus aureus* and Candida albicans infection in mice. PLoS Pathog 5: e1000703.
Lin, Y. et al. "Th17 cytokines and Vaccine Induced Immunity." Seminars in Immunopathology, vol. 32. No. 1. Springer-Verlag, 2010.
Loures FV, Rohm M, Lee CK, Santos E, Wang JP, et al. (2015) Recognition of Aspergillus fumigatus hyphae by human plasmacytoid dendritic cells is mediated by dectin-2 and results in formation of extracellular traps. PLoS Pathog 11: e1004643.
Marty AJ, Wuthrich M, Carmen JC, Sullivan TD, Klein BS, et al. (2013) Isolation of Blastomyces dermatitidis yeast from lung tissue during murine infection for in vivo transcriptional profiling. Fungal Genet Biol 56: 1-8.
McGreal EP, Rosas M, Brown GD, Zamze S, Wong SY, et al. (2006) The carbohydrate-recognition domain of Dectin-2 is a C-type lectin with specificity for high mannose. Glycobiology 16: 422-430.
Mori A, Oleszycka E, Sharp FA, Coleman M, Ozasa Y, et al. (2012) The vaccine adjuvant alum inhibits IL-12 by promoting PI3 kinase signaling while chitosan does not inhibit IL-12 and enhances Th1 and Th17 responses. Eur J Immunol 42: 2709-2719.
Rivera A, Hohl TM, Collins N, Leiner I, Gallegos A, et al. (2011) Dectin-1 diversifies Aspergillus fumigatus-specific T cell responses by inhibiting T helper type 1 CD4 T cell differentiation. J Exp Med 208: 369-381.
Robinson MJ, Osorio F, Rosas M, Freitas RP, Schweighoffer E, et al. (2009) Dectin-2 is a Syk-coupled pattern recognition receptor crucial for Th17 responses to fungal infection. J Exp Med 206: 2037-2051.
Romani L (2011) Immunity to fungal infections. Nat Rev Immunol 11: 275-288.
Saijo S, Ikeda S, Yamabe K, Kakuta S, Ishigame H, et al. (2010) Dectin-2 recognition of alpha-mannans and induction of Th17 cell differentiation is essential for host defense against Candida albicans. Immunity 32: 681-691.
Sancho D. & Reis E Sousa C., (2012. Annu Rev Immunol. 30:491-529). (Year: 2012).
Sato, et al., (2006. J Biol Chem. 281(50):38854-66) (Year: 2006).
Sato K, Yang XL, Yudate T, Chung JS, Wu J, et al. (2006) Dectin-2 is a pattern recognition receptor for fungi that couples with the Fc receptor gamma chain to induce innate immune responses. J Biol Chem 281: 38854-38866.
Specht CA, Nong S, Dan JM, Lee CK, Levitz SM (2007) Contribution of glycosylation to T cell responses stimulated by recombinant Cryptococcus neoformans mannoprotein. J Infect Dis 196: 796-800.
Specht, et al., (Nov.-Dec. 2015; 6(6): e01902-15. (Year 2015).
Spellberg B, Ibrahim AS, Lin L, Avanesian V, Fu Y, et al. (2008) Antibody titer threshold predicts anti-candidal vaccine efficacy even though the mechanism of protection is induction of cell-mediated immunity. J Infect Dis 197: 967-971.
Sterkel AK, Lorenzini JL, Fites JS, Subramanian Vignesh K, Sullivan TD, et al. (2016) Fungal Mimicry of a Mammalian Aminopeptidase Disables Innate Immunity and Promotes Pathogenicity. Cell Host Microbe 19: 361-374.
Taylor PR, Roy S, Leal SM, Jr., Sun Y, Howell SJ, et al. (2014) Activation of neutrophils by autocrine IL-17A-IL-17RC Interactions during fungal infection is regulated by IL-6, IL-23, RORgammat and dectin-2. Nat Immunol 15: 143-151.
Torrado, E et al. "IL-17 and Th17 cells in tuberculosis." Cytokine & Growth Factor Reviews, 21.6 (2010): 455-462.
Wang, et al., (J. of Immunol. 2014; 192: 1107-1119, prepublished online Jan. 3, 2014). (Year: 2014).
Wang H, Lebert V, Hung CY, Galles K, Saijo S, et al. (2014) C-type lectin receptors differentially induce th17 cells and vaccine immunity to the endemic mycosis of north america. J Immunol 192: 1107-1119.
Wurster, et al., (Autoantibodies (2nd Edition). Published 2007. Editors Shoenfeld, Gershwin and Meroni. Chapter 72-AntiMOG Antibodies. pp. 591-598. Abstract). (Year: 2007).
Wüthrich M, Filutowicz HI, Klein BS (2000) Mutation of the WI-1 gene yields an attenuated Blastomyces dermatitidis strain that induces host resistance. J Clin Invest 106: 1381-1389.
Wüthrich M, Gern B, Hung CY, Ersland K, Rocco N, et al. (2011) Vaccine-induced protection against 3 systemic mycoses endemic to North America requires Th17 cells in mice. J Clin Invest 121: 554-568.
Wüthrich M, Deepe GS, Jr., Klein B (2012) Adaptive immunity to fungi. Annu Rev Immunol 30: 115-148.
Wüthrich M, Ersland K, Sullivan T, Galles K, Klein BS (2012) Fungi subvert vaccine T cell priming at the respiratory mucosa by preventing chemokine-induced influx of inflammatory monocytes. Immunity 36: 680-692.
Wüthrich M, Brandhorst TT, Sullivan TD, Filutowicz H, Sterkel A, et al. (2015) Calnexin induces expansion of antigen-specific CD4(+) T cells that confer immunity to fungal ascomycetes via conserved epitopes. Cell Host Microbe 17: 452-465.

(56) References Cited

OTHER PUBLICATIONS

Wüthrich M, Wang H, Li M, Lerksuthirat T, Hardison SE, et al. (2015) Fonsecaea pedrosoi-induced Th17-cell differentiation in mice is fostered by Dectin-2 and suppressed by Mincle recognition. Eur J Immunol 45: 2542-2552.
Yonekawa A, Saijo S, Hoshino Y, Miyake Y, Ishikawa E, et al. (2014) Dectin-2 is a direct receptor for mannose-capped lipoarabinomannan of mycobacteria. Immunity 41: 402-413.
Yonekawa et al., (Immunity. vol. 41, Issue 3, Sep. 2014, pp. 402-413) (Year: 2014).
Zarnowski R, Westler WM, Lacmbouh GA, Marita JM, Bothe JR, et al. (2014) Novel entries in a fungal biofilm matrix encyclopedia. MBio 5: e01333-01314.
Zelante T, De Luca A, Bonifazi P, Montagnoli C, Bozza S, et al. (2007) IL-23 and the Th17 pathway promote inflammation and impair antifungal immune resistance. Eur J Immunol 37: 2695-2706.
Zhu LL, Zhao XQ, Jiang C, You Y, Chen XP, et al. (2013) C-type lectin receptors Dectin-3 and Dectin-2 form a heterodimeric pattern-recognition receptor for host defense against fungal infection. Immunity 39: 324-334.

* cited by examiner

A.

| Accession number | Molecular Weight | peptide specific fragments positive fractions | peptide specific fragments negative fractions |
|---|---|---|---|
| BDFG-08749T0 | 57 kDa | 10 | 0 |
| BDFG-05190T0 | 58 kDa | 1 | 9 |

| | Accession Number | Molecular Weight | Protein Grouping Ambiguity - | Protein Grouping Ambiguity + |
|---|---|---|---|---|
| Eng2 | BDFG_08749T0 | 57 kDa | (0) | 10 |
| | BDFG_07018T0 | 19 kDa | (0) | 6 |
| | BDFG_06523T0 | 28 kDa | (0) | 5 |
| | BDFG_04048T0 | 256 kDa | 4 | 4 |
| | BDFG_02583T0 {+2} | 573 kDa | 2 | 4 |
| | BDFG_00780T0 | 286 kDa | 3 | 3 |
| | BDFG_01495T0 | 128 kDa | 3 | 3 |
| | BDFG_01597T0 | 60 kDa | (0) | 3 |
| | BDFG_05417T0 | 60 kDa | 3 | 2 |
| | BDFG_01601T0 {+1} | 331 kDa | 2 | 2 |
| | BDFG_04108T0 | 56 kDa | 4 | 2 |
| | BDFG_03828T1 | 67 kDa | 1 | 2 |
| | BDFG_00614T0 | 553 kDa | 1 | 2 |
| | BDFG_00961T0 | 123 kDa | 0 | 2 |
| | BDFG_06729T0 | 122 kDa | 2 | 2 |
| | BDFG_07087T0 | 293 kDa | 1 | 2 |
| | BDFG_02872T0 | 73 kDa | 2 | 2 |
| | BDFG_05458T0 | 80 kDa | (0) | 2 |
| | BDFG_05919T0 | 139 kDa | (0) | 2 |
| | BDFG_04572T0 | 193 kDa | 2 | 2 |
| | BDFG_04068T0 | 44 kDa | 0 | 2 |
| | BDFG_06927T0 | 135 kDa | 2 | 2 |
| | BDFG_09351T0 | 89 kDa | 1 | 2 |
| | BDFG_05294T0 | 138 kDa | (0) | 2 |
| | BDFG_03925T0 | 129 kDa | (0) | 2 |
| | BDFG_07915T0 | 103 kDa | 0 | 2 |
| | BDFG_07434T1 | 29 kDa | 1 | 2 |
| | BDFG_04655T0 | 104 kDa | 0 | 2 |
| | BDFG_08196T0 | 56 kDa | (0) | 2 |
| | BDFG_01921T0 | 77 kDa | 1 | 2 |
| | BDFG_08026T0 | 213 kDa | 2 | 2 |
| | BDFG_08210T0 | 27 kDa | 0 | 2 |
| | BDFG_01335T0 | 124 kDa | (0) | 2 |
| | BDFG_03541T0 {+1} | 42 kDa | 4 | 1 |
| | BDFG_07340T0 | 111 kDa | 2 | 1 |
| | BDFG_03802T0 | 215 kDa | 2 | 1 |
| | BDFG_01718T0 | 232 kDa | 2 | 1 |
| | BDFG_03682T0 | 90 kDa | 2 | 1 |

| Accession Number | Molecular Weight | Protein Grouping Ambiguity - | Protein Grouping Ambiguity + |
|---|---|---|---|
| BDFG_02222T0 | 88 kDa | 2 | 1 |
| BDFG_08519T0 | 153 kDa | 2 | 1 |
| BDFG_09050T0 | 62 kDa | 2 | 1 |
| BDFG_03144T0 | 73 kDa | 4 | 1 |
| BDFG_05047T0 | 132 kDa | 2 | 1 |
| BDFG_04861T0 | 36 kDa | 2 | 1 |
| BDFG_08900T0 {+1} | 120 kDa | 2 | 1 |
| BDFG_02402T0 | 200 kDa | 2 | 0 |
| BDFG_00182T0 | 143 kDa | 3 | 0 |
| BDFG_06246T0 | 103 kDa | 3 | 0 |
| BDFG_03238T0 | 24 kDa | 2 | 0 |
| BDFG_00776T0 | 130 kDa | 3 | 0 |
| BDFG_09157T0 | 78 kDa | 2 | 0 |
| BDFG_08295T0 | 79 kDa | 2 | 0 |
| BDFG_07373T0 | 120 kDa | 2 | 0 |
| BDFG_06418T0 | 155 kDa | 2 | 0 |
| BDFG_05270T0 {+1} | 85 kDa | 2 | 0 |
| BDFG_01899T0 | 162 kDa | 2 | 0 |
| BDFG_07286T0 | 204 kDa | 2 | 0 |
| BDFG_08922T0 | 32 kDa | 2 | (0) |
| BDFG_01989T1 | 38 kDa | 2 | (0) |
| BDFG_07046T0 | 133 kDa | 2 | (0) |
| BDFG_09102T0 | 54 kDa | 2 | (0) |
| BDFG_04649T0 | 51 kDa | 2 | (0) |
| BDFG_05790T0 | 77 kDa | 2 | (0) |
| BDFG_01653T0 | 39 kDa | 2 | (0) |
| BDFG_07637T0 | 95 kDa | 2 | (0) |

pooled fractions #1-7 from Fig. S1C with no ligand activity pooled fractions #9-13 from Fig. S1C with ligand activity

Recombinant Bl-Eng2 sequence expressed in Pichia: 637 amino acids SEO ID NO:2

MRFPSIFTAV LFAASSALAA PVNTTTEDET AQIPAEAVIG YSDLEGDFDV

AVLPFSNSTN NGLLFINTTI ASIAAKEEGV SLEKREAEAR ATKLALLAAL

AKLSTGAYVL QDDYQPSNFF DDFAFFDGPD PSNAYV TYV DKSKALRDGL

ASNNNDFVYLG VDHQNVARGR GRESVRLETK KSYKHGLIVA DISHMPGNIC

GTWPAFWATG ATWPDDGEFD IIEGVNKQNK NVVALHTTAGC KVEDNNKYSG

ILVTKDCDVY SPNQPSNQGC LFRAPSATSY GTAFNSIGGG VYATEWTSDS

ISVWFFPRYQ IPSNINDENP DPSTWPRPIA HFTGCEFDKF FQEQRIIFNT

AFCGDWAKAT WNENGCAAGG RTCEDYVKNN PWAFSEAFWS INYMKVFQNK

QGDTSTSTTT SSTSSTSSSS TEAPTTTMTT SSTYEPSVSS STAPEPSQSA

STPSEYPQPS TAEPTASSSS YPKSSEASTD SPVPTDYPVP SSDEPTVPSA

TYSESSPVPT DYPVPSSDEP TVPSATYSES TPSASAPSEY PTGTASVDPT

DVSSCTPPPT QSCITYTTKT TIAIVVTAPES YKEAIQTESA EDETEPAAYP

TEPAGYPTND KYGLEQKLIS EEDLNSAVDH HHHHH

FIGS. 9A-E
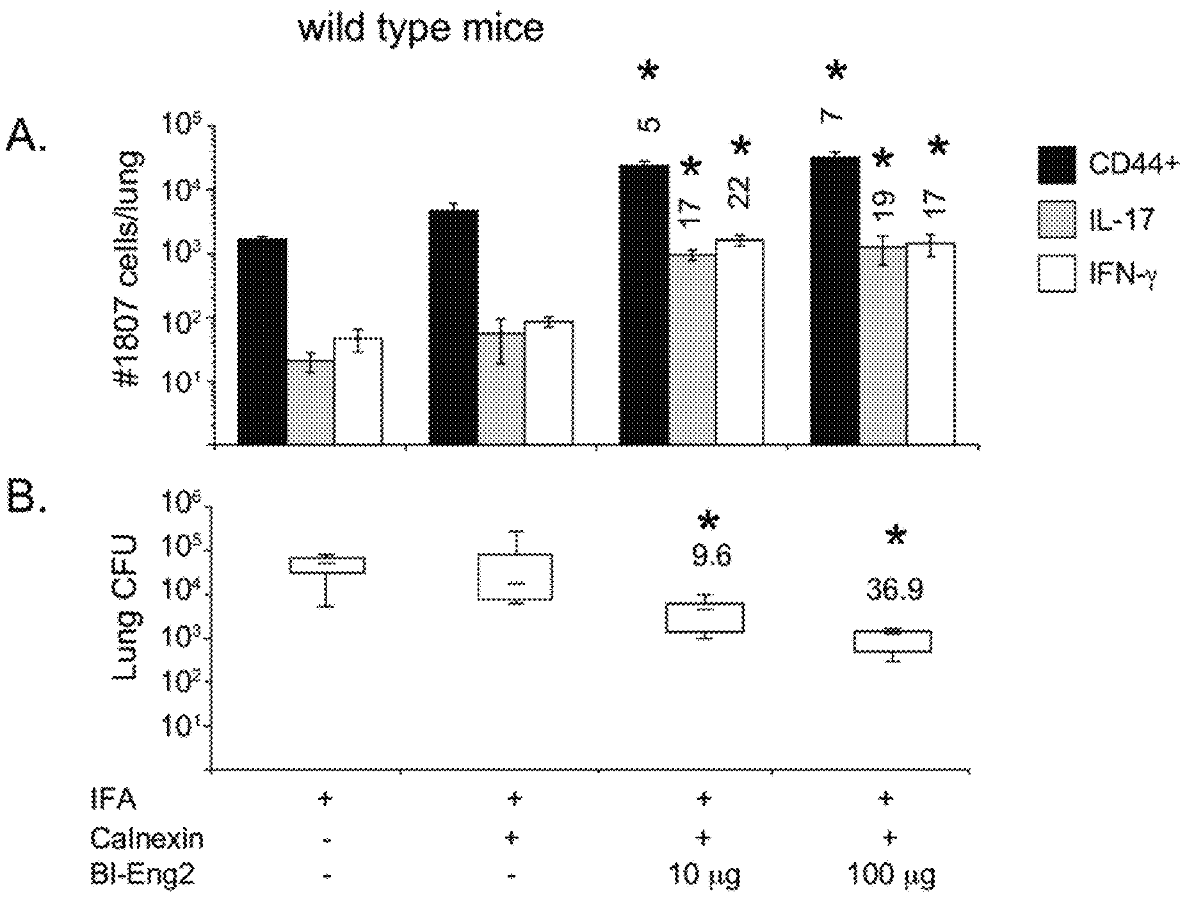

FIG. 16

```
SEQ ID NO:3  AfEng2   MAPSSLLLSVGSLITSSLVSATALEARQSQTYQLAESW-QGESFINDWNFFDGADPTNGY   59
SEQ ID NO:12 AfEng3   ------------MYIRSTLPILGFSATGMAAYVLEDDYGTSTSFFDKFSFFTDPDPTGGF   48
SEQ ID NO:13 PdEng2   -MPS--------LQTLIPAAAIAWLVGTASAAYTLQDVY-DSTNFFDGFNFHDGPDPTNGF   51
SEQ ID NO:14 CiEng2   ------------MRAAKVTLLAALAQLAAASYELMDDY-NPSNFFDKFEFFSGRDPSNGY   47
SEQ ID NO:15 CpEng2   ------------MRAAKVTLLAALAQLAAASYELMDDY-NPSNFFDKFEFFSGRDPSNGY   47
SEQ ID NO:1  BlEng2   ------------MRATKLALLAALAKLSTGAYVLQDDY-QPSNFFDDFAFFDGPDPSNAY   47
SEQ ID NO:16 HcEng2   ------------MRTTKLTLLATLAKLSAGTYVLKDDY-QPSNFFDNFNFFNGPDPSNGY   47
                                          :      :* * : :    .*:: : *. . **:..:

             AfEng2   VTYVNQSFAKQSGLVKVTESGSFYMGVDYESTLNPNGAGRESVRIESKNYYTEGLYVIDI   119
             AfEng3   VSYVDRNTAQDTGLI-FA-NGAVYMGVDHTNV--AGSSGRQSVRLTSTKSYTHGLIILDL   104
             PdEng2   VDYANAETANNAGLAGLS-QDGVYMGVDHTTM--SPPNGRASVRVESQKQYTLGLFIADI   108
             CiEng2   VAYQGKEAALSSNLAQKL-ENSIRIGSDSTDI--ATGPGRRSVRLETKARYKHGLIVADI   104
             CpEng2   VAYQGKEAALSSNLAQKL-ENSIRIGSDSTDI--ATGSGRRSVRLETKARYKHGLIVADI   104
             BlEng2   VTYVDKSKALRDGLASNN-NDFVYLGVDHQNV--ARGRGRESVRLETKKSYKHGLIVADI   104
             HcEng2   VTYLDKSNAVNNGLASNE-NDFVYLGVDSKNV--AKGLGRESVRLETKKTYKHGLIVVDI   104
                      * * . . *   .*     .. . :* *          ** ***: :   *. ** : *:

             AfEng2   EHMPGSICGTWPAFWSVGKNWPNDGEIDIIEGVNLQKANKIVLHTSGSCDVSGSNDMTGT   179
             AfEng3   EHMPGGICGTWPAFWMLGPDWPSHGEIDIIEGVNTQPVNQMTLHSTDGCSIA-NGGFTGT   163
             PdEng2   KHMPGAECGSWPAFWTYGPDWPNAGEIDIMEGVNTQLTNDVTLHTSGSCSMN-NPNSQLG   167
             CiEng2   KHMPGSICGIWPAFWTVGSRWPEHGEMDIIEGVNRQSINKMALHTTAGCKINSNGDFTGV   164
             CpEng2   KHMPGSICGVWPAFWTVGSRWPEHGEMDIIEGVNRQSINKMALHTTAGCKINSNGDFTGV   164
             BlEng2   SHMPGNICGTWPAFWATGATWPDDGEFDIIEGVNKQNKNVVALHTTAGCKVEDNNKYSGI   164
             HcEng2   SHMPGGICGTWPALWSTGATWPEDGELDIIEGVNSQTKNVVALHTTAGCKVEDNSNYSGE   164
                      .****  ** ***:*  *  **. **:**:**** *  * :.**:: .*.:  .

             AfEng2   LSSSECGE----ASGTVGCVVKGTNG-SSGDPFNESGGGVYAMEWTDTFIKIWFFPRSQI   234
             AfEng3   LLTSNCYDYAPSQDTNAGCGIAATSSRTYGTGFNNAGGGIYATEWTSAGISIWFFPRGST   223
             PdEng2   SVLSN-----ADCSGTRGCGQATIDPSNYGTGFNTIGGGVYAMEWTNEVIAVYFFPRYAI   222
             CiEng2   VETPDCDVNSPNQAPNQGCLFTSSQGNSYGTNFNNRNGGVYAMEWTSDEITVWFFPRGNI   224
             CpEng2   VETPDCDVNSPNQAPNQGCLFTSSQGNSYGTNFNNRNGGVYAMEWTSDEITVWFFPRGNI   224
             BlEng2   LVTKDCDVYSPNQPSNQGCLFRAPSATSYGTAFNSIGGGVYATEWTSDSISVWFFPRYQI   224
             HcEng2   LVTKDCDINSPTQPGNQGCLFRAPSSMSYGNSFNSIGGGIYAAEWTTDSISVWFFPRYRI   224
                         :          . **     .  . *  **  .**:** ***    *  ::****
```

FIG. 16 CONTINUED

```
AfEng2      PASLASGNPDTSSFGTPMAHLQG-SCDFAERFKAQKLIIDTTFCGDWAGNVFAES-TCPM      292
AfEng3      PTDIRAGTPNPTNWGPPLAKFAPGSCSFDAHFSEMQIVFDTTFCGGWAGSVWGSG-SCAS      282
PdEng2      PDDINSGNPDPSTWGTPLTNFVGDSCNIGSHFKNHYIVFDTTFCGDWAGGVWGD--QCGA      280
CiEng2      PDDVNSQNPDPSKWGKPSARFSG-DCDLDRFVQDQRIIFNTAFCGDWAKGLWNSDSVCRA      283
CpEng2      PDDVNSQNPDPSKWGKPSARFSG-DCDLDRFVQDQRIIFNTAFCGDWAKGLWNSDSVCRA      283
BlEng2      PSNINDENPDPSTWPRPIAHFTG--CEFDKFFQEQRIIFNTAFCGDWAKATWNEN-GCAA      281
HcEng2      PSDINSEHPDPSSWARPIAHFTG--CEFDKFFQEQRIIINTAFCGDWAKNTWSQDAECAA      282
            * .:    *: :.:  * :.:    *.:   ..   :::*:***.**    : .   *

AfEng2      SDPSSPMQSCVNYVAQNPAAFKEAYWEINSIKIYQYGVSAASSAAVSQATASKVEGTRVS      352
AfEng3      V-----APSCQDFVANNPSAFREAYWLIESLKVYQDAPGESNNMRMNATSHLN-------      330
PdEng2      R-----AATCEDFVSQNPAAYEESYWLVNSVKVYTN------------------------      311
CiEng2      K-----GPSCEDYVKNNPKDFAEAYWEIYGMKVYSKGQGQKISSAATSPTQASTTQ--VS      336
CpEng2      K-----GPSCEDYVKNNPKDFAEAYWEIYGMKVYSKGQGQKISSAATSPTQASTTQ--VS      336
BlEng2      G-----GRTCEDYVKNNPWAFSEAFWSINYMKVFQNKQGDTSTSTTTSSTSSTSSS--S-      333
HcEng2      K-----ADSCEAYVQNNPSAFSEAYWSINYMKVFQDEVVDYPGDSTTTTTSTTASQ--TD      335
                    :*  :* :**  :  *::* :  :*::

AfEng2      AQAANTA---TPTVPAPVETTTVPQPAQTNTVATSAADHATPSSAET------------      396
AfEng3      VQLPRKG------------GRRSPGLHGR-------------GFLEGTG---KW*-----      356
PdEng2      ------------------------------------------------------------      311
CiEng2      TT----Q--ISSAQSASASASVSDGPDTSSNTPPSA--------TESGN------ASSIE      376
CpEng2      TT----Q--ISSAQSASASASVSDGPDTSSNTPPSA--------TGSGN------ASSIE      376
BlEng2      TEAPTTTMTTSSTYEPSVSSSTAPEPSQSASTPSEY---PQPSTAEPTASSSSYPKSSFA      390
HcEng2      STEPTTTTTTS-------------------------------------------------      347
```

FIG. 16 CONTINUED

```
AfEng2    --TTVPAATGAFSVSATEGGDSELESTSTVYVTSTTTICP--VAESSSAAAAGGKEDAPS    452
AfEng3    ------------------------------------------------------------    356
PdEng2    ------------------------------------------------------------    311
CiEng2    SRSTDVEPTKTPT-----GTDGGASLT--------NAPCNGPNCPSQSPTTSGG------    417
CpEng2    SRSTDAEPTKAPT-----GTDGGASPT--------NAPCNGPNCPSQSPTTSGG------    417
BlEng2    STD-SPVPTDYPV-----PSSDEPTVPSATYSESSPVPTDYPVPSSDEPTVPSAT-----    439
HcEng2    ----------------------------------------TTTTTSTQPADTGAT-----    362

AfEng2    NGTSGAEVAATSVAAAAPAA------ATSGHFGADAIANSAAATSTDAQSESATSRLTAG    506
AfEng3    ------------------------------------------------------------    356
PdEng2    ------------------------------------------------------------    311
CiEng2    ------------VSPTDKSEYPANPGTTGGSFLPTN-KPEIFSSCT--PRTTCVT-YTRI    461
CpEng2    ------------VSPTDKSEYPANPGTTDGSPLPTN-KPEIPTSCT--PRTTCVT-YTRI    461
BlEng2    -------YSESLPSASAPSEYPTGTAS--------V-DPTDVSSCTPPPTQSCIT-YTTK    482
HcEng2    -------NTDSSPSASATNEYPTGSAS--------V-EPTDIASCTPPPTESCIT-YTTK    405

AfEng2    ALSEIPTAPFEFVSQAVSTGSFDDSDTAQGDSEEQGSIASASVAPSTIFVPASSSAAALG    566
AfEng3    ------------------------------------------------------------    356
PdEng2    ------------------------------------------------------------    311
CiEng2    ETVTYINKNFAFFQTGVQSFT-----KASGDDE--------SIIPIR-------------    495
CpEng2    ETVTYINKNFAFFQTGVQSFT-----KASGDDE--------SIIPIR-------------    495
BlEng2    TTIAIVVTAPESYKEAIQ--------TESA---------EDETEP---------------    510
HcEng2    TTIAVVVTP-TGYNEAIIPIP-----TESAEYETE--PTENPIEPSEYPTA------PVG    451

AfEng2    GSSIASSFASSRLIFRPTGSSTAASATAIATWSPTAGESASGTAKESATLTTPSEVFFTF    626
AfEng3    ------------------------------------------------------------    356
PdEng2    ------------------------------------------------------------    311
CiEng2    ------------------------------------------------------------    495
CpEng2    ------------------------------------------------------------    495
BlEng2    -----AAY-----PTEPAGYPTNDKY----------------------------------    526
HcEng2    YPTEPIGY-----PTEPIGYPTNDQDVPLKRRQ-HIKKHIAGTHH---------------    490

AfEng2    GLSNGANRMSVGLSGLIGVMFIAALA* 652
AfEng3    --------------------------- 356
PdEng2    --------------------------- 311
CiEng2    --------------------------- 495
CpEng2    --------------------------- 495
BlEng2    --------------------------- 526
HcEng2    --------------------------- 490
```

VACCINE ADJUVANT

CROSS-REFERENCE TO RELATED APPLICATIONS

This application is a continuation application of U.S. application Ser. No. 15/787,021 filed on Oct. 18, 2017, which claims priority to U.S. Provisional Application 62/411,281, filed Oct. 21, 2016, both of which are incorporated by reference herein in their entirety.

STATEMENT REGARDING FEDERALLY SPONSORED RESEARCH

This invention was made with government support under AI093553 awarded by the National Institutes of Health. The government has certain rights in the invention.

SEQUENCE LISTING

A Sequence Listing accompanies this application and is submitted as an ASCII text file of the sequence listing named "960296_04119_ST25.txt" which is 39.8 KB in size and was created on Feb. 24, 2021. The sequence listing is electronically submitted via EFS-Web with the application and is incorporated herein by reference in its entirety.

BACKGROUND

Vaccines have been hailed as one of the greatest achievements in public health during the past century. The global eradication of Smallpox virus in humans and Rinderpest virus in animals, and the near eradication or successful prevention of other viral or bacterial infections, for example meningitis in children due to *Hemophilus influenza* Type B, offer compelling examples. Yet, the development of safe and efficacious vaccines against fungi has been a major hurdle. This difficulty stems from the relative genetic complexity and intractability of fungi in the laboratory, limited knowledge of the mechanisms that underpin anti-fungal protective immunity, and a lack of defined antigen (Ag) candidates for vaccine protection against fungal pathogens.

To date, only two vaccines against fungi have moved into clinical trials. An investigational candidate vaccine containing rAls3p-N(NDV-3), directed against *Candida* (and also *S. aureus*), has been tested for safety and immunogenicity in volunteers in a Phase I trial. Another candidate vaccine containing rSap2p was found to be tolerated and effective in inducing specific antibodies and B cell memory in women with recurrent vulvovaginitis in a European clinical trial. Highly conserved Ags that are shared across fungal pathogens in a family or taxon would be preferable, but the only such component that has shown promise is β-glucan. Cassone et. al. reported that this shared cell wall component served as the basis for a glyco-conjugate vaccine against *Candida* and *Aspergillus*. This preparation has not yet moved into clinical trials, but β-glucan particles (GPs) could serve as an experimental platform for the delivery of candidate vaccines against fungi.

The incidence of fungal infections and mycoses has increased significantly in the past two decades, mainly due to the growing number of individuals who have reduced immunological function (immuno-compromised patients), such as cancer patients, patients who have undergone organ transplantation, patients with AIDS, patients undergoing hemodialysis, critically ill patients, patients after major surgery, patients with catheters, patients suffering from severe trauma or burns, patients having debilitative metabolic illnesses such as diabetes mellitus, persons whose blood is exposed to environmental microbes such as individuals having indwelling intravenous tubes, and even in some elderly individuals. Fungal infections are often also attributed to the frequent use of cytotoxic and/or antibacterial drugs, which alter the normal bacterial flora. Fungi include molds, yeasts and higher fungi. All fungi are eukaryotic and have sterols but not peptidoglycan in their cell membrane. They are chemoheterotrophs (requiring organic nutrition) and most are aerobic. Many fungi are also saprophytes (living off dead organic matter) in soil and water and acquire their food by absorption. Characteristically fungi also produce sexual and asexual spores. There are over 100,000 species recognized, with 100 infectious members for humans.

Human fungal infections are uncommon in generally healthy persons, being confined to conditions such as Candidiasis (thrush) and dermatophyte skin infections such as athlete's foot. Nevertheless, yeast and other fungi infections are one of the human ailments which still present a formidable challenge to modern medicine. In an immuno-compromised host, a variety of normally mild or nonpathogenic fungi can cause potentially fatal infections. Furthermore, the relative ease with which human can now travel around the world provides the means for unusual fungal infections to be imported from place to place. Therefore, wild and resistant strains of fungi are considered to be one of the most threatening and frequent causes of death mainly in hospitalized persons and immuno-compromised patients.

The identity of conserved antigens among pathogenic fungi is poorly understood. This is especially true for immunologically significant antigens that may serve as immunogens to vaccinate against infection. There are currently no commercial vaccines against fungi despite the growing problem of fungal infections. A vaccine against pathogenic fungi, especially one that protects against multiple fungal pathogens, would be of enormous clinical benefit, and of commercial interest. Improved vaccines and methods of vaccination against fungi are needed in the art.

Needed in the art is an improved adjuvant for a fungal, bacterial and viral vaccines as well as novel vaccine antigens.

SUMMARY OF THE INVENTION

The present invention relates to a vaccine composition comprising a Dectin-2 ligand.

In a first aspect, described herein is a vaccine suitable to immunize a patient comprising an adjuvant, wherein the adjuvant is a Dectin-2 ligand. In some embodiments, the Dectin-2 ligand is a glycoprotein. In some embodiments, the Dectin-2 ligand is Bl-Eng2. In one embodiment, Bl-Eng2 comprises SEQ ID NO: 1. In some embodiments, Bl-Eng2 comprises O-linked glycosylations.

In some embodiments, the vaccine immunizes a patient against a fungal infection. In some embodiments, the vaccine comprises glucan particles. In some embodiments, the vaccine immunizes a patient against a bacterial infection. In some embodiments, the vaccine immunizes a patient against a viral infection.

In a second aspect, described herein is a method of preparing a vaccine comprising the steps of, (a) preparing a pharmaceutically acceptable vaccine stabilizer; and (b) introducing to the vaccine stabilizer a suitable antigen and an adjuvant, wherein the adjuvant is a Dectin-2 ligand.

In a third aspect, described herein is a method of protecting a patient from an infection comprising the steps of: (a) obtaining a vaccine suitable to immunize a patient, wherein the vaccine comprises an adjuvant and a suitable antigen, wherein the adjuvant is a Dectin-2 ligand; and (b) providing a therapeutically effective amount of the vaccine to a subject, wherein the subject is protected from the infection. In some embodiments, the infection is a fungal infection and the patient is protected from a fungi infection. In some embodiments, the antigen is a fragment of calnexin and the fungi is selected form the group consisting of *Histoplasma, Coccidiodes, Paracoccidioides, Penicillium, Blastomyces, Sporothrix, Aspergillus, Pneumocystis, Magnaportha, Exophiala, Neuroaspora, Cryptococcus, Schizophyllum*, and *Candida.*

In a forth aspect, described herein is a vaccine composition comprising Bl-Eng2 and a pharmaceutically acceptable carrier. In some embodiment, Bl-Eng2 comprises SEQ ID NO:1. In some embodiments, Bl-Eng2 comprises O-linked glycosylations. In some embodiments, the vaccine is suitable to immunize a subject against a fungal infection. In some embodiments, the vaccine additionally comprises an adjuvant. In one embodiment, the vaccine comprises incomplete Freunds adjuvant. In some embodiment, the vaccine comprises a fragment of Bl-Eng2.

In a fifth aspect, described herein is a method of protecting a patient from an infection comprising the steps of: (a) obtaining a vaccine composition comprising Bl-Eng2 and a pharmaceutically acceptable carrier; and (b) providing a therapeutically effective amount of the vaccine to a subject, wherein the subject is protected from the infection. In some embodiments, the infection is a fungal infection. In some embodiments, Bl-Eng2 comprises SEQ ID NO:1. In some embodiments, Bl-Eng2 comprises O-linked glycosylations.

BRIEF DESCRIPTION OF DRAWINGS

FIGS. 7A-7B show mass spec analysis identifies Bl-Eng2 as a candidate ligand for Dectin-2. (A) Complete list of Mass spec candidates for Dectin-2 ligands. (B) Amino acid sequence of recombinant Bl-Eng2 contains 637 amino acids (SEQ ID NO:2). Colored aa match the protein domains illustrated in FIG. 2B.

FIG. 16 shows a sequence alignment of Eng2 (SEQ ID NO:3) and Eng 3 (SEQ ID NO:12) from *Aspergillus fumigatus*, Eng2 (SEQ ID NO:13) from *Pseudogymnoascus destructans*, Eng2 (SEQ ID NO:14) from *Coccidioides immitis*, Eng2 (SEQ ID NO:15) from *Coccidioides posadasii*, Eng2 (SEQ ID NO:1) from *Blastomyces dermatitidis*, and Eng2 (SEQ ID NO:16) and *Histoplasma capsulatum*. The sequence of conserved peptide #1 is shaded.

DETAILED DESCRIPTION OF THE INVENTION

In General

Figures 1A, 1B, 1C, 1D, 1E, 1F:
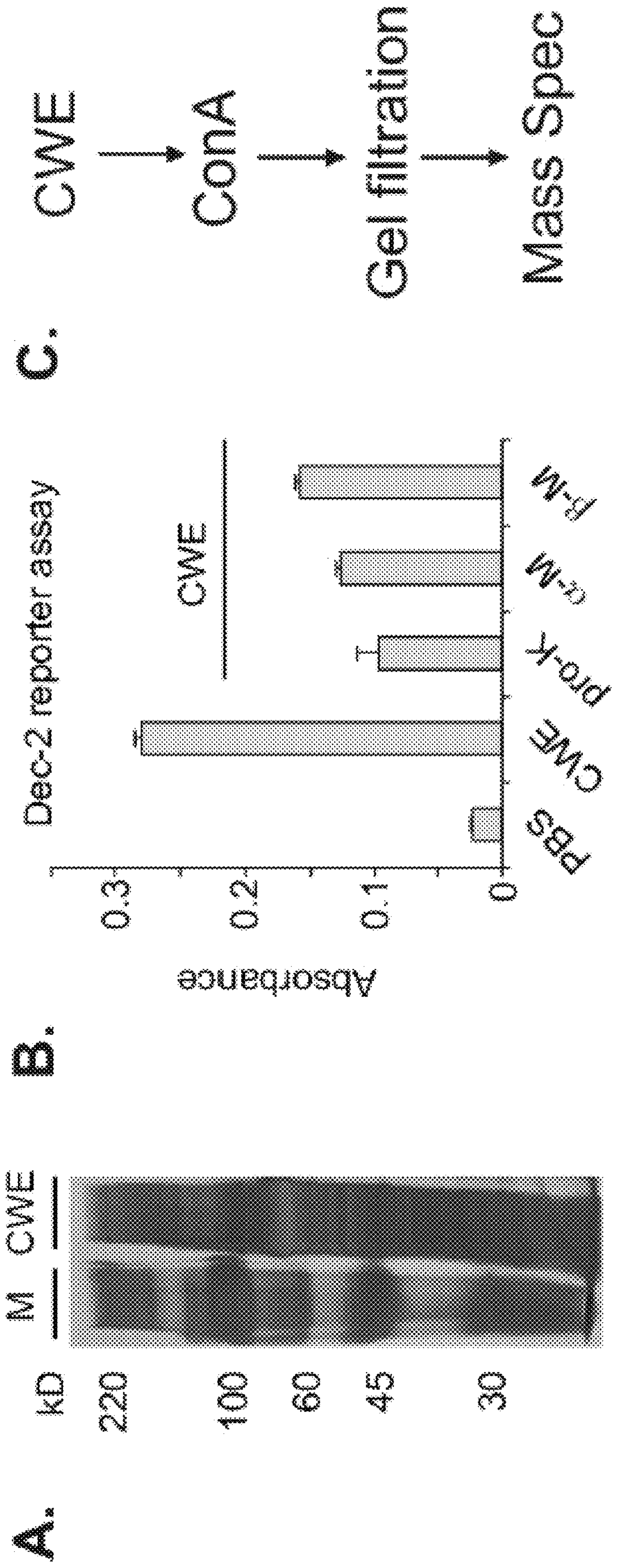
FIGS. 1A-1F demonstrate identification of ligand activity and enrichment by ConA. (A) Silver-stained SDS-PAGE gel of CWE after water wash and sonication. (B) Dectin-2 reporter cells were stimulated with plate-coated CWE treated with or without proteinase K (pro-K), α-Mannosidase (α-M), or β-Mannosidase (β-M). After 18 h, lacZ activity was measured. Data are the mean±SD of duplicate wells. (C) Flow chart of ligand enrichment and purification. (D) CWE was incubated with ConA resin. Flow-through (FL) and eluate (E) were run on SDS-PAGE gel, silver stained and analyzed for ligand activity. (F) ConA eluate was further separated by size exclusion using a BioLogic LP system (Biorad) and Ultro Gel ACA44 resin (Pall Corporation) at a flow rate of 1 ml/min (blue line represents the trace line of $A_{280}$ absorption). Fractions were tested by Dectin-2 reporter cells for ligand activity. Fractions 4-6 contained most of the ligand activity and were separated by a second run over the size exclusion column (see FIG. 6C).

All publications, patents, and patent applications mentioned in this specification are herein incorporated by reference to the same extent as if each individual publication, patent, and patent application was specifically and individually indicated to be incorporated by reference.

In one embodiment, the present disclosure describes an adjuvant for use in a vaccine. The adjuvant is a Dectin-2 ligand, which stimulates an immune response when administered in a vaccine composition. In another embodiment, the present disclosure describes an antigen for use in a vaccine. The antigen is Bl-Eng2 or a variant thereof, which stimulates an immune response when administered in a vaccine.

Due to changes in naming conventions and related homologs, Bl-Eng2 of the current invention was named "Bl-Eng3" in corresponding U.S. Provisional Application No. 62/411,281, which is incorporated herein by reference. The polypeptide sequence of the novel adjuvant and antigen has not changed.

In one embodiment, the Dectin-2 ligand is glycosylated. In one embodiment, the Dectin-2 ligand comprises at least one N-linked glycan, O-linked glycan or combinations thereof. In one embodiment, the Dectin-2 ligand comprises at least one O-ling glycan. In one embodiment, the Dectin-2 ligand is Bl-Eng2, MP98, Furfurman, or Man-LAM.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

As used herein the specification, "a" or "an" may mean one or more, unless clearly indicated otherwise. As used herein in the claims, when used in conjunction with the word "comprising," the words "a" or "an" may mean one or more than one.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "post-translational modification," or "PMT" as used herein, refers to the covalent and generally enzymatic modification of proteins during or following protein biosynthesis. Post-translational modifications may occur at the C- or N-termini of the protein or on the amino acid side chains of the protein. PTMs may include, but are not limited to, the addition of phosphates, carbohydrates, acetates, amide groups, methyl groups, lipid molecules, and combinations thereof. The addition of PTM to a protein may be, but are not limited to, enzymatic phosphorylation, glycosylation, acylation, alkylation, methylation and combinations thereof. In one embodiment of the invention, PTMs include N- and O-linked glycosylations.

The term "glycoprotein," as used herein, refers to a protein in which a carbohydrate, monosaccharide or glycan is attached to a hydroxyl or other functional group of the protein. The glycoprotein is the result of a post-translational modification wherein a carbohydrate has been covalently linked to the protein. The glycosylation may be, but is not limited to, the covalent addition of any glucan known in the art and may be one or more of a monosaccharide, a carbohydrate, a glucose, a mannose, an N-acetylglucosamine, and combinations thereof. In one embodiment of the invention, the glycol protein comprises at least one O-linked glycan.

The term "therapeutically effective amount," as used herein, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and may be determined by a physician.

The term "protected," as used herein, refers to immunization of a patient against a disease. The immunization may be caused by administering a vaccine comprising an antigen. Specifically, in the present invention, the immunized patient is protected from a fungal, bacterial, or viral infection.

The term "vaccine," as used herein, refers to a composition that includes an antigen. Vaccine may also include a biological preparation that improves immunity to a particular disease. A vaccine may typically contain an agent, referred to as an antigen, that resembles a disease-causing microorganism, and the agent may often be made from weakened or killed forms of the microbe, its toxins or one of its surface proteins. The antigen may stimulate the body's immune system to recognize the agent as foreign, destroy it, and "remember" it, so that the immune system can more easily recognize and destroy any of these microorganisms that it later encounters.

Vaccines may be prophylactic, e.g., to prevent or ameliorate the effects of a future infection by any natural or "wild" pathogen, or therapeutic, e.g., to treat the disease. Administration of the vaccine to a subject results in an immune response, generally against one or more specific diseases. The amount of a vaccine that is therapeutically effective may vary depending on the particular virus used, or the condition of the patient, and may be determined by a physician. The vaccine may be introduced directly into the subject by the subcutaneous, oral, oronasal, or intranasal routes of administration.

A vaccine of the present invention will include a suitable antigen to stimulate an immune response in a subject or patient. It is envisioned that vaccines of the present invention are not limited to a specific antigen or disease target, except where specifically specified. In some embodiments, the vaccine of the present invention provides immunity against a fungus, a parasite, a bacteria, a microbe, or a virus. In one embodiment, the antigen is Bl-Eng2 or a peptide fragment thereof and the vaccine composition provides immunity against a fungus.

In some embodiments, the vaccine of the present invention provides immunity against fungi. In one embodiment of the invention, the vaccine comprises an antigen for the family of ascomycetes in which the pan-fungal antigen Calnexin is highly conserved, and has been shown to confer protection against infection in experimental animal models. A non-limiting example of an antigen of the present invention is the calnexin fragment described in U.S. patent application Ser. No. 14/203,898 ("Method of Treating Fungal Infection") and U.S. patent application Ser. No. 14/643,693 ("Peptide MHCII Tetramers to Detect Endogenous Calnexin Specific CD4 T Cells'"), both of which are incorporated herein in their entirety.

In some embodiments, the vaccine of the present invention provides immunity against a *Blastomyces dermatitidis* infection. In one embodiment, the vaccine comprises Bl-Eng2 as an antigen to confer protection against a fungal infection. In some embodiments, the fungal infection is selected from the group consisting of *Blastomyces dermatitidis, Histoplasma capsulatum, Coccidioides posadasii, Coccidioides immitis, Aspergillus fumigatus* and *Pseudogymnoascus destructans*. In some embodiments, the Bl-Eng2 is a fragment of Bl-Eng2 comprising SEQ ID NO:4. Without wishing to be bound by any particular theory, SEQ ID NO:4 is conserved among *Blastomyces dermatitidis, Histoplasma capsulatum, Coccidioides posadasii, Coccidioides immitis, Aspergillus fumigatus* and *Pseudogymnoascus destructans*, and this conserved sequence may be responsible for Bl-Eng2 mediated protection against fungal infection.

Suitable Targets of the Present Invention

The term "fungi" or "funguses", as used herein, refers to a member of a large group of eukaryotic organisms that may include microorganisms, e.g., yeasts and molds. These organisms may be classified as a kingdom of fungi, which is separate from plants, animals, and bacteria. One major difference between fungi and the others is that fungal cells have cell walls that contain chitin, unlike the cell walls of plants, which contain cellulose.

These and other differences show that the fungi form a single group of related organisms, named the Eumycota (true fungi or Eumycetes), that share a common ancestor (a monophyletic group). This fungal group may be distinct from the structurally similar myxomycetes (slime molds) and oomycetes (water molds). Genetic studies have shown that fungi are more closely related to animals than to plants. In the present invention, the terms "fungi", "funguses", or "fungal" may refer to fungi which may cause infection in humans and animals.

In one preferred embodiment of the present invention, fungi may include *Candida albicans* (using *Candida* Adh1 or Als3 protein as an antigen), *Aspergillus fumigatus*, endemic systemic dimorphic fungi including *Coccidioides immitis* and *C. posadasii, Histoplasma capsulatum, Blastomyces dermatitidis, Paracoccidioides brasiliensis, Sporothrix schenkii* and *Penicillium marneffii*) and other ascomycetes using the shared and conserved antigenic domain of Calnexin.

Aside from fungi, the present invention may be used as an adjuvant for vaccination against any infectious disease that requires the development of cellular immunity, in particular T helper 1 and T helper 17 CD4+ cells and T cytotoxic 1 and T cytotoxic 17 CD8+ T cells. This group of microorganisms may include parasites, bacteria, and viruses.

In some embodiments, the present invention may be used as an adjuvant for vaccination against a bacterial infection. The bacteria may include, but is not limited to, *Mycobacterium tuberculosis*, and other intracellular bacteria that require T cell immunity for host protection. Any suitable antigen known in the art to protect against the target bacterial infection can be used in a vaccine composition with the adjuvant of the present invention. In one embodiment, the vaccine composition comprises Bl-Eng2 and Ag85B and protects against a *Mycobacterium tuberculosis* infection.

In some embodiments, the present invention may be used as an adjuvant for vaccination against a viral infection. The virus may include, but is not limited to, influenza A, and other viral infections that require cell mediated immunity for host protection. Any suitable antigen known in the art to protect against the target viral infection can be used in a vaccine composition with the adjuvant of the present invention. In one embodiment, the vaccine composition comprises Bl-Eng2 and nucleoprotein (NP) and protects against an influenza A infection.

Vaccine Administration

The term "administration," as used herein, refers to the introduction of a substance, such as a vaccine, into a subject's body through or by way of a route that does not include the digestive tract. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body.

Other possible routes of application are by spray, aerosol, or powder application through inhalation via the respiratory tract. In this last case the particle size that is used will determine how deep the particles will penetrate into the respiratory tract.

Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository. The term "animal-based protein", as used herein, refers to proteins that are sourced from ruminant milk, and other sources, for example the muscle meat, of an animal, particularly a mammal. Suitable animal-based proteins may include, but are not limited to, digested protein extracts such as N-Z-Amine®, N-Z-Amine AS® and N-Z-Amine YT® (Sheffield Products Co., Norwich, N.Y.), which are casein enzymatic hydrolysates of bovine milk.

The term "vegetable-based protein," as used herein, refers to proteins from vegetables. A vegetable-based protein may include, without limitation, soy protein, wheat protein, corn gluten, rice protein and hemp protein, among others. Preferred vegetable based proteins in the present invention are soy proteins and corn gluten. Corn gluten is a mixture of various corn-derived proteins. The soy proteins can include 100% soy protein (available as VegeFuel® by Twinlab), textured soy protein, and soybean enzymatic digest. Textured soy protein is a soy protein that is made from defatted soy flour that is compressed and processed into granules or chunks. Soybean enzymatic digest describes soybean peptones that result from the partial hydrolysis of soybean proteins.

Antibodies of the Present Invention

The term "antibody," as used herein, refers to a class of proteins that are generally known as immunoglobulins. The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "fusion protein," as used herein, refers to a hybrid polypeptide which comprises protein domains from at least two different proteins. Fusion proteins or chimeric proteins (literally, made of parts from different sources) are proteins created through the joining of two or more genes that originally coded for separate proteins. Translation of this fusion gene results in a single or multiple polypeptides with functional properties derived from each of the original proteins. Recombinant fusion proteins are created artificially by recombinant DNA technology for use in biological research or therapeutics. Chimeric or chimera usually designate hybrid proteins made of polypeptides having different functions or physico-chemical patterns. Chimeric mutant proteins occur naturally when a complex mutation, such as a chromosomal translocation, tandem duplication, or retrotransposition creates a novel coding sequence containing parts of the coding sequences from two different genes. Naturally occurring fusion proteins are commonly found in cancer cells, where they may function as oncoproteins. In one embodiment of the present invention, fusion proteins comprise at least one engineered intein.

The term "immune status" or "immunocompetence," as used herein, refers to the ability of the body to produce a normal immune response following exposure to an antigen. Immunocompetence is the opposite of immunodeficiency or immuno-incompetent or immuno-compromised.

The present invention is generally applied to humans. In certain embodiments, non-human mammals, such as mice and rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

Adjuvants of the Present Invention

As used herein, "Th17 cells" refers to a population of CD4+ T cells which produce Il-17. As used herein, "Th1 cells" refers to a population of CD4+ T cells which produce INF-7. As used herein, "Tc1 cells" refers to a population of cytotoxic CD8+ T cells that produce INF-7. Vaccine induced CD4+ T cells that produce IL-17 (Th17 cells) and INF-γ (Th1 cells) and CD8+ Tc1 cells that produce INF-7 are active in resistance against fungal, bacterial and viral infections. In one embodiment of the invention, the vaccine requires the activity of the Dectin-2 receptor on phagocytes that will trigger the development of antigen-specific Th17 and Th1 cells to mediate resistance.

As used herein, the term "Dectin-2" or "Dec-2" refers to a type II transmembrane C-type lectin receptor involved in the innate immune response. Note to be bound by any particular theory, Applicants working theory indicates that fungal vaccine recognition by the Dectin-2/FcRγ/Syk/Card9 signaling axis is required for the differentiation of Th17 and Th1 cells and the induction of vaccine-induced resistance to fungal infection (Wang et. al 2014 J Immunol).

As used herein, the term "Dectin-2 ligand" refers to a molecule capable of binding to or activating the Dectin-2/FcRγ/Syk/Card9 signaling axis to promote the differentiation of Th17 and Th1 cells. The molecule may be a protein, a lipid, a glycoprotein, a glycolipid or any glycan capable of binding Dectin-2. A suitable Dectin-2 ligand of the present invention is characterized by the ability to induce Dectin-2 signaling using Dectin-2 expressing B3Z T cell reporter cells (FIG. 2C) or to produce cytokines by bone marrow derived dendritic cells (BMDC) in a Dectin-2 dependent manner (for example, when comparing cytokine production by wild type vs. Dectin-2-deficient BMDCs) (FIG. 2D+E) and increasing the activation and differentiation of antigen-specific T cells in vivo (FIG. 3). In one embodiment the Dectin-2 ligand of the present invention is selected from the group consisting of Bl-Eng2, MP98, Furfurman from *Malassezia* sp., and Man-LAM (Ishikawa et al. 2003, Yonekawa et al. 2014). In another embodiment of the invention, the Dectin-2 ligand is a glycoprotein selected from the group consisting of MP98 and Bl-Eng2.

As used herein, the term "Bl-Eng2" refers to the fungal glycoprotein β-1,3-endoglucanase from *Blastomyces dermatitidis*. Bl-Eng2 has homology to *Aspergillus* fumigates endoglucanase 2 (Eng2) at the C-terminal glycosylation site, and endoglucanase 3 (Eng3) at the active site.

The predicted molecular weight of Bl-Eng2, based on amino acid sequence alone, is 57 kDa. However, Bl-Eng2 may appear as a 115-130 kDa band on an SDS-PAGE gel based on post-translation glycosylation. Bl-Eng2 comprises an 18 amino acid signal peptide, an N-terminal GH16 glycosyl hydrolase catalytic domain, and a C-terminal S/T-rich domain. Bl-Eng2 undergoes post-translational modification and has a number of O-linked glycosylation sites, which may be in the S/T-rich C-terminal domain. It is understood that mannose is the major monosaccharide present in the PTM glycosylation of Bl-Eng2 when it is expressed in *Pichia pastoris*. In one embodiment Bl-Eng2 comprises the sequence of SEQ ID NO:1. In one embodiment, the Bl-Eng2 is a fragment, single domain, or short glycan fragment of the full-length Bl-Eng2.

As used herein, the term "MP98" refers to the chitin deacetylase-like protein from *Cryptococcus neoformans* (Levitz et al., 2001). MP98 comprises an N-terminal cleavable signal sequence, a polysaccharide deacetylase domain found in fungal chitin deacetylases, and a serine/threonine-rich C-terminal region. The C-terminal region comprises N-liked glycosylation sites comprises covalently linked mannose.

A Dectin-2 ligand suitable for use as a vaccine adjuvant in the present invention may be in any form as discussed above. In one embodiment, the Dectin-2 ligand may be expressed in commercially available sources, e.g., *Pichia pastoris*. The Dectin-2 ligand may be expressed in any commercially available sources that is capable of post-translational protein modifications. The Dectin-2 ligand vaccine adjuvant may be then isolated and purified from these sources. The protein expression, isolation, and purifications are well known to a person having ordinary skill in the art. The Examples demonstrate methods of expression, isolation, and purifications of Bl-Eng2 according to one embodiment of the present invention.

A vaccine comprising a Dectin-2 ligand adjuvant may also comprise other suitable ingredients. In one embodiment, a vaccine may also comprise a carrier molecule as a stabilizer component. As the types of vaccines enclosed in the present invention may be rapidly degraded once injected into the body, the vaccine may be bound to a carrier molecule for stabilizing the vaccine during delivery and administration. A suitable carrier or stabilizer may comprise fusion proteins, polymers, liposomes, micro- or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly(ethylene glycol) (PEG), an animal-based protein, e.g., digested protein extracts such as N-Z-Amine®, N-Z-Amine AS® and N-Z-Amine YT® (Sheffield Products Co., Norwich, N.Y.), a vegetable-based protein, e.g., soy protein, wheat protein, corn gluten, rice protein and hemp protein, and any other suitable carrier molecules.

As used herein "glucan particle" refers to a formulation of the vaccine comprising $\beta_{1,3}$ glucan particles as a solid support. Glucan particles target Dectin-1, a key pattern recognition receptor for anti-fungal immunity. Glucan particles also serve as structural vessels or a type or structural scaffold to deliver antigen as well as adjuvants in the vaccine formulation. In one embodiment, $\beta_{1,3}$ glucan particles (GPs) are used as a solid support for Bl-Eng2. In one embodiment, glucan particles in used in a vaccine formulation with calnexin fragments and a Dectin-2 ligand adjuvant against pathogenic fungi.

In another aspect, the Dectin-2 ligand adjuvant of the present invention may be administered in a formulation with any known commercially available adjuvant in the art. Adjuvants to be administrated may include, but are not limited to, aluminum hydroxide (Alum), glucan particles engaging Dectin-1, Adjuplex, and combinations thereof. It is also envisioned that when Bl-Eng3 is administered in a vaccine composition as an antigen, it may be administrated with a suitable adjuvant. Suitable adjuvants are any commercially available adjuvant known in the art or an adjuvant described herein.

Suitable Carrier or Vehicle

Suitable agents may include a suitable carrier or vehicle for delivery. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the *U.S. Pharmacopeia National Formulary,* 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Stabilization Agent

In another configuration, the present formulation may also comprise other suitable agents that stabilize the formulations. For example, an approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water may also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

An effective method for stabilizing peptides and proteins against solid-state aggregation for delivery may be to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles may be provided within the invention that effectively control water content to enhance protein stability. These reagents and carrier materials effective as anti-aggregation agents in this sense may include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins may also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, may also impart significant physical stability to dry, e.g., lyophilized proteins. These additives may also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation may provide additional advantages within the intranasal delivery methods and compositions of the invention.

Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers may be extended to proteins via the use of peptides and peptide mimetics that similarly block protein aggregation. A wide range of suitable methods and anti-aggregation agents may be available for incorporation within the compositions and procedures of the invention.

Stabilizing Delivery Vehicle, Carrier, Support or Complex-Forming Species

In another embodiment, the present formulation may also comprise other suitable agents such as a stabilizing delivery vehicle, carrier, support or complex-forming species. The coordinate administration methods and combinatorial formulations of the instant invention may optionally incorporate effective lipid or fatty acid based carriers, processing agents, or delivery vehicles, to provide improved formulations for delivery of Dectin-2 ligand or functionally equivalent fragment proteins, analogs and mimetics, and other biologically active agents and antigens of the composition. For example, a variety of formulations and methods are provided for delivery which comprise one or more active agents, including the Dectin-2 ligand adjuvant, such as a peptide or protein, admixed or encapsulated by, or coordinately administered with, a liposome, mixed micellar carrier, or emulsion, to enhance chemical and physical stability and increase the half-life of the biologically active agents (e.g., by reducing susceptibility to proteolysis, chemical modification and/or denaturation) upon mucosal delivery.

Within certain aspects of the invention, specialized delivery systems for biologically active agents may comprise small lipid vesicles known as liposomes or micelles. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

Additional delivery vehicles carrier, support or complex-forming species for use within the invention may include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance delivery of Calnexin or a functionally equivalent fragment, and other biologically active agents disclosed herein. Medium chain fatty acids (C6 to C12) and monoglycerides have also been shown to have enhancing activity in intestinal drug absorption and can be adapted for use within the mucosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

The vaccine formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). The buffer(s) may be added as part of the stabilizer component during the preparation thereof, if desired. Other excipients, if desired, may be included as part of the final vaccine formulation.

The remainder of the vaccine formulation may be an acceptable diluent, to 100%, including water. The vaccine formulation may also be formulated as part of a water-in-oil, or oil-in-water emulsion.

Also provided as part of the invention is a method of preparation of the vaccine formulation described herein. Preparation of the vaccine formulation preferably takes place in two phases. The first phase may typically involve the preparation of the stabilizer component. The stabilizer component may comprise any suitable components as discussed above. For example, a vegetable-based protein stock solution may be prepared by dissolving the vegetable-based protein in a diluent. The preferred diluent may be water, preferably distilled and/or purified so as to remove trace impurities (such as that sold as purified Super Q®). In a separate vessel an animal-based protein may be dissolved in a diluent, additionally with the sugar component and buffer additives. Preferably, an equal volume of the vegetable-based protein stock solution is added to the animal-based protein solution. It is desirable that after HCl/KOH adjustment to achieve a pH of approximately 7.2±0.1, the stabilizer component may be sterilized via autoclave. The stabilizer solution may be refrigerated for an extended period prior to introduction of the Dectin-2 ligand adjuvant and a suitable antigen.

The second phase of preparation of the vaccine formulation may include introduction of the Dectin-2 ligand adjuvant and a suitable antigen with the stabilizer component, thereby yielding the vaccine formulation. Preferably, the Dectin-2 ligand adjuvant may be diluted with a buffer solution prior to its introduction to the stabilizer component.

Once this vaccine formulation solution has been achieved, the formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The term "lyophilization" or "lyophilized," as used herein, refers to freezing of a material at low temperature followed by dehydration by sublimation, usually under a high vacuum. Lyophilization is also known as freeze drying. Many techniques of freezing are known in the art of lyophilization such as tray-freezing, shelf-freezing, spray-freezing, shell-freezing and liquid nitrogen immersion. Each technique will result in a different rate of freezing. Shell-freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray-freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray-freezing into liquid, dropping by ~20 μl droplets into liquid $N_2$, spray-freezing into vapor over liquid, or by other techniques known in the art.

The vaccine of the present invention may be either in a solid form or in a liquid form. Preferably, the vaccine of the present invention may be in a liquid form. The liquid form of the vaccine may have a concentration of 50-4,000 nanomolar (nM), preferably between 50-150 nM. In some embodiments, the concentration will be between 1-50,000 nM.

To vaccinate a patient, a therapeutically effective amount of vaccine comprising a suitable antigen and a Dectin-2 ligand adjuvant may be administered to a patient. The therapeutically effective amount of vaccine may typically be one or more doses, preferably in the range of about 0.01-10 mL, most preferably 0.1-1 mL, containing 1-200 micrograms, most preferably 1-100 micrograms of vaccine formulation/dose. The therapeutically effective amount may also depend on the vaccination species. For example, for smaller animals such as mice, a preferred dosage may be about 0.01-1 mL of a 1-50 microgram solution of antigen. For a human patient, a preferred dosage may be about 0.1-1 mL of a 1-50 microgram solution of antigen. The therapeutically effective amount may also depend on other conditions including characteristics of the patient (age, body weight, gender, health condition, etc.), the species of fungi, and others. In one embodiment the vaccine formulation of the present invention comprises 1-100 micrograms of Dectin-2 ligand adjuvant and 5-20 micrograms of Calnexin fragment in either soluble or glucan particle formulation.

In another aspect, to vaccinate a patient against a fungal infection, a therapeutically effective amount of a vaccine comprising Bl-Eng2 as an antigen may be administered to a patient. The therapeutically effective amount of vaccine my typically be one or more doses, preferably in the range of about 0.01-10 mL, most preferably 0.1-1 mL, containing 1-200 micrograms, most preferably 1-100 micrograms of vaccine formulation/dose. The vaccine my comprise 1-100 micrograms of Bl-Eng2 as an antigen.

A vaccine of the present invention may be administered by using any suitable means as disclosed above. Preferably, a vaccine of the present invention may be administered by intranasal delivery, transmucosal administration, subcutaneous or intramuscular administration, e.g., needle injection. In some embodiments, vaccine compositions for protection against a viral infection are formulated for transmucosal delivery. In some embodiments, vaccine compositions for protection against a bacterial infection are formulated for subcutaneous administration.

After vaccination using a vaccine of the present invention comprising the Dectin-2 ligand adjuvant, a patient may be immunized against at least one type of fungi, bacteria, or virus. In one specific embodiment, a patient after vaccination may be immunized against at least one species of dimorphic fungi. In one preferred embodiment, a patient after vaccination may be immunized from multiple dimorphic fungi including *Histoplasma, Coccidiodes, Paracoccidioides, Penicillium, Blastomyces, Sporothrix*, and *Aspergillus fumigatus*

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains the Bl-Eng2 adjuvant or a functionally equivalent fragment, and/or other biologically active agents in combination with mucosal or subcutaneous delivery enhancing agents disclosed herein formulated in a pharmaceutical preparation for delivery.

As used herein, the term "pharmaceutically acceptable carrier" refers to any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the antigentic peptide, i.e., the calnexin protein may be coated in a material to protect the peptide from the action of acids and other natural conditions that may inactivate the peptide.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The composition can be formulated as a solution, microemulsion, dispersion, liposome, or other ordered structure suitable to high drug concentration.

In one embodiment, the composition may also comprise a carrier molecule as a stabilizer component. As the types of proteins or peptides enclosed in the present invention may be rapidly degraded once injected into the body, the proteins or peptides may be bound to a carrier molecule for stabilizing the proteins or peptides during delivery and administration. A suitable carrier or stabilizer may comprise fusion proteins, polymers, liposome, micro or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly(ethylene glycol) (PEG), an animal-based protein, e.g., digested protein extracts such as N-Z-Amine®, N-Z-Amine AS® and N-Z-Amine YT® (Sheffield Products Co., Norwich, N.Y.), a vegetable-based protein, e.g., soy protein, wheat protein, corn gluten, rice protein and hemp protein, and any other suitable carrier molecules. The composition may also comprise any suitable carrier or vehicle, such as those as discussed above. The composition may also comprise other stabilization agents, such as those as discussed above.

In one embodiment, the composition may also comprise suitable stabilizing delivery vehicle, carrier, support or complex-forming species, such as those as discussed above. For example, the composition may additionally comprise at least one of a stabilizer, a buffer, or an adjuvant.

The present invention has been described in terms of one or more preferred embodiments, and it should be appreciated that many equivalents, alternatives, variations, and modifications, aside from those expressly stated, are possible and within the scope of the invention.

Example 1

Adaptive immunity is critical for the prevention and resolution of fungal infections. The contribution of antibodies to host defense is debated. In contrast, Ag-specific $CD4^+$ T cells play the major role in fungal resistance, as evidenced by the high incidence of life-threatening fungal infections in patients with impaired $CD4^+$ T cells. $CD4^+$ T cells confer resistance by secretion of T-helper 1 (Th1) and Th17 cytokines such as IFN-γ, TNF-α, GM-CSF, and IL-17A, which activate neutrophils, monocytes, macrophages and DCs for fungal clearance. Since $CD4^+$ T cells are germane to host defense against fungi, the challenge is how best to elicit these T cells.

The transition from innate to adaptive immunity is fostered by dendritic cells (DCs). These cells process and present Ag to naïve $CD4^+$ T cells in the context of co-stimulatory factors (e.g. cell surface ligands and cytokines) that provide the combination of signals necessary to induce naive T cell activation and proliferation. During their interactions with DCs, naive T cells also become functionally specialized. Helper T cell polarization occurs as a result of the cytokines produced by DCs: Th1 polarization is associated with DC production of high levels of IL-12p70, and Th17 polarization is associated with DC production of IL-1β and IL-6. While vaccine Ags typically have little impact on the nature of the cytokines produced by DCs, the adjuvant can have a dramatic effect. Alum (aluminum hydroxide), which is the most commonly used adjuvant in current vaccine formulations, suppresses DC production of pro-inflammatory cytokines such as IL-12p70, creating an environment that polarizes T cells towards a Th2 phenotype.

Thus, a major weakness and central challenge in the field of vaccinology is the lack of adjuvants that drive Th1 and/or Th17 polarization and stimulate DCs to produce the appropriate cytokines. Pathways that can differentially activate DC cytokine profiles include toll-like receptors (TLRs), C-type lectin receptors (CLRs), co-stimulatory ligands such as CD40, and cytokine receptors.

C-type lectins are important in fungal recognition by DCs and in inducing anti-fungal Th1 and Th17 responses. Dectin-1 and Dectin-2 induce Th1/Th17 cells in response to *Candida albicans* and *Aspergillus fumigatus* infection. While Dectin-1 is dispensable, Dectin-2 is requisite for the development of protective Th1 and Th17 cells and vaccine resistance against dimorphic fungi. Crude fractions of mannoproteins isolated from *Malassezia pachydermatis* as well as a lipoglycan (Man-LAM) of *Mycobacterium tuberculosis* have been shown to trigger Dectin-2 signaling, however they have not been evaluated as vaccine adjuvants, and glycans and lipids may be difficult to express and scale.

The embodiment described here demonstrates a novel fungal Dectin-2 ligand from an attenuated vaccine strain of *Blastomyces dermatitidis*, Bl-Eng2. We tested whether the ligation of Dectin-2 effectively vaccinates mice against fungi. Our vaccination strategy was to ligate Dectin-2 with Bl-Eng2 and assess the adjuvant activity by combining it with the recently reported pan-fungal vaccine calnexin. Fungal recombinant Bl-Eng2 was expressed and scaled efficiently, it stimulated TL-6 and IL-1β production in vitro and Th1 and Th17 cells in vivo and, when used as an adjuvant in combination with calnexin, it protected mice against pneumonia in a model of lethal pulmonary fungal infection.

Results

Figures 1A, 1B, 1C, 1D, 1E, 1F:
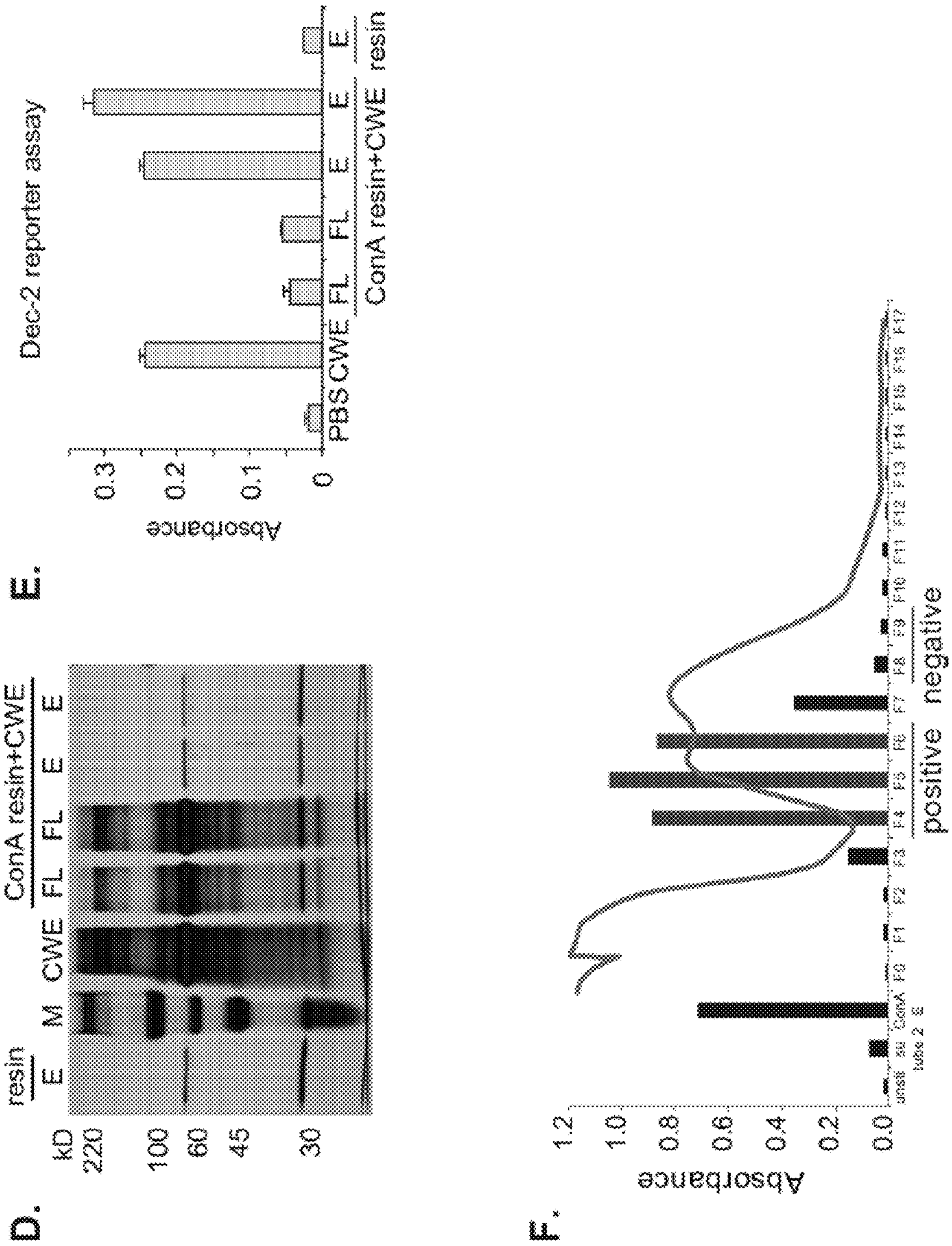
Figures 6A, 6B, 6C:
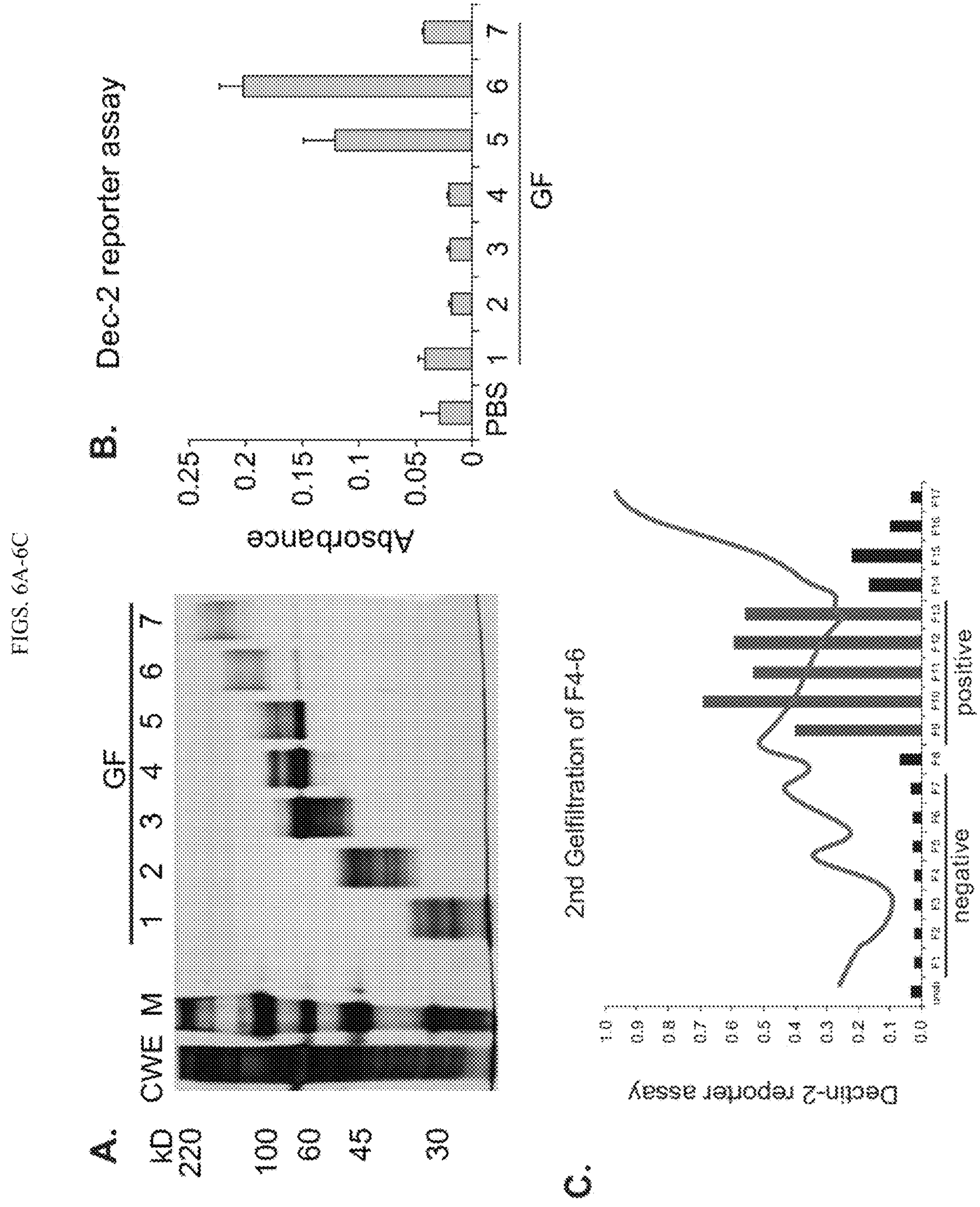
FIGS. 6A-6C show separation, characterization, and enrichment of Dectin-2 ligand activity. (A) 100 μg CWE was fractionated by a GELFREE (GF) 8100 system. The fractions were separated by SDS-PAGE and silver stained. (B) Acetone-precipitated fractions were assayed for ligand activity. (C) Fractions 4-6 from the 1st gel filtration contained most of the ligand activity (see FIG. 1F); they were separated by a second run over the size exclusion column (blue line represents the trace line of $A_{280}$ absorption). Fractions were tested by Dectin-2 reporter cells for ligand activity. Fractions 9-13 contained most of the ligand activity and were determined the positive pool; fractions 1-7 were the negative pool for the subsequent mass spec analysis.

*B. dermatitidis* vaccine yeast are bound by soluble Dectin-2 fusion protein and trigger NFAT signaling of Dectin-2 reporter cells. Dectin-$2^{-/-}$ mice fail to develop Ag-specific Th1 and Th17 cells or acquire vaccine resistance. We therefore sought to identify the fungal pathogen-associated molecular pattern (PAMP) that is recognized by Dectin-2. We used the NFAT-LacZ reporter cells to enrich Dectin-2 ligand activity from the vaccine yeast cell wall. We sonicated vaccine yeast, collected the water-soluble, cell-wall extract (CWE) and analyzed it by SDS-PAGE. CWE displayed a broad range of protein bands (FIG. 1A) and harbored Dectin-2 ligand activity (FIG. 1). Digestion of CWE with proteinase K or endo-mannosidases reduced this activity (FIG. 1*i*), suggesting that both protein and glycan moieties may contribute to ligand activity. To define the Mr of candidate proteins, we separated the CWE using a GEL-FREE 8100 system (FIG. 6A). Fractions #5-6 ranging between 75 to 150 kDa in size contained ligand activity (FIGS. 6A-6B).

Figures 2A, 2B, 2C, 2D:
FIGS. 2A-2D show mass spec analysis identified Bl-Eng2 as a Dectin-2 ligand candidate: (A) The ligand-negative and -positive fractions (#9-13 and #1-7 from FIG. 6C, respectively) from the second gel filtration were analyzed by Mass spectrometry. Numbers on the right represent number of peptide specific fragments detected. (B) Domains of native *B. dermatitidis* Eng2 (Bl-Eng2) and recombinant Bl-Eng2 expressed in *Pichia pastoris*: SP denotes Signal peptide; GH16 denotes glycosyl hydrolase catalytic domain; Ser/Thr-rich domain harbors 68 potential O-linked glycosylation sites; and Myc and His tags are placed at the C terminus for purification. (C) 0.6 μg Bl-Eng2 and 0.3 μg PDIA1 were run on SDS-PAGE gel under reducing conditions and stained for protein (left) or carbohydrate (right). (D) Monosaccharide composition of Bl-Eng2 measured by gas chromatography (GC). GC chromatogram of the alditol acetate-derivatized monosugars of hydrolyzed Bl-Eng2 (top). Monosaccharides are labeled as follows: Rha—rhamnose, Rib—ribose, Xyl—xylose, Man—mannose, and Glu—glucose. Unlabeled peak at 5.953 min resulted from component degradation during alditol acetate derivatization. Pie diagram shows the relative contribution of monosaccharides (bottom).
Figures 2A, 2B, 2C, 2D:
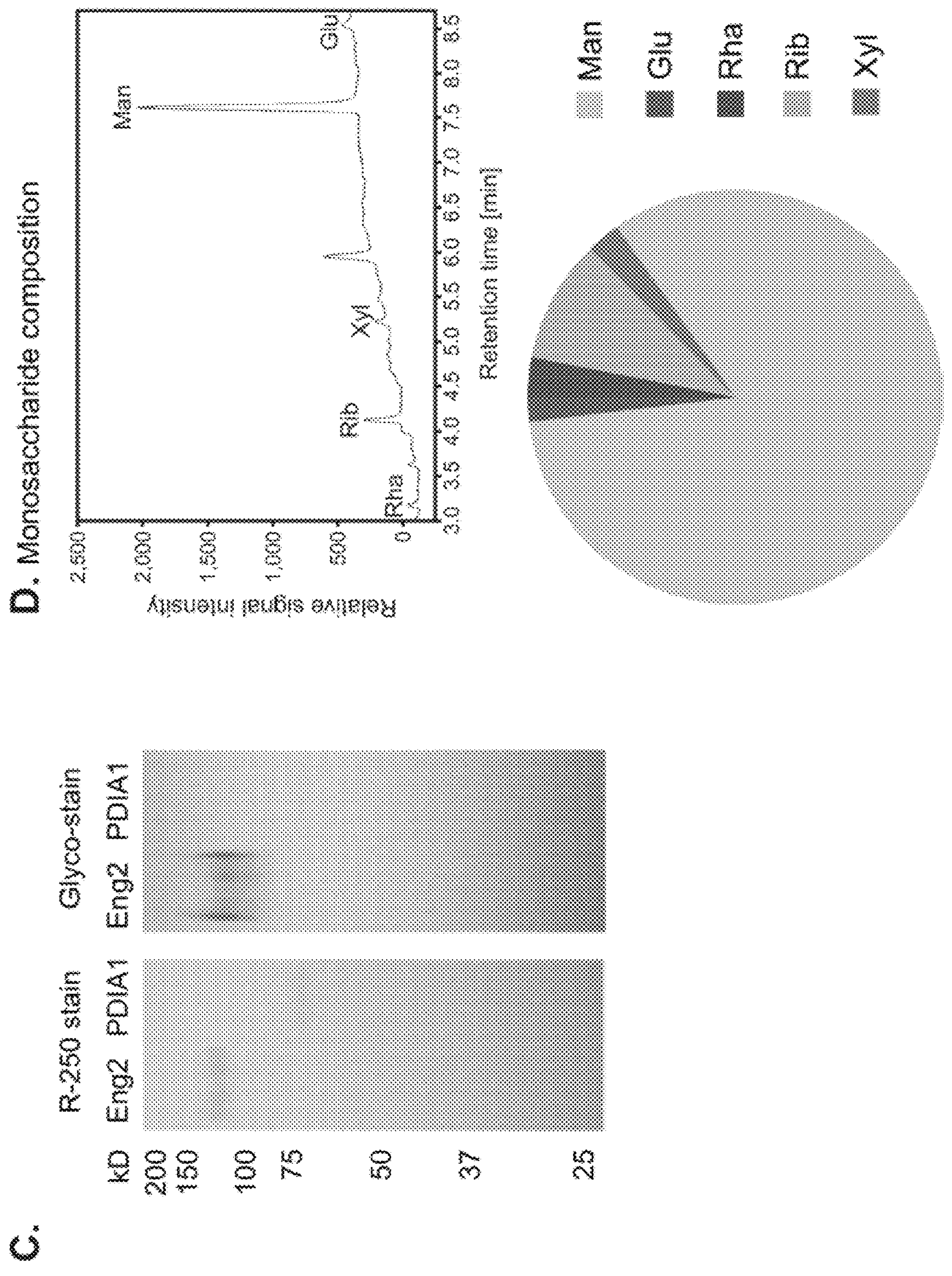

To enrich and identify glycoprotein with ligand activity, we employed the lectin Concanavalin A (ConA), which binds α-D-mannose and α-D-glucose moieties, gel filtration and Mass spectrometry analysis (FIG. 1C). The majority of the ligand activity was removed from CWE by a ConA resin, and the eluate was highly enriched for ligand activity (FIGS. 1D-1E). The enrichment by ConA suggested that the Dectin-2 ligand(s) in CWE are mannoproteins. To further enrich ligand activity, the ConA eluate was separated by size exclusion chromatography twice, sequentially. Fractions F4-F6 after the first run contained ligand activity as determined by the Dectin-2 reporter assay (FIG. 1F); F4-6 were pooled and subjected to a second separation by gel filtration. The positive fractions (F9-F13) and negative ones (F1-F7) after the second gel filtration (FIG. 6C) were analyzed by mass spectrometry (FIGS. 2A and 7A). Proteins that were more abundant in the positive vs. negative fraction were considered candidates. Among the candidates, an uncharacterized member (BDFG_08749) of the fungal endo-1,3(4)-β-D-glucanase family stood out in positive fractions (FIG. 7A). The native 526-aa protein contains an 18-aa signal peptide, an N-terminal GH16 glycosyl hydrolase (GH) catalytic domain, and a C-terminal S/T-rich domain (FIGS. 2B and 7B) that could be responsible for the strong glycosylation (FIGS. 2C-2D). The GH16 catalytic domain of the endo glucanase has 60.1% similarity (identical aa and conservative substitution) (45.8% identity) and the entire glycoprotein has 45.2% similarity (28.8% identity) to the GPI-anchored endo β-1,3-glucanase Eng2 of *A. fumigatus*. Thus, we named the protein ligand *Blastomyces*-Eng2 (Bl-Eng2). PDIA1 is a protein that was more abundant in the negative gel filtration fraction (e.g. a negative control) (FIG. 2A) and showed no reporter activity and little glycosylation (FIG. 2C).

Bl-Eng2 protein is a bona-fide ligand for Dectin-2—To evaluate whether Bl-Eng2 is recognized by Dectin-2, we cloned and expressed the recombinant protein in *Pichia pastoris*. This eukaryotic expression system modifies recombinant proteins with both O- and N-linked glycosylation. Full-length Bl-Eng2 was fused to a N-terminal α-factor secretion signal and a C-terminal Myc-6×His tag (FIG. 2B). Ni-NTA purified Bl-Eng2 showed a band of ~120 kDa on SDS-PAGE gel (FIG. 2C), which falls within the size range determined in FIG. 6A+B. Periodic acid-Schiff (PAS) based glyco-stain of Bl-Eng2 showed strong glycosylation (FIG. 2C), which likely accounts for the discrepancy between predicted Mr of 57 kDa and apparent Mr of ~120 kDa. Gas chromatography (GC) analysis indicated that mannose is the major monosaccharide, and constitutes 82.8% in glycan mass of *Pichia*-expressed Bl-Eng2 (FIG. 2D).

To verify Bl-Eng2 ligand activity, B3Z reporter cells expressing Dectin-2 or other distinct CLRs were incubated with recombinant Bl-Eng2. Bl-Eng2 elicited strong NFAT-lacZ signalling from Dectin-2 reporter cells, but not from the other CLR-expressing cells (FIG. 3A), indicating a specific interaction between Dectin-2 and Bl-Eng2. Since *Aspergillus* Eng2 (Asp-Eng2) exhibits a high degree of similarity to Bl-Eng2 and contains a Ser/Thr-rich C terminus, we also tested whether Asp-Eng2 is recognized by Dectin-2. Asp-Eng2 and Bl-Eng2 were similarly recognized by Dectin-2 expressing reporter cells (FIGS. 8A-8B), hence Eng2 from both fungal species are Dectin-2 ligands.

Dectin-2 is required for Bl-Eng2 ligand activity in primary cells—To investigate whether Bl-Eng2 stimulates primary cells, we examined pro-inflammatory cytokine production from bone marrow-derived dendritic cells (BMDCs). BMDCs from wild type mice, but not Dectin-$2^{-/-}$ or Card$9^{-/-}$ mice, produced a strong IL-6 response when stimulated with recombinant Bl-Eng2, but not PDIA1 (FIG. 3B), indicating ligand specificity for Dectin-2. Lack of stimulation of BMDCs from knockout mice also excludes the possibility of endotoxin contamination as the stimulus of IL-6 in wild type cells. Thus, *Pichia*-expressed Bl-Eng2 triggers a cytokine response in vitro that requires Dectin-2 and downstream Card9. These results together indicate that Bl-Eng2 appears to be a selective Dectin-2 ligand.

Bl-Eng2 is a Dectin-2 ligand with superior capacity to elicit cytokine responses—Dectin-2 recognizes several fungi including *C. albicans, A. fumigatus* and *Malassezia*, which possess N- and O-linked mannan on their surface.

Figures 8A, 8B, 8C, 8D:
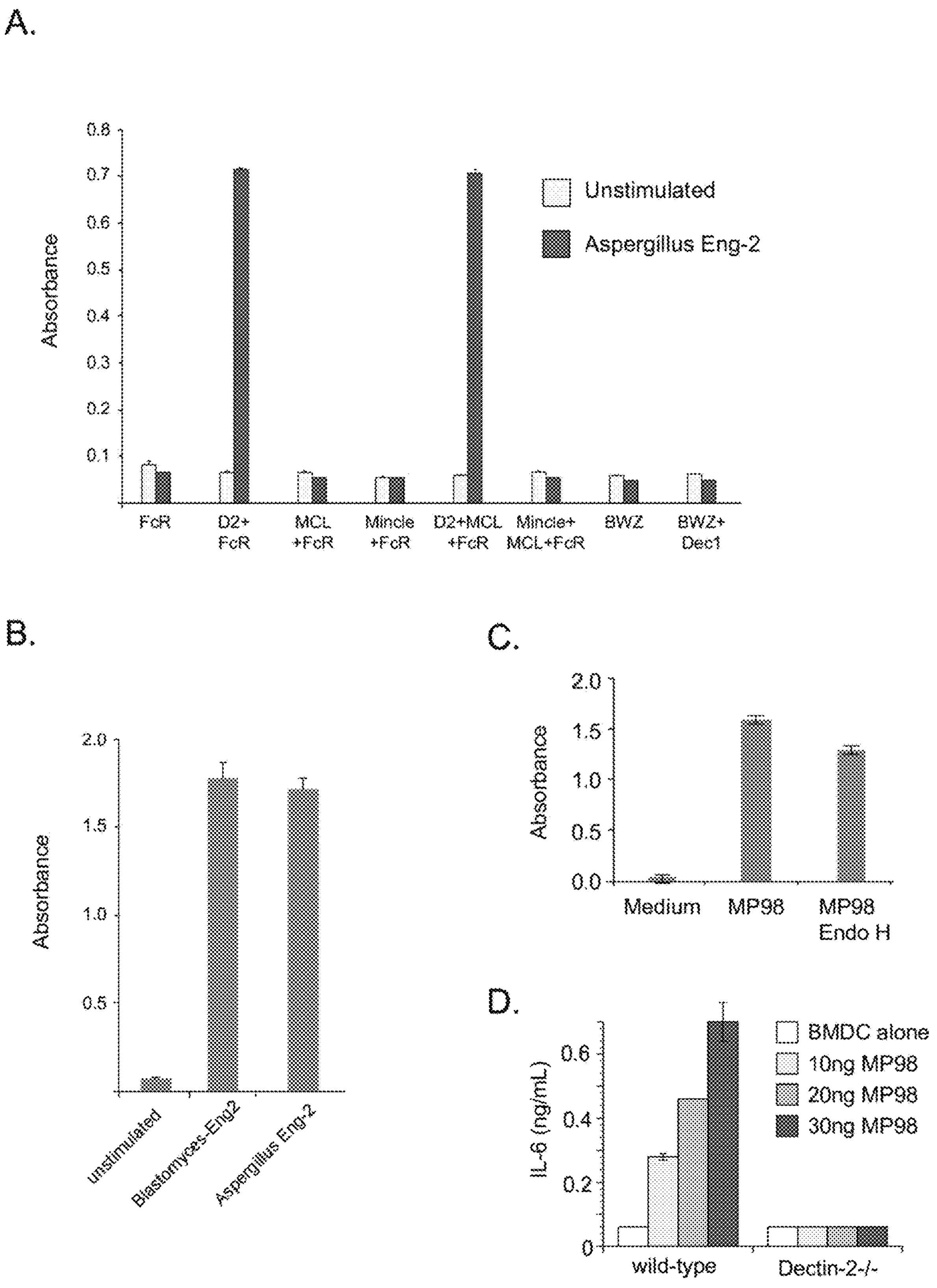
FIGS. 8A-8D demonstrate that *Aspergillus* Eng2 is a Dectin-2 ligand. (A) 0.6 ug *Pichia*-expressed *Aspergillus* Eng-2 was plate-coated and tested for ligand activity using CLR expressing B3Z and BWZ reporter cells. (B) 30 ng plate-coated *Pichia*-expressed *Blastomyces* Eng2 and *Aspergillus* Eng2 was tested for ligand activity with Dectin-2 expressing B3Z reporter cells. (C) 30 ng plate-coated *Pichia*-expressed *Cryptococcus* Eng2 was tested for ligand activity with Dectin-2 expressing B3Z reporter cells. (D) Supernatants from BMDCs ($2\times10^5$ per well) co-cultured with plate-coated MP98 were analyzed for IL-6 by ELISA.

Thus, not surprisingly, there are two other Dectin-2 ligands described in the literature. They are Furfurman from *Malassezia* spp. and Man-LAM from *M. tuberculosis*. In addition to these ligands, by using B3Z reporter cells in the work here, we observed that MP98 from *Cryptococcus neoformans* is also recognized by Dectin-2 (FIG. 8C). MP98 also triggers IL-6 by BMDC in a Dectin-2- and concentration-dependent manner (FIG. 8D). MP98 is a mannoprotein of Mr of 98 kDa with 103 Ser/Thr residues at the C-terminus that serve as potential O-linked glycosylation sites, and 12 putative N-linked glycosylation sites.

Figures 3A, 3B, 3C, 3D:
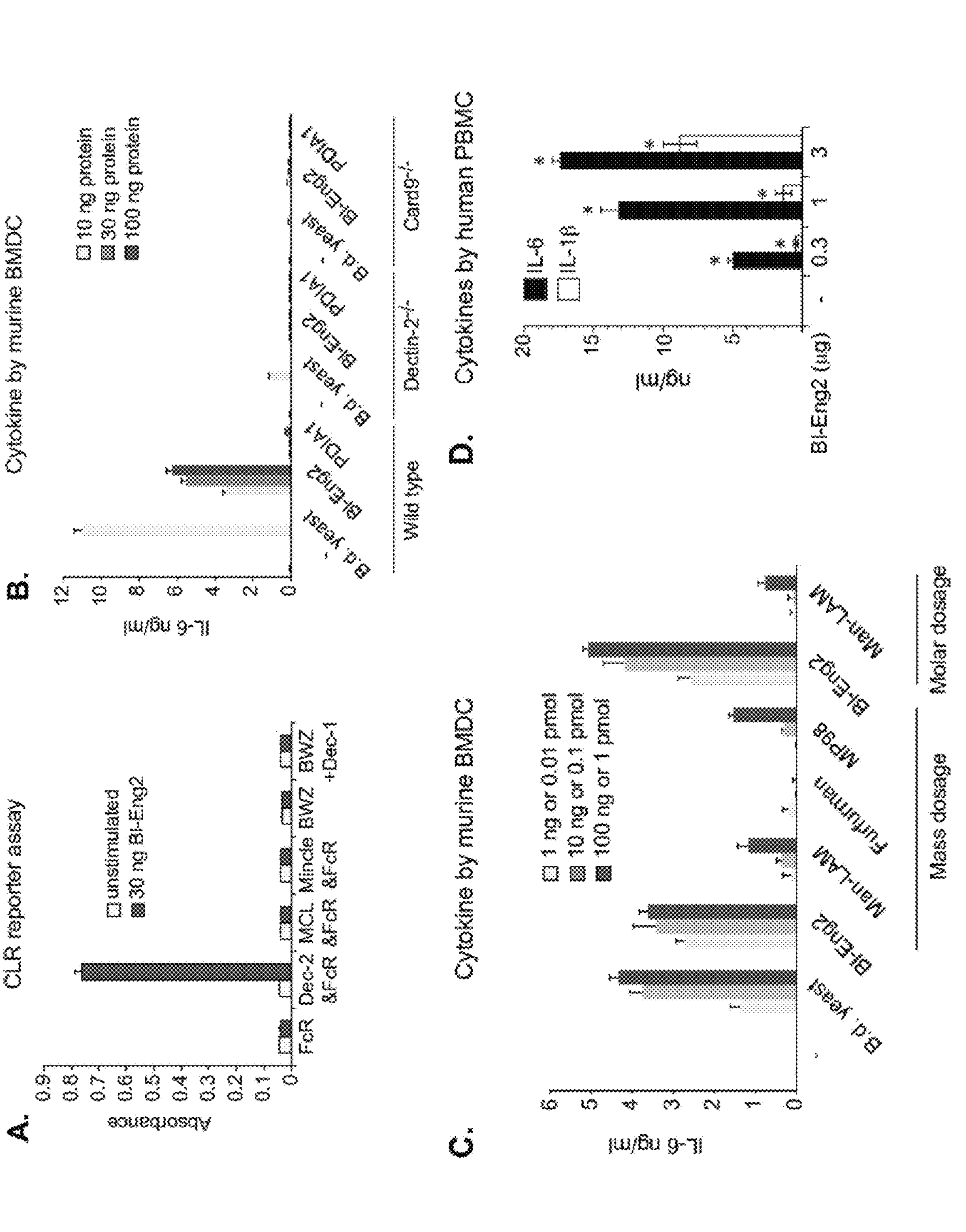
FIGS. 3A-3D demonstrate that Bl-Eng2 is a bona-fide, superior Dectin-2 ligand. (A) *Pichia*-expressed proteins were plate-bound and tested for ligand activity using CLR expressing B3Z reporter cells expressing FcRγ chain, Dectin-2+FcRγ, MCL+FcRγ, and Mincle+FcRγ, and BWZ cells and a subline expressing Dectin-1-CD3ζ (Dectin-1). (B) Supernatants from murine BMDCs ($2\times10^5$ per well) co-cultured with plate-bound Bl-Eng2 or PDIA1 were analyzed for IL-6 by ELISA. *Blastomyces* vaccine yeast ($4\times10^5$ per well) was used as a positive control. (C) Supernatants from BMDCs ($10^5$ per well) co-cultured with 1, 10, or 100 ng and 0.01, 0.1 or 1 pmol plate-bound Bl-Eng2, Man-LAM, Furfurman or MP98 were analyzed for IL-6 by ELISA. *Blastomyces* vaccine yeast ($10^4$, $10^5$ or $10^6$ per well) was used as positive control. Data in A-C represent the mean±SEM of one representative experiment of 3 independent experiments. (D) Bl-Eng2 induces IL-6 and IL-1β by human PBMCs. Human PBMCs were stimulated with plate-bound Bl-Eng2 for 24 h and cytokines in cell culture supernatants were measured by ELISA. Data represent the mean±SEM of 5 healthy individuals. *, $p<0.05$ vs. no Bl-Eng2.

To begin to evaluate the relative potency of Dectin-2 ligands, we compared the ability of Bl-Eng2 and the other three Dectin-2 ligands to induce cytokine production by BMDCs. Bl-Eng2 induced the strongest IL-6 production by BMDCs when compared at equal molar and mass ratios to the other ligands (FIG. 3C). These results suggest that Bl-Eng2 is relatively potent for triggering IL-6 and might be used as an adjuvant for vaccination to boost the development of Ag-specific T cell responses.

Bl-Eng2 induces the production of IL-6 and IL-1β by human PBMCs—A suitable adjuvant for vaccine formulation should ideally stimulate human accessory cells. To test this capacity, we assessed the effect of Bl-Eng2 on the function of human PBMCs. After stimulation with plate-coated Bl-Eng2, human PBMCs from five healthy subjects produced up to 17 ng/ml IL-6 and 9 ng/ml IL-1β as measured in the cell culture supernatants by ELISA (FIG. 3D). These data suggest that recombinant Bl-Eng2 has the capacity to induce the production of Th17 cell priming cytokines by human antigen-presenting cells (APC) in vitro.

Figures 4A, 4B, 4C, 4D, 4E, 4F:
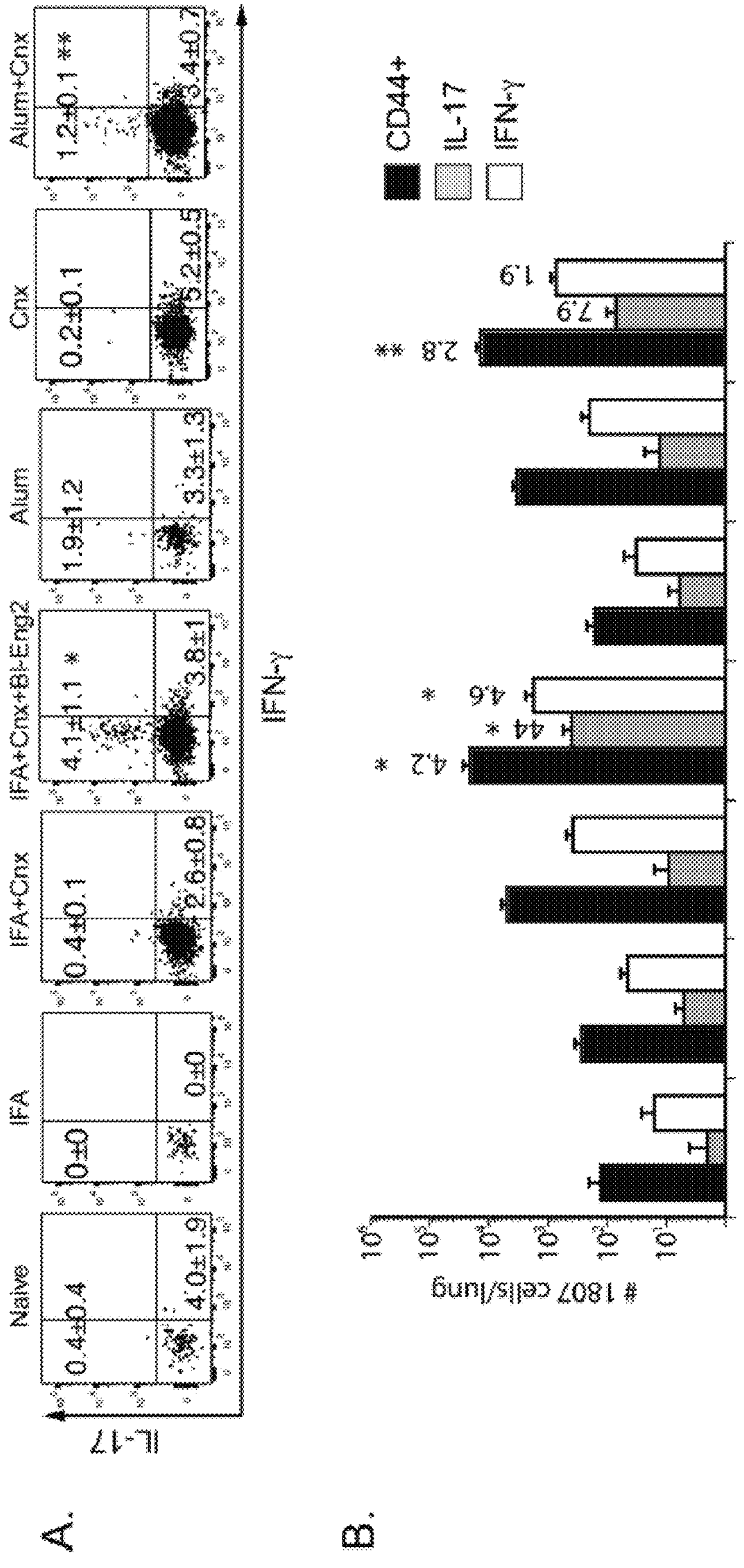
FIGS. 4A-4F show Bl-Eng2 augments $CD4^+$ T cell development in vivo. Mice received $10^6$ adoptively transferred naïve 1807 T cells prior to vaccination (A-D) or no transfer (E+F). Mice were subcutaneously vaccinated with 5 μg calnexin and 10 μg Bl-Eng2 or alum twice, two weeks apart, and then challenged intratracheally with *B. dermatitidis* 26199 yeast two weeks post-vaccination. At day 4 post-infection, the frequencies of IL-17 and IFN-γ producing 1807 T cells (A) and the numbers of activated ($CD44^+$) and cytokine-producing 1807 cells in the lung were enumerated by FACS (B). Almost all of the 1807 T cells recruited to the lung were $CD44^+$. Data represent the average±SEM of two independent experiments with 8-10 mice/group. *, $p<0.05$ vs. control mice vaccinated with calnexin and IFA alone and **, $p<0.05$ vs. control mice vaccinated with soluble calnexin alone. Cytokines from lymph node cells stimulated ex vivo with calnexin were measured by ELISA (D). The number indicates the n-fold change of mice vaccinated with calnexin+Bl-Eng2 vs. mice vaccinated with calnexin alone. *, p<vs. all other groups. Lung CFU were counted at day 18 post-infection when naïve mice were moribund, (C+E). *, $p<0.05$ vs. all other groups. Numbers reflect the n-fold change in lung CFU of mice vaccinated with calnexin and Bl-Eng2 vs. control mice vaccinated with calnexin or IFA alone. The survival of vaccinated mice was recorded for 30 days post-infection (FIG. 4E). *, $p<0.05$ vs. all other groups. At day 4 post-infection, the number of calnexin-specific $CD4^+$ T cells was enumerated by tetramer staining (FIG. 4F). Data represent the average±SEM of tetramer positive cells from one of two independent experiments with 4-5 mice/group. *, $p<0.05$ vs. all other groups. Cnx denotes calnexin.
Figures 4A, 4B, 4C, 4D, 4E, 4F:
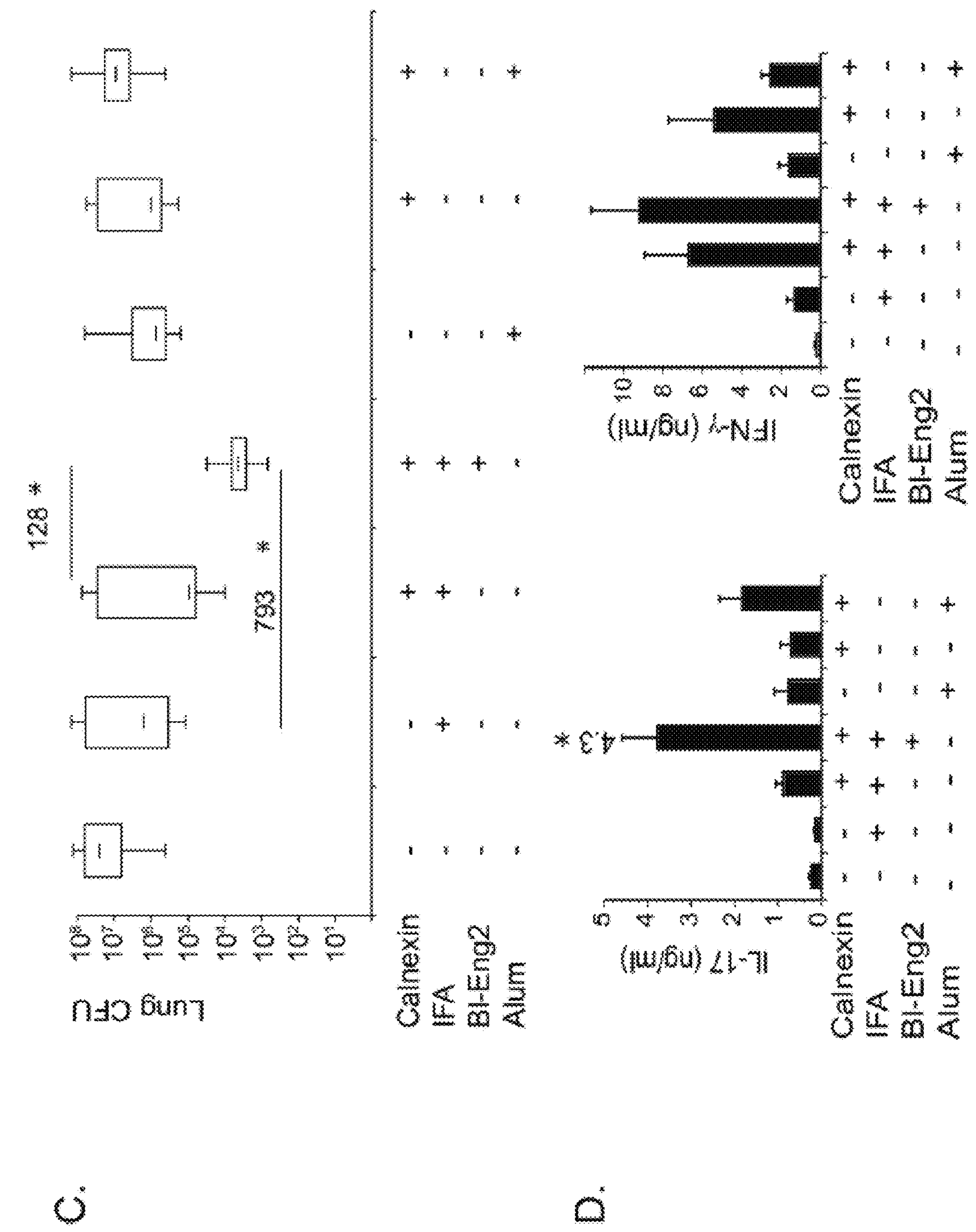
Figures 4A, 4B, 4C, 4D, 4E, 4F:
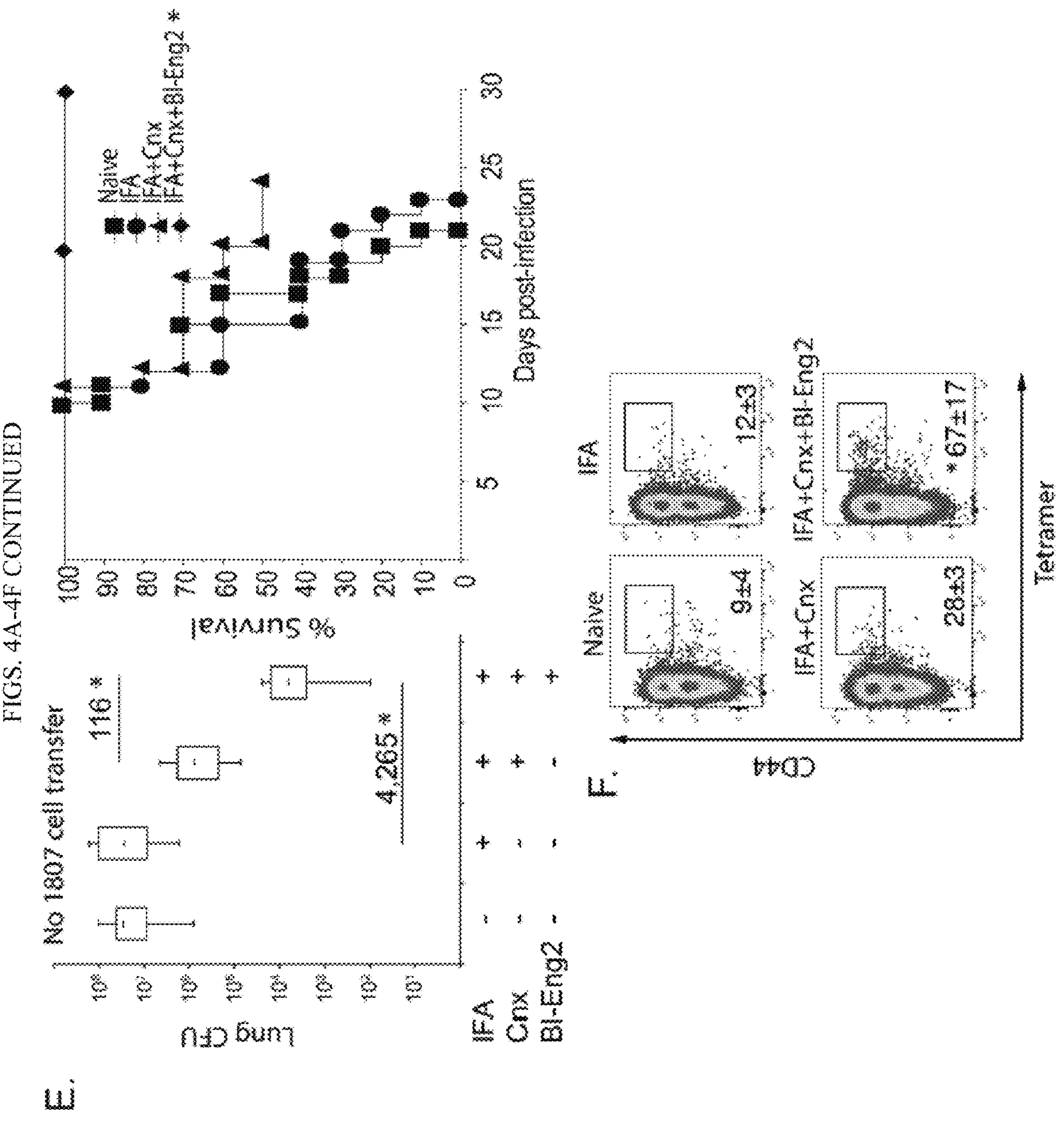
Figures 9A, 9B, 9C, 9D, 9E:
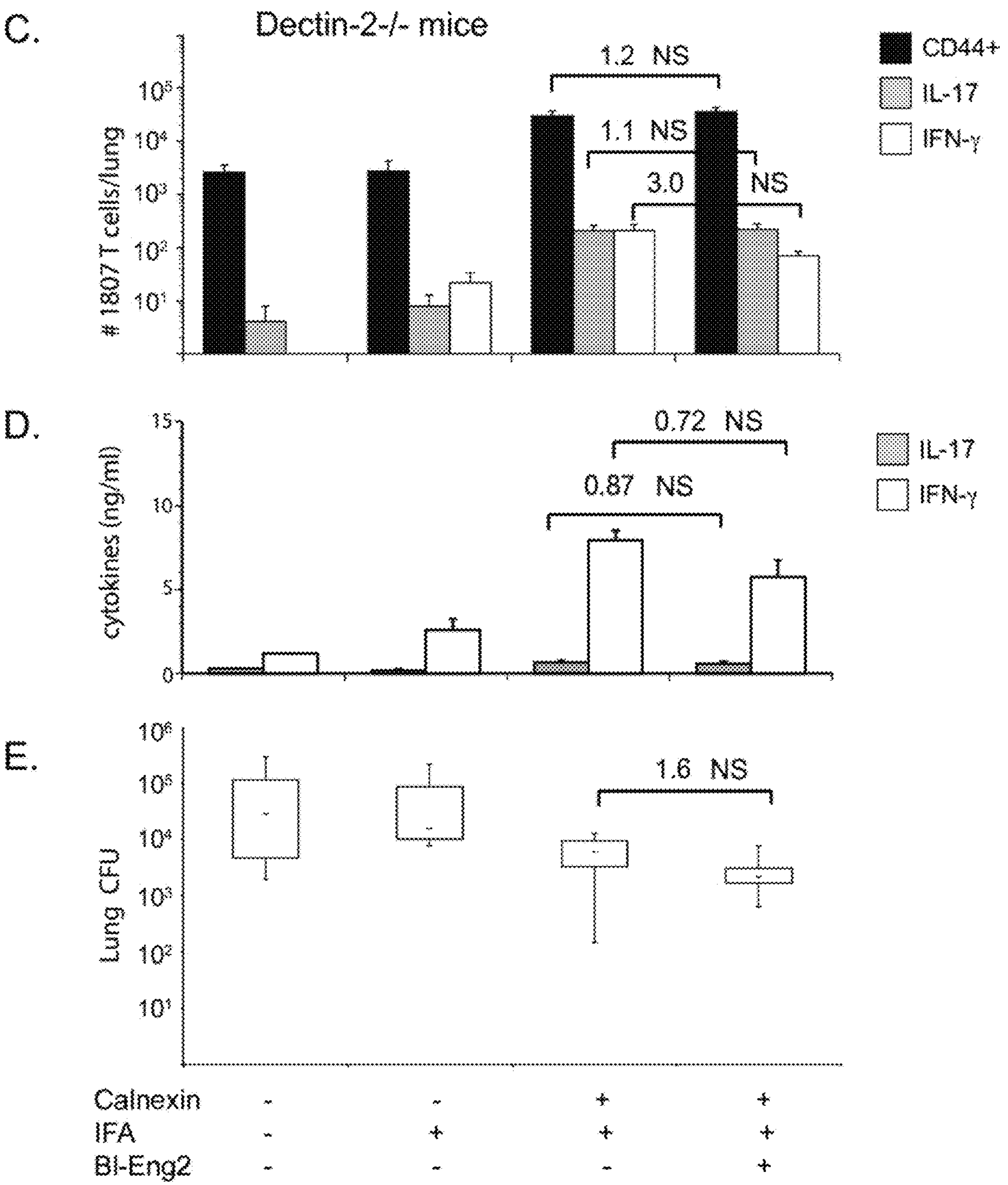
FIGS. 9A-9E demonstrate that Bl-Eng2 induces the development of Th17 and Th1 cells in a Dectin-2 dependent manner and reduces lung CFU concentration dependently. (A+C) Mice were subcutaneously vaccinated twice with calnexin and Bl-Eng2, two weeks apart and challenged intratracheally with *B. dermatitidis* 26199 yeast two weeks post-vaccination. At day 4 post-infection, the numbers of activated ($CD44^+$) and cytokine producing 1807 T cells in wild type (A) and Dectin-$2^{-/-}$ mice (C) were enumerated by FACS. Data represent the average±SEM of 5 mice/group. *, $p<0.05$ vs calnexin-vaccinated control mice. Lymph node (LN) cells from the draining brachial LN were stimulated ex vivo with calnexin and cytokines in the cell culture supernatants were measured by ELISA (D). (B+E) At day 4 post-infection, lung CFU of (B) wild type mice and (E) Dectin-$2^{-/-}$ mice were determined by plating lung homogenates. *, $p<0.05$ vs calnexin-vaccinated control mice. (A-E) Numbers reflect the n-fold change of mice vaccinated with calnexin and Bl-Eng2 vs. control mice vaccinated with calnexin. NS; not statistically significant.

Bl-Eng2 promotes T cell development in vivo and imparts vaccine efficacy—To investigate whether Bl-Eng2 could be harnessed as a vaccine adjuvant, we performed preclinical studies in mice. We first tested whether Bl-Eng2 augments the development of vaccine Ag-specific T cells. To assess these T cell responses in vivo, we vaccinated mice with the pan-fungal Ag calnexin and enumerated $CD4^+$ T cell responses by TCR Tg 1807 cells, which are specific for calnexin. Calnexin was suspended with incomplete freund's adjuvant (mineral oil) and injected subcutaneously. The addition of Bl-Eng2 into the formulation sharply increased the frequency of IL-17 producing 1807 T cells (FIG. 4A) and the number of activated ($CD44^+$) and IL-17 and IFN-γ producing 1807 T cells, as measured by ex vivo stimulation with anti-CD3 and anti-CD28 mAb (FIGS. 4B and 9A). Ex vivo stimulation with the vaccine Ag calnexin also yielded sharp increases in the amount of IL-17 produced by T cells from the draining lymph nodes (FIG. 4D). Thus, Bl-Eng2 promoted the development of Th17 cells more so than Th1 cells.

Figures 10A, 10B, 10C:
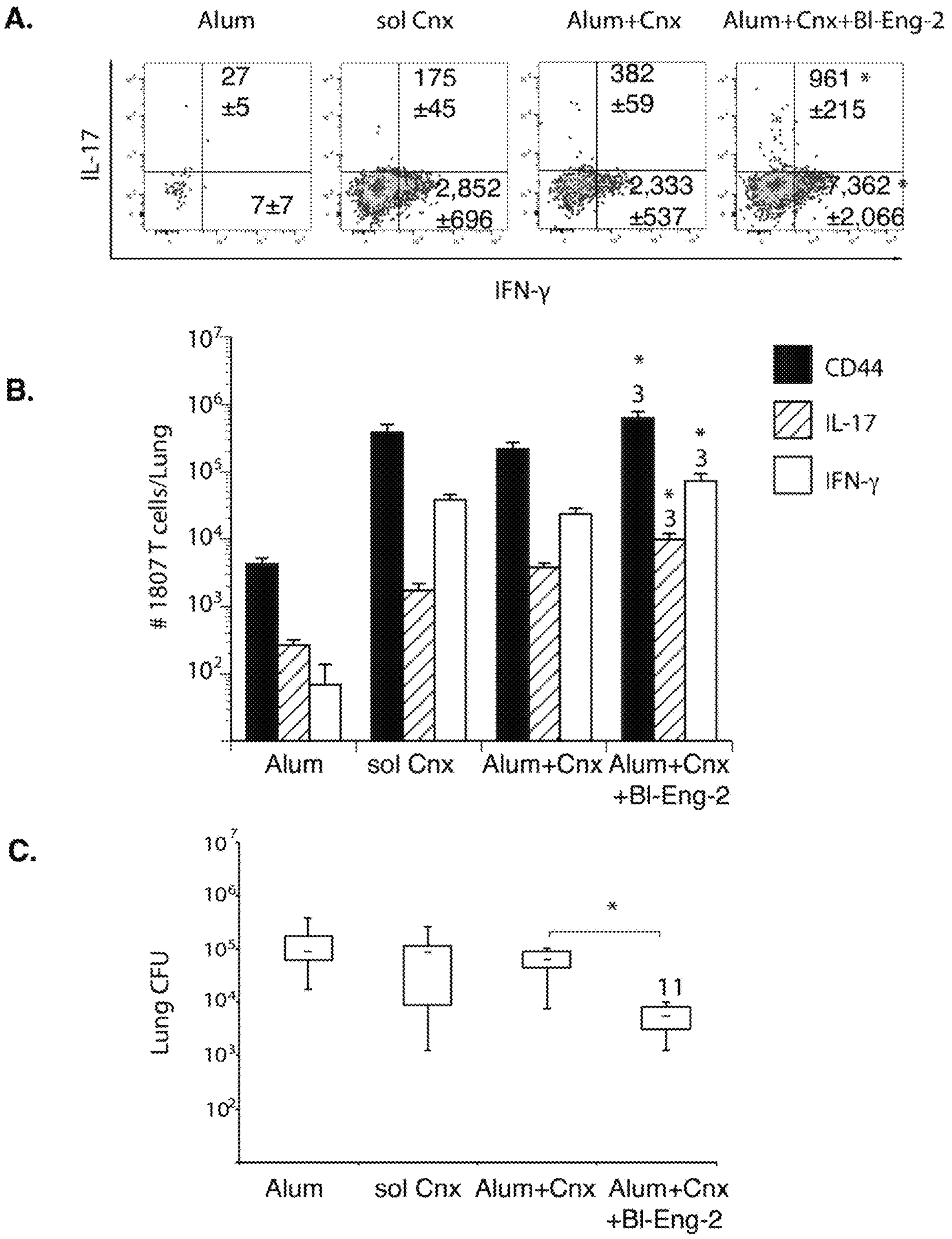
FIGS. 10A-10C show that Bl-Eng2 augments adjuvancy of Alum. (A-C) Mice were subcutaneously vaccinated with 5 μg calnexin and 10 μg Bl-Eng2 or/and alum twice, two weeks apart, and then challenged intratracheally with *B. dermatitidis* 26199 yeast two weeks post-vaccination. At day 4 post-infection, the numbers of activated ($CD44^+$) and cytokine-producing 1807 cells in the lung were enumerated by FACS (A+B). Data represent the average±SEM of 5 mice/group. *, $p<0.05$ vs. control mice vaccinated with calnexin and Alum. The numbers indicate the n-fold change of mice vaccinated with Alum+calnexin+Bl-Eng2 vs. mice vaccinated with Alum+calnexin. *, p<vs. all other groups. Lung CFU were counted at day 4 post-infection (C). The numbers indicate the n-fold change in lung CFU of mice vaccinated with Alum+calnexin+Bl-Eng2 vs. mice vaccinated with Alum+calnexin. *, $p<0.05$ vs. all other groups. Cnx denotes calnexin.

Addition of Bl-Eng2 to the vaccine also reduced lung CFU as early as four days after mice received a lethal experimental challenge, and did so in a concentration-dependent manner (FIG. 9B). In a parallel group, at the time unvaccinated control mice were moribund (day 18 post-infection), the addition of Bl-Eng2 to the vaccine reduced lung CFU by more than two logs (FIG. 4C). Combining the vaccine with commercial alum as an adjuvant did not increase the frequency and numbers of cytokine producing T cells or reduce the fungal burden (FIGS. 4A-4D). However, combining Bl-Eng-2 together with Alum increased the adjuvancy of Alum as measured by the number of activated ($CD44^+$), IL-17 and IFN-γ producing 1807 T cells and the reduction in lung CFU (FIG. 10). These results suggest that Bl-Eng-2 can work in concert with other (commercially available and FDA approved) adjuvants and augment vaccine efficacy.

Bl-Eng2 failed to increase the development of Th17 and Th1 cells, the production ex vivo of IL-17 and IFN-γ or reduce lung CFU in Dectin-$2^{-/-}$ mice, verifying that the adjuvant effect is Dectin-2-dependent in vivo (FIGS. 9C-9E). Thus, Bl-Eng2 exhibits adjuvant-like properties by increasing the development of Ag-specific (1807) Th17 and Th1 cells and protecting mice from lethal pulmonary infection with *B. dermatitidis*.

The studies above exploited TCR Tg T cells to sensitively report the ability of Bl-Eng2 to enhance development of calnexin Ag-specific Th17 and Th1 cells upon vaccination. However, adoptive transfer of these cells into mice artificially enhances the number of $CD4^+$ T cell precursors in the animal. To investigate whether Bl-Eng2 also has the capacity to induce the development of endogenous calnexin-Ag specific $CD4^+$ T cells and similarly protect animals, we vaccinated wild type mice in the absence of adoptive transfer. The formulation of Bl-Eng2 with the calnexin subunit vaccine again reduced lung CFU by over two logs vs. control mice vaccinated with calnexin in mineral oil alone (IFA), and by over 3 logs vs. mice that got IFA alone (FIG. 4E). The addition of Bl-Eng2 to the calnexin vaccine formulation also increased survival significantly vs. control mice vaccinated with calnexin alone (FIG. 4E). This is remarkable since the number of Ag-specific T cell precursors before vaccination was far lower in the absence than in the presence of transferred of naïve 1807 cells, indicating that Bl-Eng2 is a powerful adjuvant that drives the development of protective endogenous calnexin-specific $CD4^+$ T cells (FIG. 4F).

Figures 5A, 5B, 5C, 5D, 5E:
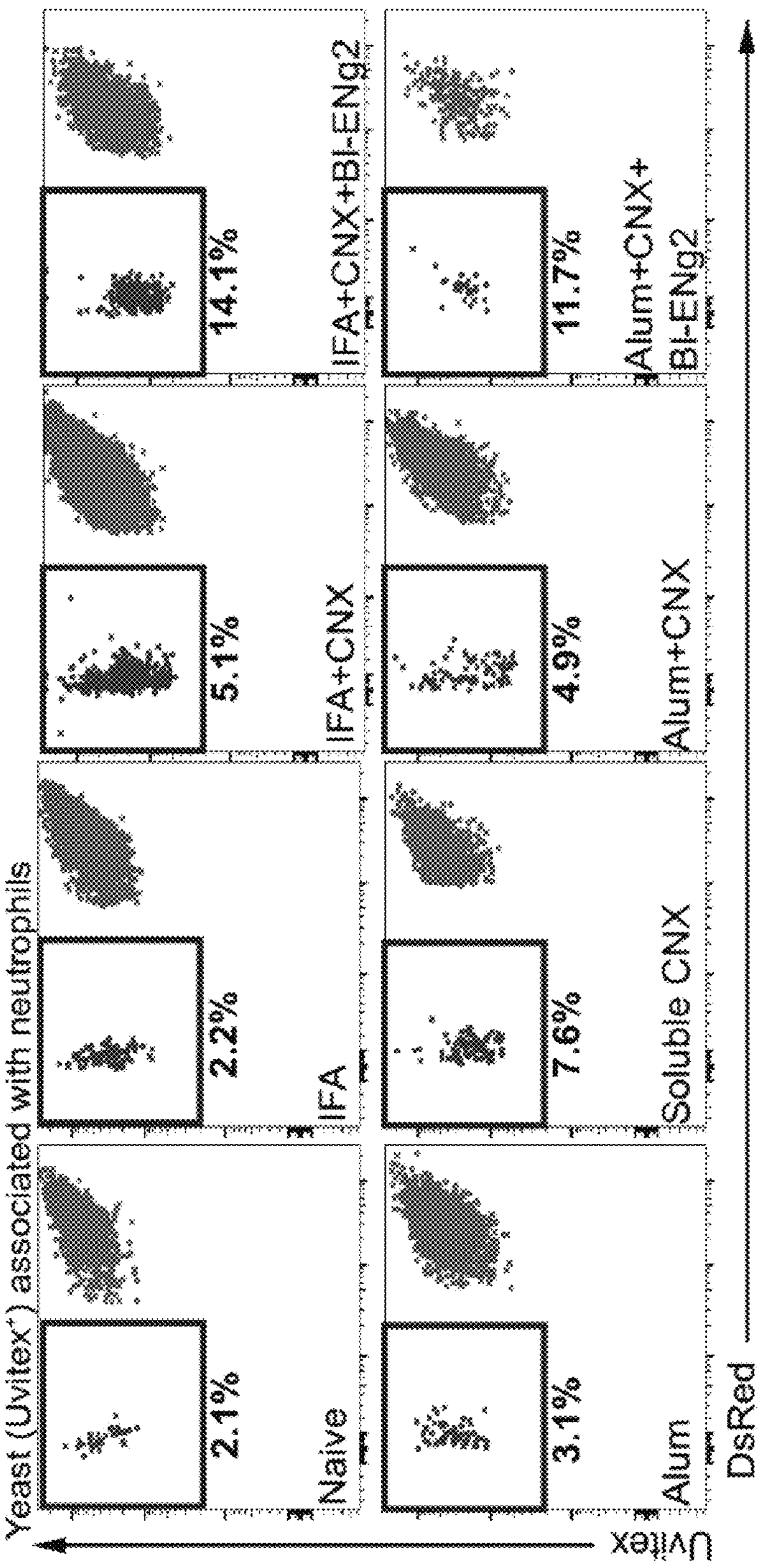
FIGS. 5A-5E show myeloid effector mechanisms by Bl-Eng-2. Mice received 1807 cells prior to vaccination and were vaccinated and boosted with indicated adjuvants and formulated calnexin. Two weeks after the boost, mice were challenged i.t. with $10^5$ DsRed yeast and lungs were harvested 3 days later. The percentage of dead ($DsRed^-Uvitex^+$)(blue) yeast among total neutrophil-associated yeast (all $Uvitex^+$ events)(blue and red together) (see gating strategy in FIG. 11A) were analyzed and calculated (dot plots are concatenates from 5 mice/group) to depict the amount of killing by neutrophils (A+B). The percentage of killing by alveolar macrophages is shown in (C). The number of live yeast was depicted by showing the total number of $DsRed^+$ events (D) or plating lung CFU (E). The numbers indicate the n-fold reduction in live yeast ($DsRed^+$ or CFU) vs. the calnexin control groups. *$p<0.05$ control groups without Bl-Eng-2. Cnx denotes calnexin.
Figures 5A, 5B, 5C, 5D, 5E:
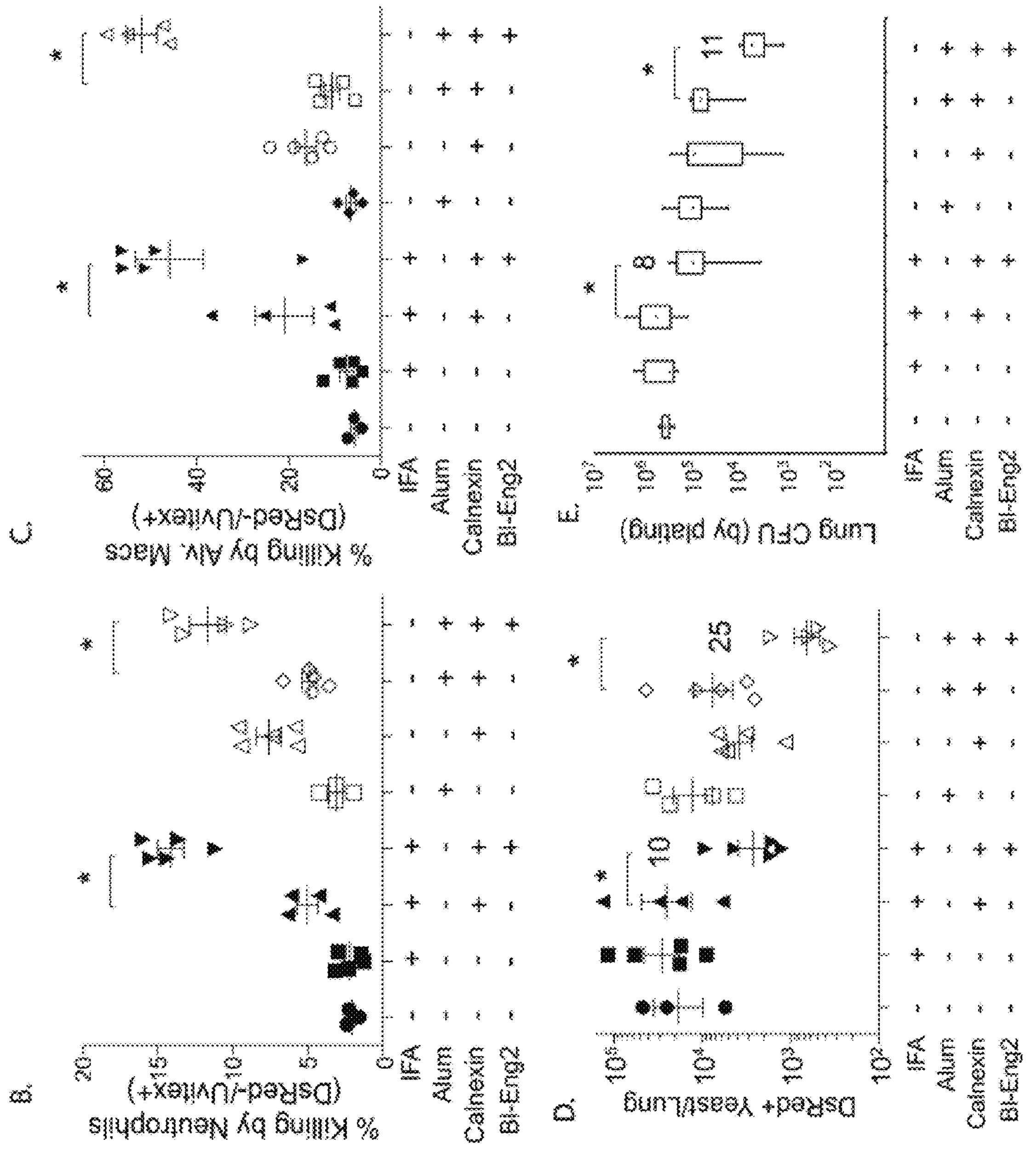
Figures 11A, 11B, 11C, 11D:
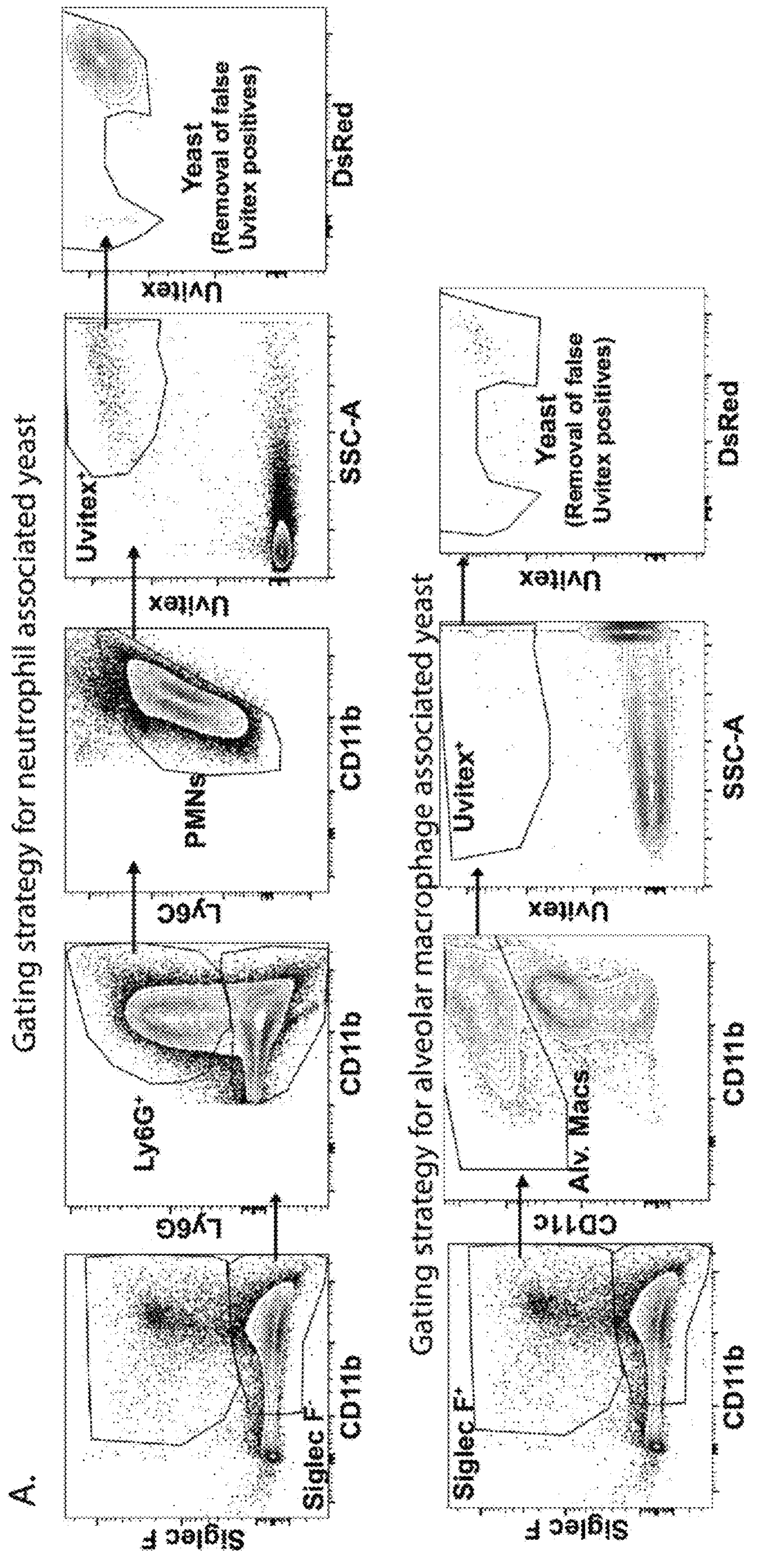
FIGS. 11A-11D demonstrate gating strategy for tracking neutrophil- and alveolar macrophage-associated with yeast, activation of PMN and myeloid effector killing in the absence of 1807 T cell transfer. Viable cells (negative for fixable live/dead dye) that were Siglec $F^-$, $CD11b^+$, $Ly6G^+$ and $Ly6C^{int}$ gated as neutrophils (PMNs) and $SiglecF^+$, $CD11c^+$ gated as alveolar macrophages (A). *Blastomyces* yeast have higher side scatter than most leukocytes, so $Uvitex^+$, $SSC^{hi}$ neutrophils are associated with yeast. Phagocytes in the lungs that have phagocytosed inhaled chitin (from bedding/food) stain with Uvitex when cells are permeabilized. The cells that have phagocytosed chitin/cellulose have decreased Uvitex fluorescence but tend to be autofluorescent in many channels including DsRed; an additional gate was placed on $Uvitex^+$ events to remove any false positives in the neutrophil gate. Activated ($CD11b^{hi}$) neutrophils from the neutrophil gate were calculated and shown in panel (B). Myeloid effector killing in the absence of 1807 T cells (C+D). Mice did not receive adoptive transfer of 1807 cells prior to vaccination and were vaccinated twice with calnexin+/−Bl-Eng-2 emulsified in IFA. Two weeks after the boost, mice were challenged i.t. with $10^5$ DsRed yeast and lungs were harvested 3 days later. The percentage of dead ($DsRed^-Uvitex^+$)(blue) among total neutrophil- or macrophage-associated yeast (all $Uvitex^+$ events)(blue and red together) (see gating strategy in FIG. 11A) were analyzed and calculated (dot plots are concatenates from 5 mice/group) to depict the amount of killing by PMN and macrophages (C). The number of live yeast was depicted by showing the total number of $DsRed^+$ events or plating lung CFU (D). The number indicates the n-fold reduction in lung CFU vs. the calnexin control group. *$p<0.05$ control groups without Bl-Eng-2.
Figures 11A, 11B, 11C, 11D:
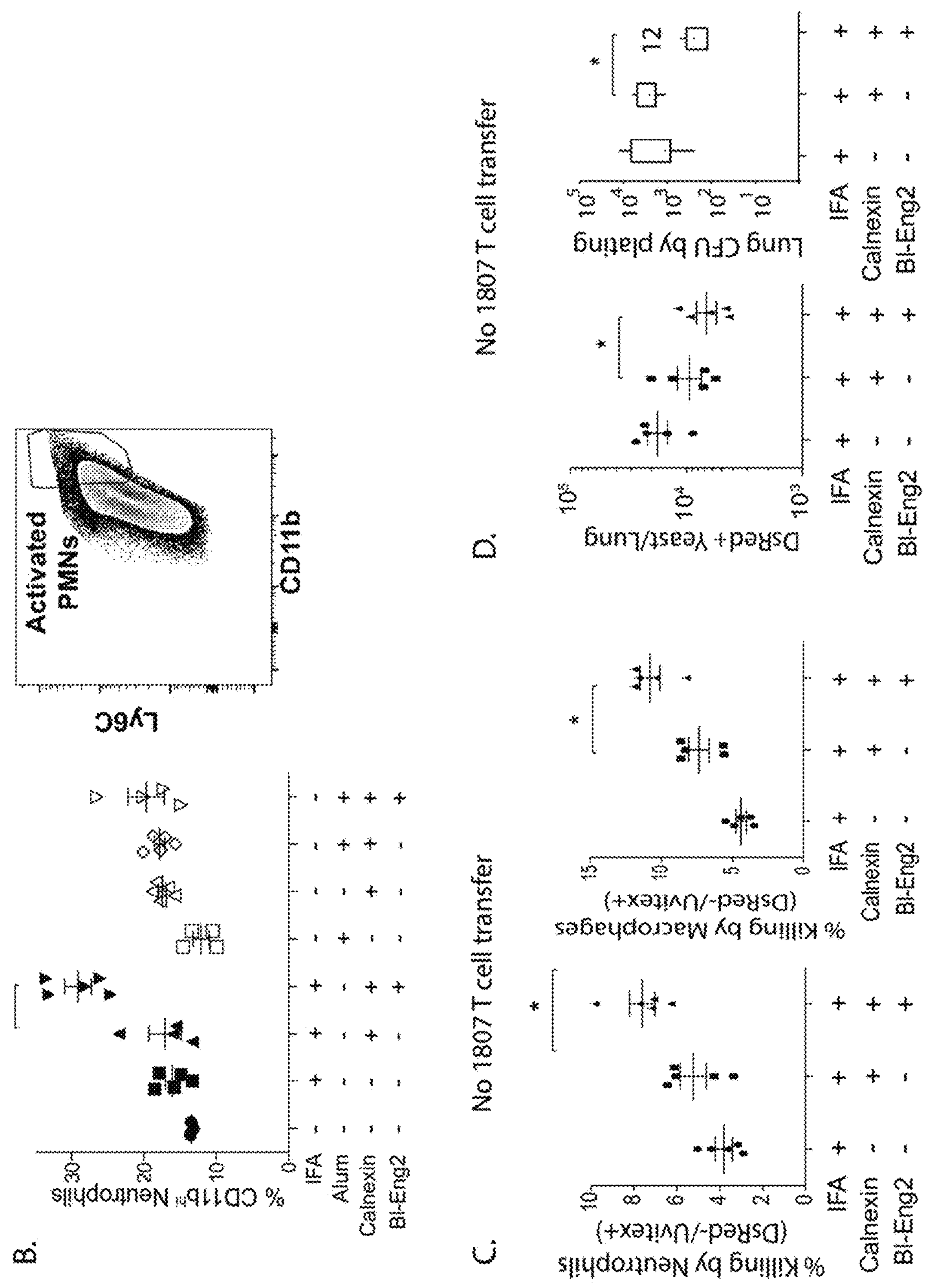

Bl-Eng-2 augments in vivo killing of fungi by neutrophils (PMN) and alveolar macrophages—To investigate the downstream myeloid effector mechanisms of Bl-Eng-2 adjuvancy we used red fluorescent *B. dermatitidis* yeast to report phagocytic uptake and fungal viability during cellular interactions with the murine leukocytes. The concept of using fluorescence to monitor microbial fate and investigate functional outcomes of individual microbial cell-host cell encounters has been introduced recently and provides a powerful strategy to measure effector mechanisms in vivo. At day 4 post-infection, mice vaccinated with calnexin+Bl-Eng-2 and calnexin+Alum+Bl-Eng-2 showed increased activation and killing by neutrophils and alveolar macrophages vs. calnexin and calnexin+Alum controls (FIGS. 5A-5C and FIG. 11). The increase in in vivo fungal killing by neutrophils and macrophages correlated with reduced numbers of $DsRed^+$ yeast in the lung (FIGS. 5D and 11D) and CFU by plating (FIGS. 5E and 11C). Bl-Eng-2 mediated effects were observed in the presence of adoptively transferred 1807 T cells (FIG. 5) and by endogenous $CD4^+$ T cells without adoptive transfer (FIGS. 11C-11D). Thus, the addition of Bl-Eng-2 augments the activation and killing by myeloid effector cells such as the neutrophils and alveolar macrophages in the lung.

DISCUSSION

We describe a novel ligand for Dectin-2: Bl-Eng2. Discovery of a potent CLR ligand may address a limitation of current vaccines: the lack of adjuvants that elicit protective cell-mediated immunity. The approach we took to identify Bl-Eng2 was based on prior work from our group and other laboratories. Dectin-2 recognizes and mediates host defense against several fungi including *C. albicans, C. glabrata, A.*

*fumigatus, Malassezia* spp., *Coccidiodes posadasii, Histoplasma capsulatum* and *B. dermatitidis*. Additionally, Dectin-$2^{-/-}$ mice vaccinated with attenuated *B. dermatitidis* yeast fail to prime Ag-specific Th1 and Th17 cells or acquire vaccine resistance to pulmonary infection. Thus, Dectin-2 regulates innate recognition of the fungal vaccine, and the development of a protective cellular immune response. Hence, we sought to identify the Dectin-2 ligand from the vaccine strain. We hypothesized that the ligand would prime APC to produce cytokines (e.g. IL-6) that are known to foster the development of Th17 cells that protect against lethal fungal challenge.

By using Dectin-2 reporter cells as a probe, we enriched and identified Bl-Eng2 by ConA binding, gel filtration and Mass spectrometry. The identification of Bl-Eng2 also led us to unveil the unappreciated role of Asp-Eng2 in binding Dectin-2. Both Eng2 proteins are bona fide Dectin-2 ligands since they trigger NFAT signaling in Dectin-2 reporter cells. Bl-Eng2 features a 45.2% overall and 60.1% GH16 domain sequence similarity to Eng2 from *A. fumigatus* (Asp-Eng2) and contains a Ser/Thr-rich C-terminus that both proteins have in common. Bl-Eng2 and Asp-Eng2 respectively harbor 68 and 74 potential O-linked glycosylation sites within their respective 134-aa and 234-aa long Ser/Thr-rich C-terminus, but display no consensus sites for N-linked glycosylation (Asn-X-Ser/Thr). In addition to the Eng2 glycoproteins, we now also establish here that MP98 from *C. neoformans* serves as a ligand for Dectin-2.

Dectin-2 has been reported to recognize high mannose structures of fungi, such as α-1,2-mannan from *C. albicans* and furfurman, which is a mannoprotein from *Malassezia* spp. Man-Lam from *M. tuberculosis* consists of four components: a mannosyl-phophatidyl-myo-inositol (MPI) anchor, a mannose backbone, an arabinan domain, and a α1,2-mannose cap. MP98 from *C. neoformans* is a mannoprotein with a Mr of 98 kDa; it contains 12 possible N-linked glycosylation sites, and 103 Ser/Thr residues at the C-terminus that serve as potential 0-linked glycosylation sites. The minimal unit of Bl-Eng2 that confers ligand activity is uncertain. Since both mannosidase and proteinase K digestion of CWE starting material reduced Dectin-2 ligand activity, both the protein and glycan moieties of Bl-Eng2 may contribute to its action, perhaps explaining its superior stimulation of cytokine responses compared to the other ligands.

We found that recombinant Bl-Eng2 elicits potent downstream functions. It induces the production of IL-6 by BMDC in a Dectin-2- and Card9-dependent manner. In addition, Bl-Eng2 induces the production of IL-6 and IL-17 by human PBMC, which may have strong implications for the translational aspect of our discovery. In comparison to previously described Dectin-2 ligands, Bl-Eng2 triggers superior cytokine production by murine BMDC. Ligand induced IL-6 production was >100 fold higher for Bl-Eng2 than the other Dectin-2 ligands: Furfurman from *Malassezia* spp. and Mannose-capped lipoarabinomannan (Man-Lam) from *M. tuberculosis* and MP98 from *C. neoformans.*

Bl-Eng2 induction of T cell priming cytokines by APCs efficiently promoted the development of calnexin Ag-specific Th17 cells (more so than Th1 cells), and recall of these cells to the lung upon fungal challenge of vaccinated mice. The large numbers of pro-inflammatory T cells sharply reduced lung CFU and increased survival after infection of Bl-Eng2 vaccinated vs. control mice. In comparison, combining commercial Alum with the calnexin subunit vaccine did not show an adjuvant effect. However, Bl-Eng-2 combined with Alum augmented its adjuvancy indicating that Bl-Eng-2 has the potential to improve T cell priming by the commercially available and FDA approved Alum. Thus, in our subunit vaccine model, Bl-Eng2-induced Dectin-2 signaling was associated with cellular immune responses that protected mice against lethal pulmonary fungal infection. Although not experimentally addressed in this manuscript, it is conceivable that Bl-Eng-2 can also augment the induction of $CD4^+$ T cell-dependent antibody responses that promote host protection against fungi, especially when combined with Alum since the latter is known to stimulate both T and B cell immune responses. It remains to be investigated whether antibody will be protective in our vaccine setting.

We previously reported that mice vaccinated with calnexin and other adjuvants (glucan particles engaging Dectin-1, Adjuplex, or the combination) were optimally protected when we adoptive transferred naïve 1807 cells to increase the pool of Ag-experienced $CD4^+$ T cells. Here, the addition of Bl-Eng2 to the same calnexin vaccine reduced lung CFU by more than two to three logs vs. control mice even without adoptive transfer of large numbers of naïve 1807 T cell precursors. These results imply that engagement of Dectin-2 by Bl-Eng2 may be better than engagement of Dectin-1 by glucan particles and other previously used adjuvants at expanding the pool of endogenous calnexin-specific $CD4^+$ T cell precursors or that Bl-Eng2 induced individual Ag-experienced cells to produce larger amounts of effector cytokines. Thus, Bl-Eng2 may be a powerful vaccine adjuvant in situations where T cell precursors are low in number and adoptive transfer of naïve T cell precursors is either not feasible or too costly.

In contrast to the protective effects of Bl-Eng2 vaccination, Man-Lam induced Dectin-2 responses that caused Th17 cell-mediated autoimmune disease pathology and EAE. Man-Lam stimulation of Dectin-2 lead to the development of MOG35-55 peptide-specific T cells that produced IL-17, IFN-γ and GM-CSF upon ex vivo stimulation. This could simply relate to model selection rather than adjuvant efficiency. Thus, it is unclear whether Man-Lam is capable of inducing protective T cell immunity in an infectious disease setting. Although *C. neoformans* MP98 and its glycan modifications also promoted T cell activation, the T-helper phenotype and functional role in resistance by primed T cells were not investigated.

In conclusion, among the few Dectin-2 ligands reported to date, or newly discovered here, Bl-Eng2 is the most potent at stimulating murine and human cells to produce cytokines known to foster the development of protective Th17 and Th1 cells e.g. IL-6 and IL-1β. The production of IL-17 and IFN-γ by Th17 and Th1 cells then promotes the activation and killing of fungi by myeloid effector cells such as neutrophils and alveolar macrophages. Since Bl-Eng2 also greatly augments protective immunity mediated by a subunit vaccine, Bl-Eng2 could potentially be harnessed as an adjuvant for vaccination against infectious disease that requires cellular immunity for host defense. The structural basis underpinning Bl-Eng2 potency as an adjuvant will be important to investigate and understand so that those features can be harnessed for vaccine development in the fight against infectious disease due to intracellular pathogens.

Material and Methods

Fungi—Strains used were wild-type, virulent *B. dermatitidis* ATCC strain 26199, DsRed26199 and strain #55, the isogenic, attenuated mutant lacking BAD1. *B. dermatitidis* was grown as yeast on Middlebrook 7H10 agar with oleic acid-albumin complex (Sigma) at 39° C.

Mouse strains—Inbred wild type C57BL/6 and congenic B6. PL-Thy1$^{a}$/Cy (stock #00406) mice carrying the Thy 1.1 allele were obtained from Jackson Laboratories, Bar Harbor, ME. *Blastomyces*-specific TCR Tg 1807 mice were generated in our lab and were backcrossed to congenic Thy1.1$^{+}$ mice as described elsewhere. Dectin-2$^{-/-}$ mice were bred at our facility. Mice were 7-8 weeks old at the time of these experiments. Mice were housed and cared for as per guidelines of the University of Wisconsin Animal Care Committee who approved all aspects of this work.

Preparation of CWE—*Blastomyces dermatitidis* yeast were harvested from 7H10 agar, washed with $H_2O$, and sonicated for 3 min on ice. After centrifuging, the soluble extract was collected, passed through a 0.45-μm pore-size filter and used as CWE. The protein level was measured with the Pierce BCA assay (Thermo Fisher Scientific).

Enrichment of mannosylated proteins and mass spectrometry analysis—To enrich the mannosylated proteins, CWE was incubated with Concanavalin A (ConA) Sepharose resin (Sigma-Aldrich), and the bound fraction was eluted with methyl-α-D-mannopyranoside as described previously. The ConA-enriched proteins were then applied to a size exclusion column of Ultragel AcA 44 resin (Pall) and eluted with PBS. The ConA enrichment and size exclusion fractions were assessed using SDS-PAGE and silver staining. Size exclusion fractions that contained Dectin-2 ligand activity were analyzed by mass spectrometry as previously described at the Mass Spectrometry Facility, University of Wisconsin-Madison. Briefly, peptides were analyzed by nano-LC-MS/MS using the Agilent 1100 nanoflow system (Agilent Technologies) connected to a hybrid linear ion trap-orbitrap mass spectrometer (LTQ-Orbitrap XL, Thermo Fisher Scientific) equipped with a nanoelectrospray ion source.

Generation and purification of r-Bl-Eng2—Bl-Eng2 was cloned and expressed in *P. pastoris* using standard recombinant techniques. Total RNA was extracted from *B. dermatitidis* yeast and transcribed to cDNA as previously described. Using the cDNA as a template, the BI-ENG2 coding sequence was amplified using KOD Hot Start DNA Polymerase (Toyobo) with primers 5'-GGCTCGAGAAAAGAGAGGCTGAAGCTAGGGCTACCAAGCTCGCGTT (SEQ ID NO:9) and 5'-GTTTCTAGACCGTACTTGTCATTTGTGGGGTATCCCG (SEQ IN NO:10), and inserted in-frame into the XhoI/XbaI sites of the pPICZaA vector (Invitrogen). The resulting expression vector was then linearized with PmeI and transformed into *Pichia pastoris* strain X-33 (Invitrogen) by electroporation. Yeast colonies were screened for Bl-Eng2 protein expression by Western blot analysis using an anti-His antibody (Cell Signaling Technology). Bl-Eng2 protein secreted from methanol-induced yeast cells was purified using Ni-NTA agarose (Qiagen) according to the manufacturer's protocol, and dialyzed against PBS. Purity of recombinant Bl-Eng2 was assessed by SDS-PAGE and silver staining. Without being bound to any particular theory, it is believed that the alpha-factor signal peptide is excised from the recombinant Bl-Eng2 upon secretion of the protein from the yeast. The predicted sequence of the Bl-Eng2 recombinant protein after excision of the alpha-factor signal peptide is included below.

Predicted recombinant Bl-Eng2 protein: alpha-factor signal peptide excised during secretion (SEQ ID NO:11).

```
RATKLALLAALAKLSTGAYVLQDDYQPSNFFDDFAFFDGPDPSNAYVTY

VDKSKALRDGLASNNNDFVYLGVDHQNVARGRGRESVRLETKKSYKHGL
```

-continued

```
IVADISHMPGNICGTWPAFWATGATWPDDGEFDIIEGVNKQNKNVVALH

TTAGCKVEDNNKYSGILVTKDCDVYSPNQPSNQGCLFRAPSATSYGTAF

NSIGGGVYATEWTSDSISVWFFPRYQIPSNINDENPDPSTWPRPIAHFT

GCEFDKFFQEQRIIFNTAFCGDWAKATWNENGCAAGGRTCEDYVKNNPW

AFSEAFWSINYMKVFQNKQGDTSTSTTTSSTSSTSSSSTEAPTTTMTTS

STYEPSVSSSTAPEPSQSASTPSEYPQPSTAEPTASSSSYPKSSFASTD

SPVPTDYPVPSSDEPTVPSATYSESSPVPTDYPVPSSDEPTVPSATYSE

SLPSASAPSEYPTGTASVDPTDVSSCTPPPTQSCITYTTKTTIAIVVTA

PESYKEAIQTESAEDETEPAAYPTEPAGYPTNDKYGLEQKLISEEDLNS

AVDHHHHHH
```

Carbohydrate Analysis—Bl-Eng2 protein glycosylation was assessed using the Pierce Glycoprotein Staining Kit (Thermo Fisher Scientific). Monosaccharide composition was determined by gas chromatography as described elsewhere.

CLR reporter assay—B3Z/BWZ reporter cells expressing Dectin-2, Mincle, MCL and Dectin-1 have been described previously. For B3Z/BWZ cell stimulation, $10^5$ B3Z/BWZ cells per well in a 96-well plate were incubated for 18 h with heat-killed fungal cells or plate-coated ligands. β-galactosidase (lacZ) activity was measured in total cell lysates using CPRG (Roche) as a substrate. OD 560 was measured using OD 620 as a reference.

Stimulation of mouse BMDCs or human PBMCs and cytokine detection—Generation of bone marrow-derived dendritic cells (BMDCs) has been described previously. Peripheral blood mononuclear cells (PBMCs) were isolated from heparinized whole blood collected over Ficoll-Paque Plus (GE). 1-2×$10^5$ BMDCs or 5×$10^5$ PBMCs per well in a 96-well plate were incubated with plate-bound Bl-Eng2. After 24 h, supernatants were collected and cytokine levels were measured by ELISA (R&D Systems or Biolegend) according to the manufacturer's specifications.

Vaccination with Calnexin and Bl-Eng2 and enumeration of rare epitope-specific T cells—Prior to vaccination, mice received adoptively transferred naïve 1807 T cells or not. Mice were vaccinated twice subcutaneously with 10 μg recombinant calnexin and 10 μg Bl-Eng2 formulated in incomplete Freund's adjuvant (IFA), two weeks apart. Two weeks after the boost, mice were challenged with 2×$10^4$ 26199 yeast and analyzed for lung T cell responses (at day 4 post-infection) and lung CFU (at day 4 or two weeks post-infection). 1807 T cell responses were detected with the congenic Thy1.1 marker and endogenous, calnexin-specific T cells by tetramer. T cells were detected using the following antibodies: tetramer-PE, CD4-BUV395, CD8-PeCy7, CD3-BV421, CD90.2-BV785, CD44-BV650, Live-dead Near IR, IFN-γ-A488 and IL-17-A647.

Intracellular cytokine stain—Lung cells were harvested at day 4 post-infection. Cells (0.5×$10^6$ cells/ml) were stimulated for 5 hours with anti-CD3 (clone 145-2C11; 0.1 μg/ml) and anti-CD28 (clone 37.51; 1 μg/ml) in the presence of Golgi-Stop (BD Biosciences). Stimulation with fungal ligands yielded comparable cytokine production by transgenic T-cells compared to CD3/CD28 stimulation. After cells were washed and stained for surface CD4 and CD8 using anti-CD4 BV395, anti-CD8 PeCy7, and anti-CD44-FITC mAbs (Pharmingen), they were fixed and permeabilized in Cytofix/Cytoperm at 4° C. overnight. Permeabilized cells were stained with anti-IL-17A PE and anti-IFN-γ Alexa 700 (clone XMG1.2) conjugated mAbs (Pharmingen) in FACS buffer for 30 min at 4° C., washed, and analyzed by FACS. Cells were gated on CD4 and cytokine expression in each gate analyzed. The number of cytokine positive $CD4^+$ T cells per lung was calculated by multiplying the percent of cytokine-producing cells by the number of $CD4^+$ T cells in the lung.

The generation of bone marrow dendritic cells—Bone marrow-derived dendritic cells (BMDCs) were obtained from the femurs and tibias of individual mice. Each bone was flushed with 10 ml of 1% FBS in RPMI through a 22G needle. Red blood cells were lysed followed by wash and re-suspension of cells in 10% FBS in RPMI medium. In a petri dish, $2\times10^6$ bone marrow cells were plated in 10 ml of RPMI containing 10% FBS plus penicillin-streptomycin (P/S) (HyClone), 2-mercaptoethanol and 20 ng/ml of rGM-CSF. The culture media were refreshed every three days and BMDCs were harvested after 10 days for in vitro co-culture assays.

Ex vivo stimulation of primed T cells for cytokine protein measurement—Ex vivo cell culture supernatants were generated using the brachial and inguinal draining lymph nodes harvested from mice 28 days post-vaccination and at day 4 post-infection, washed and resuspended in complete RPMI containing 10 μg/ml recombinant calnexin, and plated in 96-well plates at a concentration of $5\times10^5$ cells/well. Supernatants were collected from ex vivo co-cultures after three days of incubation at 37° C. and 5% $CO_2$. IFN-γ and IL-17 (R&D System) were measured by ELISA according to manufacturer specifications (detection limits, 0.05 ng/ml and 0.02 ng/ml, respectively).

Tracking association of yeast with neutrophils and alveolar macrophages in vivo—Mice were euthanized three days after challenge i.t. with $10^5$ DsRed yeast and hearts were perfused with PBS to remove blood from the lungs to improve staining. Lungs were dissociated, digested and stained as described previously. In summary, lungs were dissociated and digested in buffer containing collagenase D and DNase I. After erythrocyte lysis, cells were stained for myeloid cell markers and then fixed in Cytofix/Cytoperm (BD Biosciences, San Jose, CA). Cells were stained for 30 minutes at room temperature with 1 μg/ml Uvitex-2B (Polysciences, Warrington, PA) diluted in BD perm/wash buffer and then subsequently washed with BD perm/wash buffer and fixed with 2% paraformaldehyde.

Statistics—Differences in the number of cells and lung CFU were analyzed using Wilcoxon rank and Mann Whitney test for non-parametric data or a T-test if data were normally distributed. A Bonferroni adjustment was used to correct for multiple tests. A value of $P<0.05$ is considered significant.

Example 2

Figure 12:
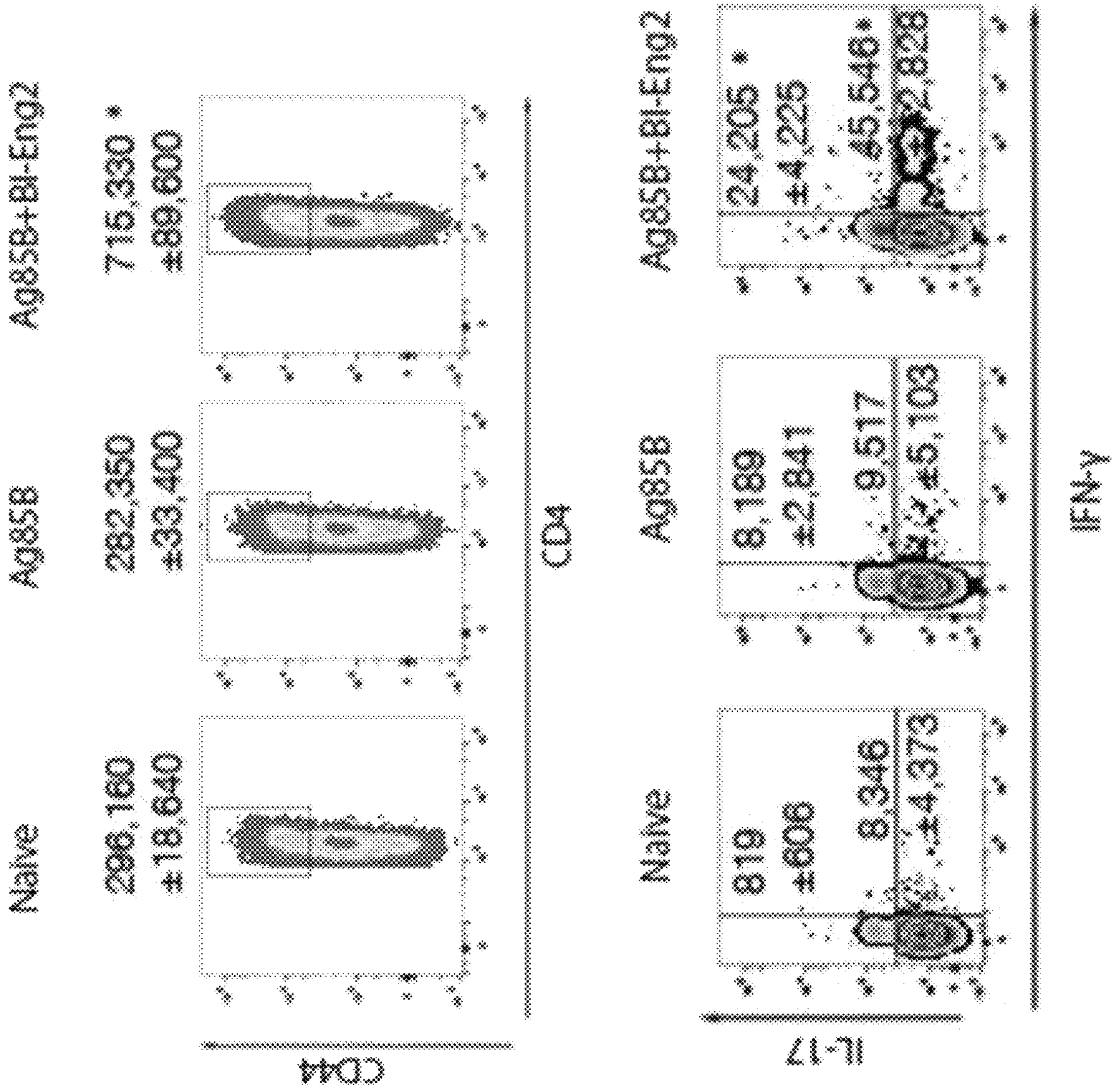
FIG. 12 demonstrates a TB vaccine model. Mice were subcutaneously vaccinated with 5 μg Ag85B in IFA in the presence or absence of 10 μg Bl-Eng-2 twice, two weeks apart. Two weeks after the boost, the mice were challenged with 150 CFU of *M. tuberculosis* and three weeks later the lungs were harvested and analyzed for T cell immune responses. The mean±SEM number of activated ($CD44^+$) and cytokine producing $CD4^+$ T cells were enumerated by FACS. *, p value <0.05 vs. all other groups.
Figure 13:
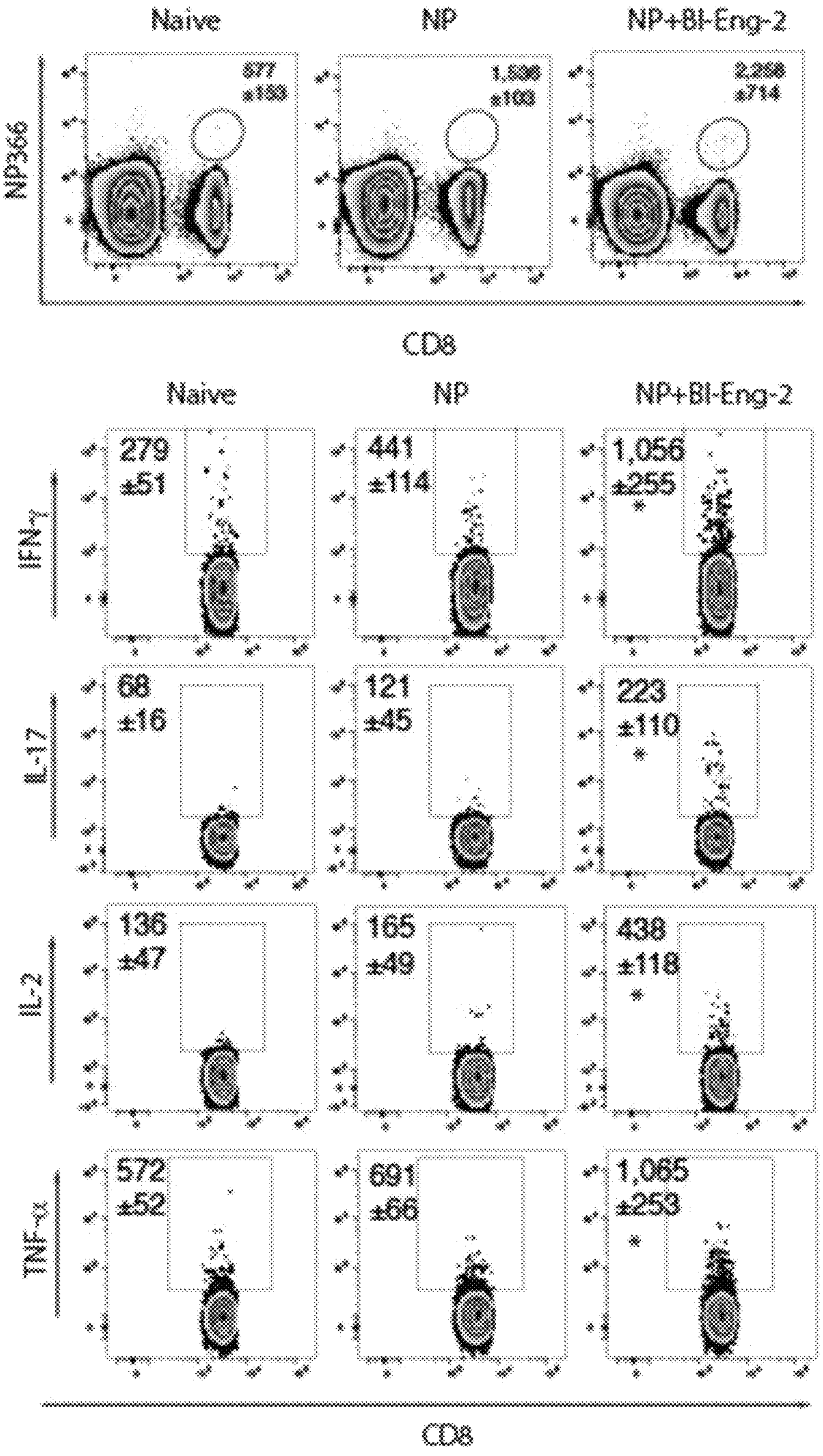
FIG. 13 demonstrates an influenza vaccine model. Mice were intranasally vaccinated with 5 μg NP and 10 μg Bl-Eng-2 or not. 8 days after the boost, lung T cells were stimulated with NP peptide and analyzed for the mean±SEM number of tetramer (NP396*) and cytokine producing $CD8^+$ T cells by FACS. *, p value <0.05 vs. all other groups.

The embodiment described herein demonstrates the use of Bl-Eng2 as a vaccine adjuvant in bacterial and viral vaccines. As demonstrated in FIG. 12 and FIG. 13, Bl-Eng2 functions as an adjuvant in bacterial and viral vaccine formulations and increased the number of activated (CD44+) CD4+ and CD8+ producing T cells. Mice were vaccinated with Ag85B from *Mycobacterium tuberculosis* and Nucleoprotein (NP) from Influenza A in the presence and absence of Bl-Eng-2 and compared the number of corresponding cytokine producing $CD4^+$ and $CD8^+$ T cells, respectively. In the TB vaccine model, Ag-specific IL-17 and IFN-γ producing $CD4^+$ T cells and in the Influenza model, IFN-γ producing cytotoxic $CD8^+$ T cells (CTL) are thought to be most protective against bacterial and viral infection, respectively. The addition of Bl-Eng-2 to Ags 85B or NP augmented the number of cytokine producing Ag-specific $CD4^+$ and $CD8^+$ T cells in both models. Thus, Bl-Eng-2 augments immunity also in response to non-fungal (bacterial and viral) Ags and does not only increase $CD4^+$ but also $CD8^+$ T cell immune responses.

Example 3

Figure 14:
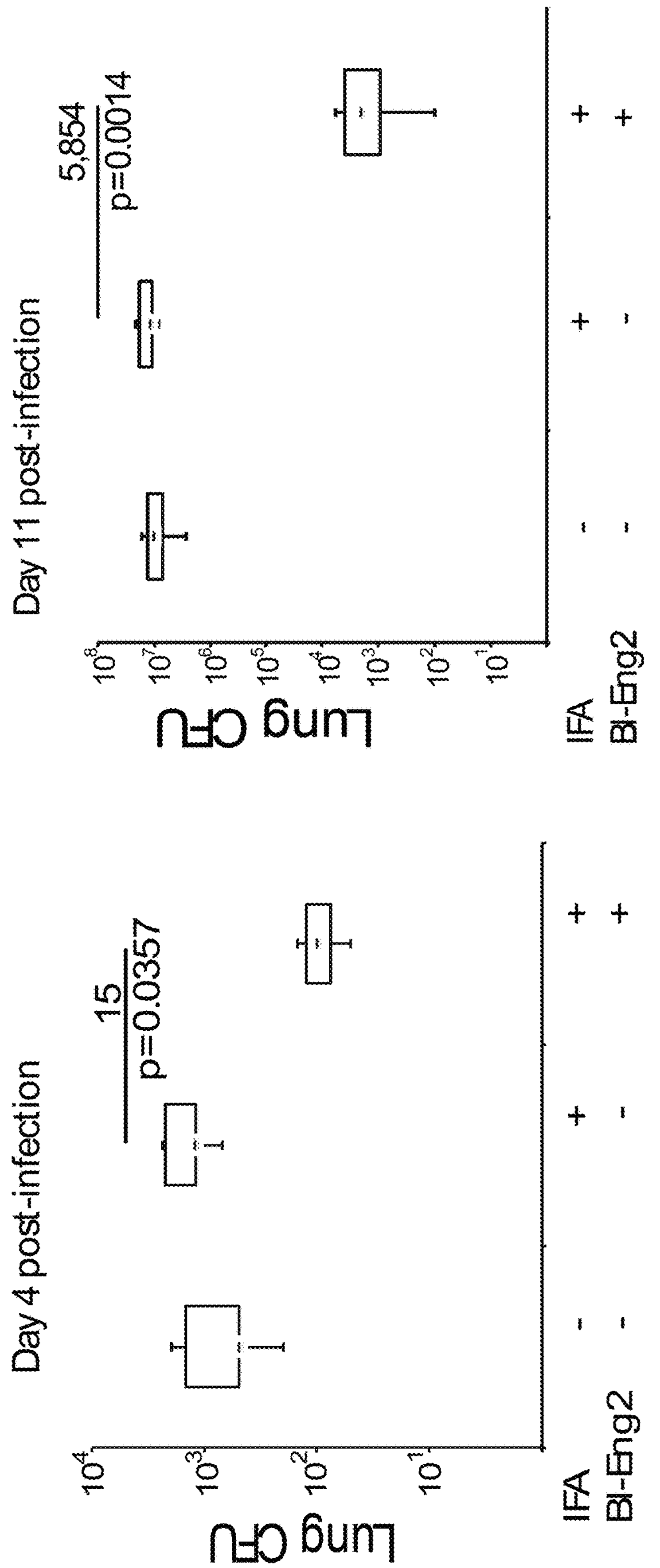
FIG. 14 demonstrates that vaccination with Bl-Eng2 antigen protects mice against fungal infection. Mice were vaccinated subcutaneously with 5 μg Bl-Eng2 protein formulated with incomplete Freunds adjuvant (IFA, which consists of mineral oil) twice two weeks apart. Two weeks after the boost, mice were challenged with 2×10E4 wild type (ATCC 26199) *B. dermatitidis* yeast. At day 4 and 11 post-infection animals were sacrificed their lungs plated for colony forming units (CFU). Data represent an average of 5-10 mice per group. Numbers indicate the n-fold change vs. IFA control vaccinated mice.
Figure 15:
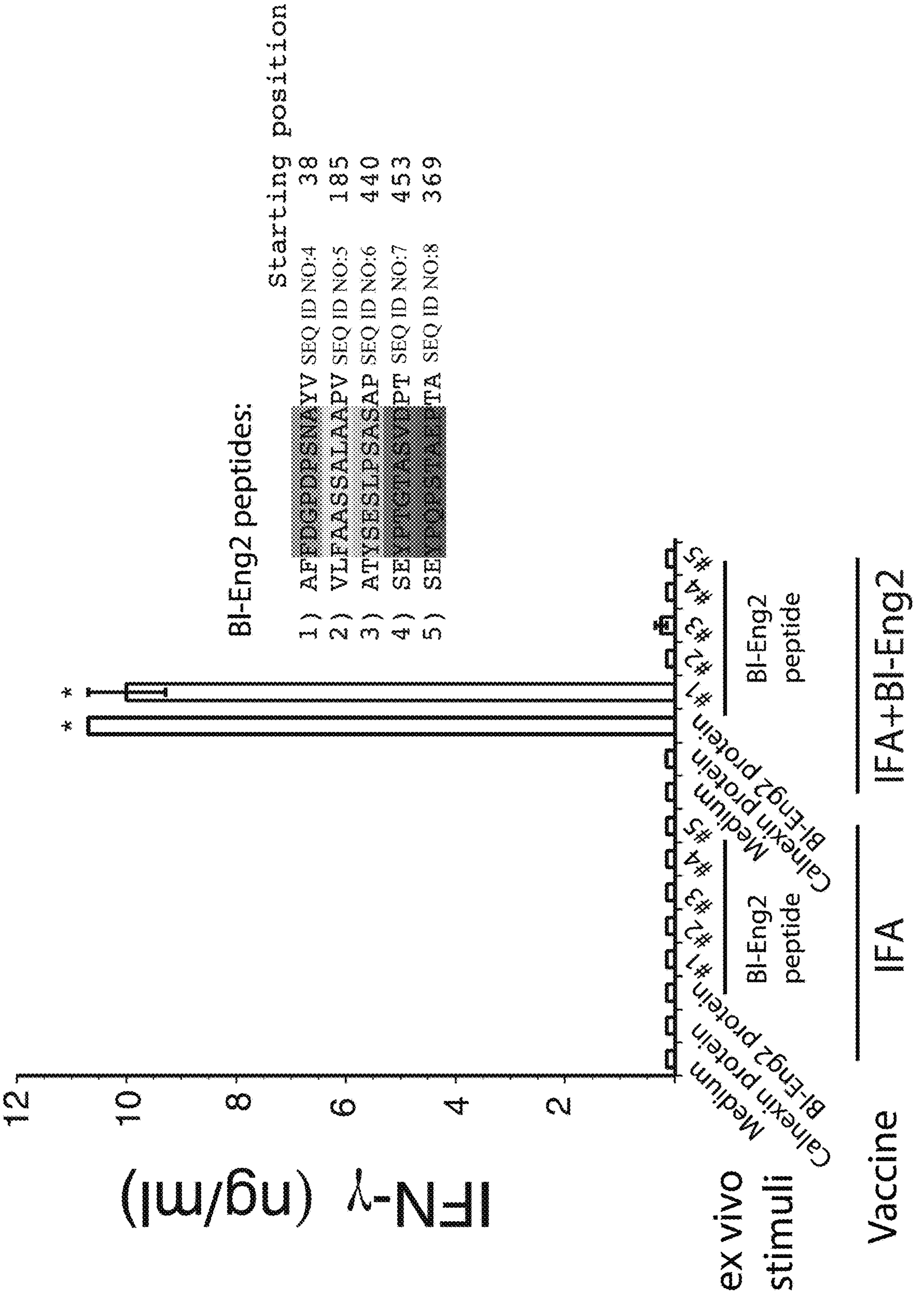
FIG. 15 demonstrates T cell epitope identification of the Bl-Eng2 protein. We synthesized 5 software predicted T cell epitopes (peptides) and stimulated splenocytes from vaccinated mice (FIG. 14) ex vivo. Peptide #1 (SEQ ID NO:4) stimulated splenocytes from Bl-Eng2 vaccinated mice to produce IFN-γ comparable to full length Bl-Eng2 protein, whereas the other peptides and Calnexin protein did not. Thus, peptide #1 (SEQ ID NO:4) is likely harboring the protective T cell epitope.

The embodiment described herein demonstrates the use of Bl-Eng2 as a novel antigen for use in vaccine compositions. As demonstrated in FIGS. 14A-14B and FIGS. 15A-15B, Bl-Eng2 functions as an antigen when used in vaccine compositions to raise antifungal T cells in the subject mice. Mice subcutaneously vaccinated with Bl-Eng2 formulated in IFA had significantly reduced lung CFU at 4 (15-fold) and 11 post-infection (>5,000 fold) compared to control mice (FIG. 14). Splenocytes from Bl-Eng2 vaccinated mice produced >10 ng/ml INF-7 when stimulated in vitro with full length Bl-Eng2 protein or peptide 1 which is comprised of the following amino acid sequence: AFFDGPDPSNAYV (SEQ ID NO:4). Therefore vaccination with this peptide alone will engender a similar level of protection as full length Bl-Eng2 protein.

This peptide could also be used to expand autologous, endogenous Bl-Eng2-specific T cells of patients that will undergo transplantation, chemotherapy or other immunocompromising treatments to boost their immunity against fungal infection (e.g. cellular immunotherapy following stem cell transplantation). The lethality of invasive pulmonary infection with *Aspergillus fumigatus* is 50-90% in that patient population.

REFERENCES

1. Brown G D, Denning D W, Gow N A, Levitz S M, Netea M G, et al. (2012) Hidden killers: human fungal infections. Sci Transl Med 4: 165rv113.
2. Brown G D, Denning D W, Levitz S M (2012) Tackling human fungal infections. Science 336: 647.
3. Romani L (2011) Immunity to fungal infections. Nat Rev Immunol 11: 275-288.
4. Wuthrich M, Deepe G S, Jr., Klein B (2012) Adaptive immunity to fungi. Annu Rev Immunol 30: 115-148.
5. Leibundgut-Landmann S, Wuthrich M, Hohl T M (2012) Immunity to fungi. Curr Opin Immunol 24: 449-458.
6. Wuthrich M, Gern B, Hung C Y, Ersland K, Rocco N, et al. (2011) Vaccine-induced protection against 3 systemic mycoses endemic to North America requires Th17 cells in mice. J Clin Invest 121: 554-568.
7. Zelante T, De Luca A, Bonifazi P, Montagnoli C, Bozza S, et al. (2007) IL-23 and the Th17 pathway promote inflammation and impair antifungal immune resistance. Eur J Immunol 37: 2695-2706.
8. Mori A, Oleszycka E, Sharp F A, Coleman M, Ozasa Y, et al. (2012) The vaccine adjuvant alum inhibits IL-12 by promoting PI3 kinase signaling while chitosan does not inhibit IL-12 and enhances Th1 and Th17 responses. Eur J Immunol 42: 2709-2719.
9. Gringhuis S I, Wevers B A, Kaptein T M, van Capel T M, Theelen B, et al. (2011) Selective C-Rel activation via Malt1 controls anti-fungal T(H)-17 immunity by dectin-1 and dectin-2. PLoS Pathog 7: e1001259.

10. Gringhuis S I, den Dunnen J, Litjens M, van der Vlist M, Wevers B, et al. (2009) Dectin-1 directs T helper cell differentiation by controlling noncanonical NF-kappaB activation through Raf-1 and Syk. Nat Immunol 10: 203-213.
11. Geijtenbeek T B, Gringhuis S I (2009) Signalling through C-type lectin receptors: shaping immune responses. Nat Rev Immunol 9: 465-479.
12. LeibundGut-Landmann S, Gross O, Robinson M J, Osorio F, Slack E C, et al. (2007) Syk- and CARD9-dependent coupling of innate immunity to the induction of T helper cells that produce interleukin 17. Nat Immunol 8: 630-638.
13. Robinson M J, Osorio F, Rosas M, Freitas R P, Schweighoffer E, et al. (2009) Dectin-2 is a Syk-coupled pattern recognition receptor crucial for Th17 responses to fungal infection. J Exp Med 206: 2037-2051.
14. Saijo S, Ikeda S, Yamabe K, Kakuta S, Ishigame H, et al. (2010) Dectin-2 recognition of alpha-mannans and induction of Th17 cell differentiation is essential for host defense against *Candida albicans*. Immunity 32: 681-691.
15. Zhu L L, Zhao X Q, Jiang C, You Y, Chen X P, et al. (2013) C-type lectin receptors Dectin-3 and Dectin-2 form a heterodimeric pattern-recognition receptor for host defense against fungal infection. Immunity 39: 324-334.
16. Rivera A, Hohl T M, Collins N, Leiner I, Gallegos A, et al. (2011) Dectin-1 diversifies *Aspergillus fumigatus*-specific T cell responses by inhibiting T helper type 1 CD4 T cell differentiation. J Exp Med 208: 369-381.
17. Loures F V, Rohm M, Lee C K, Santos E, Wang J P, et al. (2015) Recognition of *Aspergillus fumigatus* hyphae by human plasmacytoid dendritic cells is mediated by dectin-2 and results in formation of extracellular traps. PLoS Pathog 11: e1004643.
18. Carrion Sde J, Leal S M, Jr., Ghannoum M A, Aimanianda V, Latge J P, et al. (2013) The RodA hydrophobin on *Aspergillus fumigatus* spores masks dectin-1- and dectin-2-dependent responses and enhances fungal survival in vivo. J Immunol 191: 2581-2588.
19. Wang H, Lebert V, Hung C Y, Galles K, Saijo S, et al. (2014) C-type lectin receptors differentially induce th17 cells and vaccine immunity to the endemic mycosis of north America. J Immunol 192: 1107-1119.
20. Yonekawa A, Saijo S, Hoshino Y, Miyake Y, Ishikawa E, et al. (2014) Dectin-2 is a direct receptor for mannose-capped lipoarabinomannan of mycobacteria. Immunity 41: 402-413.
21. Wuthrich M, Brandhorst T T, Sullivan T D, Filutowicz H, Sterkel A, et al. (2015) Calnexin induces expansion of antigen-specific CD4(+) T cells that confer immunity to fungal ascomycetes via conserved epitopes. Cell Host Microbe 17: 452-465.
22. Hartl L, Gastebois A, Aimanianda V, Latge J P (2011) Characterization of the GPI-anchored endo beta-1,3-glucanase Eng2 of *Aspergillus fumigatus*. Fungal Genet Biol 48: 185-191.
23. McGreal E P, Rosas M, Brown G D, Zamze S, Wong S Y, et al. (2006) The carbohydrate-recognition domain of Dectin-2 is a C-type lectin with specificity for high mannose. Glycobiology 16: 422-430.
24. Sato K, Yang X L, Yudate T, Chung J S, Wu J, et al. (2006) Dectin-2 is a pattern recognition receptor for fungi that couples with the Fc receptor gamma chain to induce innate immune responses. J Biol Chem 281: 38854-38866.
25. Ishikawa T, Itoh F, Yoshida S, Saijo S, Matsuzawa T, et al. (2013) Identification of Distinct Ligands for the C-type Lectin Receptors Mincle and Dectin-2 in the Pathogenic Fungus *Malassezia*. Cell Host Microbe 13: 477-488.
26. Taylor P R, Roy S, Leal S M, Jr., Sun Y, Howell S J, et al. (2014) Activation of neutrophils by autocrine IL-17A-IL-17R C interactions during fungal infection is regulated by IL-6, IL-23, RORgammat and dectin-2. Nat Immunol 15: 143-151.
27. Levitz S M, Nong S, Mansour M K, Huang C, Specht C A (2001) Molecular characterization of a mannoprotein with homology to chitin deacetylases that stimulates T cell responses to *Cryptococcus neoformans*. Proc Natl Acad Sci USA 98: 10422-10427.
28. Wuthrich M, Ersland K, Sullivan T, Galles K, Klein B S (2012) Fungi subvert vaccine T cell priming at the respiratory mucosa by preventing chemokine-induced influx of inflammatory monocytes. Immunity 36: 680-692.
29. Jhingran A, Mar K B, Kumasaka D K, Knoblaugh S E, Ngo L Y, et al. (2012) Tracing conidial fate and measuring host cell antifungal activity using a reporter of microbial viability in the lung. Cell Rep 2: 1762-1773.
30. Ifrim D C, Bain J M, Reid D M, Oosting M, Verschueren I, et al. (2014) Role of Dectin-2 for host defense against systemic infection with *Candida glabrata*. Infect Immun 82: 1064-1073.
31. Lin L, Ibrahim A S, Xu X, Farber J M, Avanesian V, et al. (2009) Th1-Th17 cells mediate protective adaptive immunity against *Staphylococcus aureus* and *Candida albicans* infection in mice. PLoS Pathog 5: e1000703.
32. Spellberg B, Ibrahim A S, Lin L, Avanesian V, Fu Y, et al. (2008) Antibody titer threshold predicts anti-candidal vaccine efficacy even though the mechanism of protection is induction of cell-mediated immunity. J Infect Dis 197: 967-971.
33. Lam J S, Mansour M K, Specht C A, Levitz S M (2005) A model vaccine exploiting fungal mannosylation to increase antigen immunogenicity. J Immunol 175: 7496-7503.
34. Specht C A, Nong S, Dan J M, Lee C K, Levitz S M (2007) Contribution of glycosylation to T cell responses stimulated by recombinant *Cryptococcus neoformans* mannoprotein. J Infect Dis 196: 796-800.
35. Sterkel A K, Lorenzini J L, Fites J S, Subramanian Vignesh K, Sullivan T D, et al. (2016) Fungal Mimicry of a Mammalian Aminopeptidase Disables Innate Immunity and Promotes Pathogenicity. Cell Host Microbe 19: 361-374.
36. Brandhorst T T, Wuthrich M, Warner T, Klein B (1999) Targeted gene disruption reveals an adhesin indispensable for pathogenicity of *Blastomyces dermatitidis*. J Exp Med 189: 1207-1216.
37. Marty A J, Wuthrich M, Carmen J C, Sullivan T D, Klein B S, et al. (2013) Isolation of *Blastomyces dermatitidis* yeast from lung tissue during murine infection for in vivo transcriptional profiling. Fungal Genet Biol 56: 1-8.
38. Zarnowski R, Westler W M, Lacmbouh G A, Marita J M, Bothe J R, et al. (2014) Novel entries in a fungal biofilm matrix encyclopedia. MBio 5: e01333-01314.
39. Wuthrich M, Wang H, Li M, Lerksuthirat T, Hardison S E, et al. (2015) *Fonsecaea pedrosoi*-induced Th17-cell differentiation in mice is fostered by Dectin-2 and suppressed by Mincle recognition. Eur J Immunol 45: 2542-2552.
40. Wuthrich M, Filutowicz H I, Klein B S (2000) Mutation of the WI-1 gene yields an attenuated *Blastomyces dermatitidis* strain that induces host resistance. J Clin Invest 106: 1381-1389.

We claim:

1. A method of eliciting an immune response in a subject against an antigen, the method comprising:

(a) administering a therapeutically effective amount of a composition comprising the antigen and a Dectin-2 ligand selected from β-1,3-endoglucanase from *Blastomyces dermatitidis* (Bl-Eng2) or endoglucanase from *Coccidioides immitis* (C-Eng2) and a pharmaceutically acceptable carrier to the subject, wherein the Bl-Eng2 is recombinant Bl-Eng2 or purified Bl-Eng2 and the C-Eng2 is recombinant C-Eng2 or purified C-Eng2.

2. The method of claim 1, wherein the immune response is an IL-17+ or INF-γ+ T cell immune response against the endoglucanase.

3. The method of claim 1, wherein the antigen is a fungal antigen.

4. The method of claim 1, wherein the antigen is a bacterial antigen.

5. The method of claim 1, wherein the antigen is a viral antigen.

6. The method of claim 1, wherein the Dectin-2 ligand is selected from Bl-Eng2 comprising SEQ ID NO:1 or C-Eng2 comprising SEQ ID NO:14.

7. The method of claim 1, wherein the Dectin-2 ligand is selected from purified β-1,3-endoglucanase from *Blastomyces dermatitidis* (Bl-Eng2) or purified endoglucanase from *Coccidioides immitis* (C-Eng2).

* * * * *

SEQUENCE LISTING

<160> NUMBER OF SEQ ID NOS: 16

<210> SEQ ID NO 1
<211> LENGTH: 526
<212> TYPE: PRT
<213> ORGANISM: Blastomyces dermatitidis

<400> SEQUENCE: 1

Met Arg Ala Thr Lys Leu Ala Leu Leu Ala Ala Leu Ala Lys Leu Ser
1               5                   10                  15

Thr Gly Ala Tyr Val Leu Gln Asp Asp Tyr Gln Pro Ser Asn Phe Phe
            20                  25                  30

Asp Asp Phe Ala Phe Phe Asp Gly Pro Asp Pro Ser Asn Ala Tyr Val
        35                  40                  45

Thr Tyr Val Asp Lys Ser Lys Ala Leu Arg Asp Gly Leu Ala Ser Asn
    50                  55                  60

Asn Asn Asp Phe Val Tyr Leu Gly Val Asp His Gln Asn Val Ala Arg
65                  70                  75                  80

Gly Arg Gly Arg Glu Ser Val Arg Leu Glu Thr Lys Lys Ser Tyr Lys
                85                  90                  95

His Gly Leu Ile Val Ala Asp Ile Ser His Met Pro Gly Asn Ile Cys
            100                 105                 110

Gly Thr Trp Pro Ala Phe Trp Ala Thr Gly Ala Thr Trp Pro Asp Asp
        115                 120                 125

Gly Glu Phe Asp Ile Ile Glu Gly Val Asn Lys Gln Asn Lys Asn Val
    130                 135                 140

Val Ala Leu His Thr Thr Ala Gly Cys Lys Val Glu Asp Asn Asn Lys
145                 150                 155                 160

Tyr Ser Gly Ile Leu Val Thr Lys Asp Cys Asp Val Tyr Ser Pro Asn
                165                 170                 175

Gln Pro Ser Asn Gln Gly Cys Leu Phe Arg Ala Pro Ser Ala Thr Ser
            180                 185                 190

Tyr Gly Thr Ala Phe Asn Ser Ile Gly Gly Gly Val Tyr Ala Thr Glu
        195                 200                 205

Trp Thr Ser Asp Ser Ile Ser Val Trp Phe Phe Pro Arg Tyr Gln Ile
    210                 215                 220

Pro Ser Asn Ile Asn Asp Glu Asn Pro Asp Pro Ser Thr Trp Pro Arg
225                 230                 235                 240

Pro Ile Ala His Phe Thr Gly Cys Glu Phe Asp Lys Phe Phe Gln Glu
                245                 250                 255

Gln Arg Ile Ile Phe Asn Thr Ala Phe Cys Gly Asp Trp Ala Lys Ala
            260                 265                 270

Thr Trp Asn Glu Asn Gly Cys Ala Ala Gly Gly Arg Thr Cys Glu Asp
        275                 280                 285

Tyr Val Lys Asn Asn Pro Trp Ala Phe Ser Glu Ala Phe Trp Ser Ile
    290                 295                 300

Asn Tyr Met Lys Val Phe Gln Asn Lys Gln Gly Asp Thr Ser Thr Ser
305                 310                 315                 320

Thr Thr Thr Ser Ser Thr Ser Ser Thr Ser Ser Ser Ser Thr Glu Ala
                325                 330                 335

Pro Thr Thr Thr Met Thr Thr Ser Ser Thr Tyr Glu Pro Ser Val Ser
            340                 345                 350

Ser Ser Thr Ala Pro Glu Pro Ser Gln Ser Ala Ser Thr Pro Ser Glu
        355                 360                 365

-continued

```
Tyr Pro Gln Pro Ser Thr Ala Glu Pro Thr Ala Ser Ser Ser Ser Tyr
    370                 375                 380

Pro Lys Ser Ser Phe Ala Ser Thr Asp Ser Pro Val Pro Thr Asp Tyr
385                 390                 395                 400

Pro Val Pro Ser Ser Asp Glu Pro Thr Val Pro Ser Ala Thr Tyr Ser
                405                 410                 415

Glu Ser Ser Pro Val Pro Thr Asp Tyr Pro Val Pro Ser Ser Asp Glu
            420                 425                 430

Pro Thr Val Pro Ser Ala Thr Tyr Ser Glu Ser Leu Pro Ser Ala Ser
        435                 440                 445

Ala Pro Ser Glu Tyr Pro Thr Gly Thr Ala Ser Val Asp Pro Thr Asp
    450                 455                 460

Val Ser Ser Cys Thr Pro Pro Pro Thr Gln Ser Cys Ile Thr Tyr Thr
465                 470                 475                 480

Thr Lys Thr Thr Ile Ala Ile Val Val Thr Ala Pro Glu Ser Tyr Lys
                485                 490                 495

Glu Ala Ile Gln Thr Glu Ser Ala Glu Asp Glu Thr Glu Pro Ala Ala
            500                 505                 510

Tyr Pro Thr Glu Pro Ala Gly Tyr Pro Thr Asn Asp Lys Tyr
        515                 520                 525


<210> SEQ ID NO 2
<211> LENGTH: 637
<212> TYPE: PRT
<213> ORGANISM: Artificial Sequence
<220> FEATURE:
<223> OTHER INFORMATION: synthetic

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Arg Ala Thr Lys Leu Ala Leu
                85                  90                  95

Leu Ala Ala Leu Ala Lys Leu Ser Thr Gly Ala Tyr Val Leu Gln Asp
            100                 105                 110

Asp Tyr Gln Pro Ser Asn Phe Phe Asp Asp Phe Ala Phe Phe Asp Gly
        115                 120                 125

Pro Asp Pro Ser Asn Ala Tyr Val Thr Tyr Val Asp Lys Ser Lys Ala
    130                 135                 140

Leu Arg Asp Gly Leu Ala Ser Asn Asn Asn Asp Phe Val Tyr Leu Gly
145                 150                 155                 160

Val Asp His Gln Asn Val Ala Arg Gly Arg Gly Arg Glu Ser Val Arg
                165                 170                 175

Leu Glu Thr Lys Lys Ser Tyr Lys His Gly Leu Ile Val Ala Asp Ile
            180                 185                 190

Ser His Met Pro Gly Asn Ile Cys Gly Thr Trp Pro Ala Phe Trp Ala
        195                 200                 205
```

-continued

```
Thr Gly Ala Thr Trp Pro Asp Asp Gly Glu Phe Asp Ile Ile Glu Gly
    210                 215                 220

Val Asn Lys Gln Asn Lys Asn Val Val Ala Leu His Thr Thr Ala Gly
225                 230                 235                 240

Cys Lys Val Glu Asp Asn Asn Lys Tyr Ser Gly Ile Leu Val Thr Lys
                245                 250                 255

Asp Cys Asp Val Tyr Ser Pro Asn Gln Pro Ser Asn Gln Gly Cys Leu
            260                 265                 270

Phe Arg Ala Pro Ser Ala Thr Ser Tyr Gly Thr Ala Phe Asn Ser Ile
        275                 280                 285

Gly Gly Gly Val Tyr Ala Thr Glu Trp Thr Ser Asp Ser Ile Ser Val
    290                 295                 300

Trp Phe Phe Pro Arg Tyr Gln Ile Pro Ser Asn Ile Asn Asp Glu Asn
305                 310                 315                 320

Pro Asp Pro Ser Thr Trp Pro Arg Pro Ile Ala His Phe Thr Gly Cys
                325                 330                 335

Glu Phe Asp Lys Phe Phe Gln Glu Gln Arg Ile Ile Phe Asn Thr Ala
            340                 345                 350

Phe Cys Gly Asp Trp Ala Lys Ala Thr Trp Asn Glu Asn Gly Cys Ala
        355                 360                 365

Ala Gly Gly Arg Thr Cys Glu Asp Tyr Val Lys Asn Asn Pro Trp Ala
    370                 375                 380

Phe Ser Glu Ala Phe Trp Ser Ile Asn Tyr Met Lys Val Phe Gln Asn
385                 390                 395                 400

Lys Gln Gly Asp Thr Ser Thr Ser Thr Thr Thr Ser Ser Thr Ser Ser
                405                 410                 415

Thr Ser Ser Ser Ser Thr Glu Ala Pro Thr Thr Thr Met Thr Thr Ser
            420                 425                 430

Ser Thr Tyr Glu Pro Ser Val Ser Ser Ser Thr Ala Pro Glu Pro Ser
        435                 440                 445

Gln Ser Ala Ser Thr Pro Ser Glu Tyr Pro Gln Pro Ser Thr Ala Glu
    450                 455                 460

Pro Thr Ala Ser Ser Ser Ser Tyr Pro Lys Ser Ser Phe Ala Ser Thr
465                 470                 475                 480

Asp Ser Pro Val Pro Thr Asp Tyr Pro Val Pro Ser Ser Asp Glu Pro
                485                 490                 495

Thr Val Pro Ser Ala Thr Tyr Ser Glu Ser Ser Pro Val Pro Thr Asp
            500                 505                 510

Tyr Pro Val Pro Ser Ser Asp Glu Pro Thr Val Pro Ser Ala Thr Tyr
        515                 520                 525

Ser Glu Ser Leu Pro Ser Ala Ser Ala Pro Ser Glu Tyr Pro Thr Gly
    530                 535                 540

Thr Ala Ser Val Asp Pro Thr Asp Val Ser Ser Cys Thr Pro Pro Pro
545                 550                 555                 560

Thr Gln Ser Cys Ile Thr Tyr Thr Thr Lys Thr Thr Ile Ala Ile Val
                565                 570                 575

Val Thr Ala Pro Glu Ser Tyr Lys Glu Ala Ile Gln Thr Glu Ser Ala
            580                 585                 590

Glu Asp Glu Thr Glu Pro Ala Ala Tyr Pro Thr Glu Pro Ala Gly Tyr
        595                 600                 605

Pro Thr Asn Asp Lys Tyr Gly Leu Glu Gln Lys Leu Ile Ser Glu Glu
    610                 615                 620

Asp Leu Asn Ser Ala Val Asp His His His His His His
```

```
625                 630                 635


<210> SEQ ID NO 3
<211> LENGTH: 652
<212> TYPE: PRT
<213> ORGANISM: Aspergillus fumigatus

<400> SEQUENCE: 3

Met Ala Pro Ser Ser Leu Leu Leu Ser Val Gly Ser Leu Ile Thr Ser
1               5                   10                  15

Ser Leu Val Ser Ala Thr Ala Leu Glu Ala Arg Gln Ser Gln Thr Tyr
            20                  25                  30

Gln Leu Ala Glu Ser Trp Gln Gly Glu Ser Phe Ile Asn Asp Trp Asn
        35                  40                  45

Phe Phe Asp Gly Ala Asp Pro Thr Asn Gly Tyr Val Thr Tyr Val Asn
    50                  55                  60

Gln Ser Phe Ala Lys Gln Ser Gly Leu Val Lys Val Thr Glu Ser Gly
65                  70                  75                  80

Ser Phe Tyr Met Gly Val Asp Tyr Glu Ser Thr Leu Asn Pro Asn Gly
                85                  90                  95

Ala Gly Arg Glu Ser Val Arg Ile Glu Ser Lys Asn Tyr Tyr Thr Glu
            100                 105                 110

Gly Leu Tyr Val Ile Asp Ile Glu His Met Pro Gly Ser Ile Cys Gly
        115                 120                 125

Thr Trp Pro Ala Phe Trp Ser Val Gly Lys Asn Trp Pro Asn Asp Gly
    130                 135                 140

Glu Ile Asp Ile Ile Glu Gly Val Asn Leu Gln Lys Ala Asn Lys Ile
145                 150                 155                 160

Val Leu His Thr Ser Gly Ser Cys Asp Val Ser Gly Ser Asn Asp Met
                165                 170                 175

Thr Gly Thr Leu Ser Ser Ser Glu Cys Gly Glu Ala Ser Gly Thr Val
            180                 185                 190

Gly Cys Val Val Lys Gly Thr Asn Gly Ser Ser Gly Asp Pro Phe Asn
        195                 200                 205

Glu Ser Gly Gly Gly Val Tyr Ala Met Glu Trp Thr Asp Thr Phe Ile
    210                 215                 220

Lys Ile Trp Phe Phe Pro Arg Ser Gln Ile Pro Ala Ser Leu Ala Ser
225                 230                 235                 240

Gly Asn Pro Asp Thr Ser Ser Phe Gly Thr Pro Met Ala His Leu Gln
                245                 250                 255

Gly Ser Cys Asp Phe Ala Glu Arg Phe Lys Ala Gln Lys Leu Ile Ile
            260                 265                 270

Asp Thr Thr Phe Cys Gly Asp Trp Ala Gly Asn Val Phe Ala Glu Ser
        275                 280                 285

Thr Cys Pro Met Ser Asp Pro Ser Ser Pro Met Gln Ser Cys Val Asn
    290                 295                 300

Tyr Val Ala Gln Asn Pro Ala Ala Phe Lys Glu Ala Tyr Trp Glu Ile
305                 310                 315                 320

Asn Ser Ile Lys Ile Tyr Gln Tyr Gly Val Ser Ala Ala Ser Ser Ala
                325                 330                 335

Ala Val Ser Gln Ala Thr Ala Ser Lys Val Glu Gly Thr Arg Val Ser
            340                 345                 350

Ala Gln Ala Ala Asn Thr Ala Thr Pro Thr Val Pro Ala Pro Val Glu
        355                 360                 365
```

-continued

```
Thr Thr Thr Val Pro Gln Pro Ala Gln Thr Asn Thr Val Ala Thr Ser
    370                 375                 380

Ala Ala Asp His Ala Thr Pro Ser Ser Ala Glu Thr Thr Thr Val Pro
385                 390                 395                 400

Ala Ala Thr Gly Ala Pro Ser Val Ser Ala Thr Glu Gly Gly Asp Ser
                405                 410                 415

Glu Leu Glu Ser Thr Ser Thr Val Tyr Val Thr Ser Thr Thr Thr Ile
            420                 425                 430

Cys Pro Val Ala Glu Ser Ser Ser Ala Ala Ala Ala Gly Gly Lys Glu
        435                 440                 445

Asp Ala Pro Ser Asn Gly Thr Ser Gly Ala Glu Val Ala Ala Thr Ser
    450                 455                 460

Val Ala Ala Ala Ala Pro Ala Ala Ala Thr Ser Gly His Pro Gly Ala
465                 470                 475                 480

Asp Ala Ile Ala Asn Ser Ala Ala Ala Thr Ser Thr Asp Ala Gln Ser
                485                 490                 495

Glu Ser Ala Thr Ser Arg Leu Thr Ala Gly Ala Leu Ser Glu Ile Pro
            500                 505                 510

Thr Ala Pro Pro Glu Pro Val Ser Gln Ala Val Ser Thr Gly Ser Phe
        515                 520                 525

Asp Asp Ser Asp Thr Ala Gln Gly Asp Ser Glu Glu Gln Gly Ser Ile
    530                 535                 540

Ala Ser Ala Ser Val Ala Pro Ser Thr Ile Pro Val Pro Ala Ser Ser
545                 550                 555                 560

Ser Ala Ala Ala Leu Gly Gly Ser Ser Ile Ala Ser Ser Phe Ala Ser
                565                 570                 575

Ser Arg Leu Ile Pro Arg Pro Thr Gly Ser Ser Thr Ala Ala Ser Ala
            580                 585                 590

Thr Ala Ile Ala Thr Trp Ser Pro Thr Ala Gly Glu Ser Ala Ser Gly
        595                 600                 605

Thr Ala Lys Glu Ser Ala Thr Leu Thr Thr Pro Ser Glu Val Phe Phe
    610                 615                 620

Thr Pro Gly Leu Ser Asn Gly Ala Asn Arg Met Ser Val Gly Leu Ser
625                 630                 635                 640

Gly Leu Ile Gly Val Met Phe Ile Ala Ala Leu Ala
                645                 650


<210> SEQ ID NO 4
<211> LENGTH: 13
<212> TYPE: PRT
<213> ORGANISM: Blastomyces dermatitidis

<400> SEQUENCE: 4

Ala Phe Phe Asp Gly Pro Asp Pro Ser Asn Ala Tyr Val
1               5                   10


<210> SEQ ID NO 5
<211> LENGTH: 13
<212> TYPE: PRT
<213> ORGANISM: Blastomyces dermatitidis

<400> SEQUENCE: 5

Val Leu Phe Ala Ala Ser Ser Ala Leu Ala Ala Pro Val
1               5                   10


<210> SEQ ID NO 6
<211> LENGTH: 13
```

<212> TYPE: PRT
<213> ORGANISM: Blastomyces dermatitidis

<400> SEQUENCE: 6

Ala Thr Tyr Ser Glu Ser Leu Pro Ser Ala Ser Ala Pro
1 5 10

<210> SEQ ID NO 7
<211> LENGTH: 13
<212> TYPE: PRT
<213> ORGANISM: Blastomyces dermatitidis

<400> SEQUENCE: 7

Ser Glu Tyr Pro Thr Gly Thr Ala Ser Val Asp Pro Thr
1 5 10

<210> SEQ ID NO 8
<211> LENGTH: 13
<212> TYPE: PRT
<213> ORGANISM: Blastomyces dermatitidis

<400> SEQUENCE: 8

Ser Glu Tyr Pro Gln Pro Ser Thr Ala Glu Pro Thr Ala
1 5 10

<210> SEQ ID NO 9
<211> LENGTH: 46
<212> TYPE: DNA
<213> ORGANISM: Artificial Sequence
<220> FEATURE:
<223> OTHER INFORMATION: synthetic

<400> SEQUENCE: 9
ggctcgagaa aagagaggct gaagctaggg ctaccaagct cgcgtt 46

<210> SEQ ID NO 10
<211> LENGTH: 37
<212> TYPE: DNA
<213> ORGANISM: Artificial Sequence
<220> FEATURE:
<223> OTHER INFORMATION: synthetic

<400> SEQUENCE: 10
gtttctagac cgtacttgtc atttgtgggg tatcccg 37

<210> SEQ ID NO 11
<211> LENGTH: 548
<212> TYPE: PRT
<213> ORGANISM: Artificial Sequence
<220> FEATURE:
<223> OTHER INFORMATION: synthetic

<400> SEQUENCE: 11

Arg Ala Thr Lys Leu Ala Leu Leu Ala Ala Leu Ala Lys Leu Ser Thr
1 5 10 15

Gly Ala Tyr Val Leu Gln Asp Asp Tyr Gln Pro Ser Asn Phe Phe Asp
20 25 30

Asp Phe Ala Phe Phe Asp Gly Pro Asp Pro Ser Asn Ala Tyr Val Thr
35 40 45

Tyr Val Asp Lys Ser Lys Ala Leu Arg Asp Gly Leu Ala Ser Asn Asn
50 55 60

Asn Asp Phe Val Tyr Leu Gly Val Asp His Gln Asn Val Ala Arg Gly
65 70 75 80

-continued

```
Arg Gly Arg Glu Ser Val Arg Leu Glu Thr Lys Lys Ser Tyr Lys His
                85                  90                  95

Gly Leu Ile Val Ala Asp Ile Ser His Met Pro Gly Asn Ile Cys Gly
            100                 105                 110

Thr Trp Pro Ala Phe Trp Ala Thr Gly Ala Thr Trp Pro Asp Asp Gly
        115                 120                 125

Glu Phe Asp Ile Ile Glu Gly Val Asn Lys Gln Asn Lys Asn Val Val
    130                 135                 140

Ala Leu His Thr Thr Ala Gly Cys Lys Val Glu Asp Asn Asn Lys Tyr
145                 150                 155                 160

Ser Gly Ile Leu Val Thr Lys Asp Cys Asp Val Tyr Ser Pro Asn Gln
                165                 170                 175

Pro Ser Asn Gln Gly Cys Leu Phe Arg Ala Pro Ser Ala Thr Ser Tyr
            180                 185                 190

Gly Thr Ala Phe Asn Ser Ile Gly Gly Gly Val Tyr Ala Thr Glu Trp
        195                 200                 205

Thr Ser Asp Ser Ile Ser Val Trp Phe Phe Pro Arg Tyr Gln Ile Pro
    210                 215                 220

Ser Asn Ile Asn Asp Glu Asn Pro Asp Pro Ser Thr Trp Pro Arg Pro
225                 230                 235                 240

Ile Ala His Phe Thr Gly Cys Glu Phe Asp Lys Phe Phe Gln Glu Gln
                245                 250                 255

Arg Ile Ile Phe Asn Thr Ala Phe Cys Gly Asp Trp Ala Lys Ala Thr
            260                 265                 270

Trp Asn Glu Asn Gly Cys Ala Ala Gly Gly Arg Thr Cys Glu Asp Tyr
        275                 280                 285

Val Lys Asn Asn Pro Trp Ala Phe Ser Glu Ala Phe Trp Ser Ile Asn
    290                 295                 300

Tyr Met Lys Val Phe Gln Asn Lys Gln Gly Asp Thr Ser Thr Ser Thr
305                 310                 315                 320

Thr Thr Ser Ser Thr Ser Ser Thr Ser Ser Ser Ser Thr Glu Ala Pro
                325                 330                 335

Thr Thr Thr Met Thr Thr Ser Ser Thr Tyr Glu Pro Ser Val Ser Ser
            340                 345                 350

Ser Thr Ala Pro Glu Pro Ser Gln Ser Ala Ser Thr Pro Ser Glu Tyr
        355                 360                 365

Pro Gln Pro Ser Thr Ala Glu Pro Thr Ala Ser Ser Ser Ser Tyr Pro
    370                 375                 380

Lys Ser Ser Phe Ala Ser Thr Asp Ser Pro Val Pro Thr Asp Tyr Pro
385                 390                 395                 400

Val Pro Ser Ser Asp Glu Pro Thr Val Pro Ser Ala Thr Tyr Ser Glu
                405                 410                 415

Ser Ser Pro Val Pro Thr Asp Tyr Pro Val Pro Ser Ser Asp Glu Pro
            420                 425                 430

Thr Val Pro Ser Ala Thr Tyr Ser Glu Ser Leu Pro Ser Ala Ser Ala
        435                 440                 445

Pro Ser Glu Tyr Pro Thr Gly Thr Ala Ser Val Asp Pro Thr Asp Val
    450                 455                 460

Ser Ser Cys Thr Pro Pro Pro Thr Gln Ser Cys Ile Thr Tyr Thr Thr
465                 470                 475                 480

Lys Thr Thr Ile Ala Ile Val Val Thr Ala Pro Glu Ser Tyr Lys Glu
                485                 490                 495

Ala Ile Gln Thr Glu Ser Ala Glu Asp Glu Thr Glu Pro Ala Ala Tyr
```

```
            500                 505                 510

Pro Thr Glu Pro Ala Gly Tyr Pro Thr Asn Asp Lys Tyr Gly Leu Glu
        515                 520                 525

Gln Lys Leu Ile Ser Glu Glu Asp Leu Asn Ser Ala Val Asp His His
    530                 535                 540

His His His His
545


<210> SEQ ID NO 12
<211> LENGTH: 356
<212> TYPE: PRT
<213> ORGANISM: Aspergillus fumigatus

<400> SEQUENCE: 12

Met Tyr Ile Arg Ser Thr Leu Pro Ile Leu Gly Phe Ser Ala Thr Gly
1               5                   10                  15

Met Ala Ala Tyr Val Leu Glu Asp Asp Tyr Gly Thr Ser Thr Ser Phe
            20                  25                  30

Phe Asp Lys Phe Ser Phe Phe Thr Asp Pro Asp Pro Thr Gly Gly Phe
        35                  40                  45

Val Ser Tyr Val Asp Arg Asn Thr Ala Gln Asp Thr Gly Leu Ile Phe
    50                  55                  60

Ala Asn Gly Ala Val Tyr Met Gly Val Asp His Thr Asn Val Ala Gly
65                  70                  75                  80

Ser Ser Gly Arg Gln Ser Val Arg Leu Thr Ser Thr Lys Ser Tyr Thr
                85                  90                  95

His Gly Leu Ile Ile Leu Asp Leu Glu His Met Pro Gly Gly Ile Cys
            100                 105                 110

Gly Thr Trp Pro Ala Phe Trp Met Leu Gly Pro Asp Trp Pro Ser His
        115                 120                 125

Gly Glu Ile Asp Ile Ile Glu Gly Val Asn Thr Gln Pro Val Asn Gln
    130                 135                 140

Met Thr Leu His Ser Thr Asp Gly Cys Ser Ile Ala Asn Gly Gly Phe
145                 150                 155                 160

Thr Gly Thr Pro Thr Asp Ile Arg Ala Gly Thr Pro Asn Pro Thr Asn
                165                 170                 175

Trp Gly Pro Pro Leu Ala Lys Phe Ala Pro Gly Ser Cys Ser Phe Asp
            180                 185                 190

Ala His Phe Ser Glu Met Gln Ile Val Phe Asp Thr Thr Phe Cys Gly
        195                 200                 205

Gly Trp Ala Gly Ser Val Trp Gly Ser Gly Ser Cys Ala Ser Leu Leu
    210                 215                 220

Thr Ser Asn Cys Tyr Asp Tyr Ala Pro Ser Gln Asp Thr Asn Ala Gly
225                 230                 235                 240

Cys Gly Ile Ala Ala Thr Ser Ser Arg Thr Tyr Gly Thr Gly Phe Asn
                245                 250                 255

Asn Ala Gly Gly Gly Ile Tyr Ala Thr Glu Trp Thr Ser Ala Gly Ile
            260                 265                 270

Ser Ile Trp Phe Phe Pro Arg Gly Ser Thr Val Ala Pro Ser Cys Gln
        275                 280                 285

Asp Phe Val Ala Asn Asn Pro Ser Ala Phe Arg Glu Ala Tyr Trp Leu
    290                 295                 300

Ile Glu Ser Leu Lys Val Tyr Gln Asp Ala Pro Gly Glu Ser Asn Asn
305                 310                 315                 320
```

-continued

```
Met Arg Met Asn Ala Thr Ser His Leu Asn Val Gln Leu Pro Arg Lys
                325                 330                 335

Gly Gly Arg Arg Ser Pro Gly Leu His Gly Arg Gly Phe Leu Glu Gly
            340                 345                 350

Thr Gly Lys Trp
        355


<210> SEQ ID NO 13
<211> LENGTH: 311
<212> TYPE: PRT
<213> ORGANISM: Pseudogymnoascus destructans

<400> SEQUENCE: 13

Met Pro Ser Leu Gln Thr Leu Ile Pro Ala Ala Ala Ile Ala Trp Leu
1               5                   10                  15

Val Gly Thr Ala Ser Ala Ala Tyr Thr Leu Gln Asp Val Tyr Asp Ser
            20                  25                  30

Thr Asn Phe Phe Asp Gly Phe Asn Phe His Asp Gly Pro Asp Pro Thr
        35                  40                  45

Asn Gly Phe Val Asp Tyr Ala Asn Ala Glu Thr Ala Asn Asn Ala Gly
    50                  55                  60

Leu Ala Gly Leu Ser Gln Asp Gly Val Tyr Met Gly Val Asp His Thr
65                  70                  75                  80

Thr Met Ser Pro Pro Asn Gly Arg Ala Ser Val Arg Val Glu Ser Gln
                85                  90                  95

Lys Gln Tyr Thr Leu Gly Leu Phe Ile Ala Asp Ile Lys His Met Pro
            100                 105                 110

Gly Ala Glu Cys Gly Ser Trp Pro Ala Phe Trp Thr Tyr Gly Pro Asp
        115                 120                 125

Trp Pro Asn Ala Gly Glu Ile Asp Ile Met Glu Gly Val Asn Thr Gln
    130                 135                 140

Leu Thr Asn Asp Val Thr Leu His Thr Ser Gly Ser Cys Ser Met Asn
145                 150                 155                 160

Asn Pro Asn Ser Gln Leu Gly Ser Val Leu Ser Asn Ala Asp Cys Ser
                165                 170                 175

Gly Thr Arg Gly Cys Gly Gln Ala Thr Ile Asp Pro Ser Asn Tyr Gly
            180                 185                 190

Thr Gly Phe Asn Thr Ile Gly Gly Gly Val Tyr Ala Met Glu Trp Thr
        195                 200                 205

Asn Glu Val Ile Ala Val Tyr Phe Phe Pro Arg Tyr Ala Ile Pro Asp
    210                 215                 220

Asp Ile Asn Ser Gly Asn Pro Asp Pro Ser Thr Trp Gly Thr Pro Leu
225                 230                 235                 240

Thr Asn Phe Val Gly Asp Ser Cys Asn Ile Gly Ser His Phe Lys Asn
                245                 250                 255

His Tyr Ile Val Phe Asp Thr Thr Phe Cys Gly Asp Trp Ala Gly Gly
            260                 265                 270

Val Trp Gly Asp Gln Cys Gly Ala Arg Ala Ala Thr Cys Glu Asp Phe
        275                 280                 285

Val Ser Gln Asn Pro Ala Ala Tyr Glu Glu Ser Tyr Trp Leu Val Asn
    290                 295                 300

Ser Val Lys Val Tyr Thr Asn
305                 310


<210> SEQ ID NO 14
```

```
<211> LENGTH: 495
<212> TYPE: PRT
<213> ORGANISM: Coccidioides immitis

<400> SEQUENCE: 14

Met Arg Ala Ala Lys Val Thr Leu Leu Ala Ala Leu Ala Gln Leu Ala
1               5                   10                  15

Ala Ala Ser Tyr Glu Leu Met Asp Asp Tyr Asn Pro Ser Asn Phe Phe
            20                  25                  30

Asp Lys Phe Glu Phe Phe Ser Gly Arg Asp Pro Ser Asn Gly Tyr Val
        35                  40                  45

Ala Tyr Gln Gly Lys Glu Ala Ala Leu Ser Ser Asn Leu Ala Gln Lys
    50                  55                  60

Leu Glu Asn Ser Ile Arg Ile Gly Ser Asp Ser Thr Asp Ile Ala Thr
65                  70                  75                  80

Gly Pro Gly Arg Arg Ser Val Arg Leu Glu Thr Lys Ala Arg Tyr Lys
                85                  90                  95

His Gly Leu Ile Val Ala Asp Ile Lys His Met Pro Gly Ser Ile Cys
            100                 105                 110

Gly Ile Trp Pro Ala Phe Trp Thr Val Gly Ser Arg Trp Pro Glu His
        115                 120                 125

Gly Glu Met Asp Ile Ile Glu Gly Val Asn Arg Gln Ser Ile Asn Lys
    130                 135                 140

Met Ala Leu His Thr Thr Ala Gly Cys Lys Ile Asn Ser Asn Gly Asp
145                 150                 155                 160

Phe Thr Gly Val Val Glu Thr Pro Asp Cys Asp Val Asn Ser Pro Asn
                165                 170                 175

Gln Ala Pro Asn Gln Gly Cys Leu Phe Thr Ser Ser Gln Gly Asn Ser
            180                 185                 190

Tyr Gly Thr Asn Phe Asn Asn Arg Asn Gly Gly Val Tyr Ala Met Glu
        195                 200                 205

Trp Thr Ser Asp Glu Ile Thr Val Trp Phe Phe Pro Arg Gly Asn Ile
    210                 215                 220

Pro Asp Asp Val Asn Ser Gln Asn Pro Asp Pro Ser Lys Trp Gly Lys
225                 230                 235                 240

Pro Ser Ala Arg Phe Ser Gly Asp Cys Asp Leu Asp Arg Phe Val Gln
                245                 250                 255

Asp Gln Arg Ile Ile Phe Asn Thr Ala Phe Cys Gly Asp Trp Ala Lys
            260                 265                 270

Gly Leu Trp Asn Ser Asp Ser Val Cys Arg Ala Lys Gly Pro Ser Cys
        275                 280                 285

Glu Asp Tyr Val Lys Asn Asn Pro Lys Asp Phe Ala Glu Ala Tyr Trp
    290                 295                 300

Glu Ile Tyr Gly Met Lys Val Tyr Ser Lys Gly Gln Gly Gln Lys Ile
305                 310                 315                 320

Ser Ser Ala Ala Thr Ser Pro Thr Gln Ala Ser Thr Thr Gln Val Ser
                325                 330                 335

Thr Thr Gln Ile Ser Ser Ala Gln Ser Ala Ser Ala Ser Ala Ser Val
            340                 345                 350

Ser Asp Gly Pro Asp Thr Ser Ser Asn Thr Pro Pro Ser Ala Thr Glu
        355                 360                 365

Ser Gly Asn Ala Ser Ser Ile Glu Ser Arg Ser Thr Asp Val Glu Pro
    370                 375                 380

Thr Lys Thr Pro Thr Gly Thr Asp Gly Gly Ala Ser Leu Thr Asn Ala
```

-continued

```
385                 390                 395                 400

Pro Cys Asn Gly Pro Asn Cys Pro Ser Gln Ser Pro Thr Thr Ser Gly
                405                 410                 415

Gly Val Ser Pro Thr Asp Lys Ser Glu Tyr Pro Ala Asn Pro Gly Thr
            420                 425                 430

Thr Gly Gly Ser Pro Leu Pro Thr Asn Lys Pro Glu Ile Pro Ser Ser
        435                 440                 445

Cys Thr Pro Arg Thr Thr Cys Val Thr Tyr Thr Arg Ile Glu Thr Val
    450                 455                 460

Thr Tyr Ile Asn Lys Asn Pro Ala Pro Phe Gln Thr Gly Val Gln Ser
465                 470                 475                 480

Pro Thr Lys Ala Ser Gly Asp Asp Glu Ser Ile Ile Pro Ile Arg
                485                 490                 495


<210> SEQ ID NO 15
<211> LENGTH: 495
<212> TYPE: PRT
<213> ORGANISM: Coccidioides posadasii

<400> SEQUENCE: 15

Met Arg Ala Ala Lys Val Thr Leu Leu Ala Ala Leu Ala Gln Leu Ala
1               5                   10                  15

Ala Ala Ser Tyr Glu Leu Met Asp Asp Tyr Asn Pro Ser Asn Phe Phe
            20                  25                  30

Asp Lys Phe Glu Phe Phe Ser Gly Arg Asp Pro Ser Asn Gly Tyr Val
        35                  40                  45

Ala Tyr Gln Gly Lys Glu Ala Ala Leu Ser Ser Asn Leu Ala Gln Lys
    50                  55                  60

Leu Glu Asn Ser Ile Arg Ile Gly Ser Asp Ser Thr Asp Ile Ala Thr
65                  70                  75                  80

Gly Ser Gly Arg Arg Ser Val Arg Leu Glu Thr Lys Ala Arg Tyr Lys
                85                  90                  95

His Gly Leu Ile Val Ala Asp Ile Lys His Met Pro Gly Ser Ile Cys
            100                 105                 110

Gly Val Trp Pro Ala Phe Trp Thr Val Gly Ser Arg Trp Pro Glu His
        115                 120                 125

Gly Glu Met Asp Ile Ile Glu Gly Val Asn Arg Gln Ser Ile Asn Lys
    130                 135                 140

Met Ala Leu His Thr Thr Ala Gly Cys Lys Ile Asn Ser Asn Gly Asp
145                 150                 155                 160

Phe Thr Gly Val Val Glu Thr Pro Asp Cys Asp Val Asn Ser Pro Asn
                165                 170                 175

Gln Ala Pro Asn Gln Gly Cys Leu Phe Thr Ser Ser Gln Gly Asn Ser
            180                 185                 190

Tyr Gly Thr Asn Phe Asn Asn Arg Asn Gly Gly Val Tyr Ala Met Glu
        195                 200                 205

Trp Thr Ser Asp Glu Ile Thr Val Trp Phe Phe Pro Arg Gly Asn Ile
    210                 215                 220

Pro Asp Asp Val Asn Ser Gln Asn Pro Asp Pro Ser Lys Trp Gly Lys
225                 230                 235                 240

Pro Ser Ala Arg Phe Ser Gly Asp Cys Asp Leu Asp Arg Phe Val Gln
                245                 250                 255

Asp Gln Arg Ile Ile Phe Asn Thr Ala Phe Cys Gly Asp Trp Ala Lys
            260                 265                 270
```

```
Gly Leu Trp Asn Ser Asp Ser Val Cys Arg Ala Lys Gly Pro Ser Cys
        275                 280                 285

Glu Asp Tyr Val Lys Asn Asn Pro Lys Asp Phe Ala Glu Ala Tyr Trp
    290                 295                 300

Glu Ile Tyr Gly Met Lys Val Tyr Ser Lys Gly Gln Gly Gln Lys Ile
305                 310                 315                 320

Ser Ser Ala Ala Thr Ser Pro Thr Gln Ala Ser Thr Thr Gln Val Ser
                325                 330                 335

Thr Thr Gln Ile Ser Ser Ala Gln Ser Ala Ser Ala Ser Ala Ser Val
            340                 345                 350

Ser Asp Gly Pro Asp Thr Ser Ser Asn Thr Pro Pro Ser Ala Thr Gly
        355                 360                 365

Ser Gly Asn Ala Ser Ser Ile Glu Ser Arg Ser Thr Asp Ala Glu Pro
    370                 375                 380

Thr Lys Ala Pro Thr Gly Thr Asp Gly Gly Ala Ser Pro Thr Asn Ala
385                 390                 395                 400

Pro Cys Asn Gly Pro Asn Cys Pro Ser Gln Ser Pro Thr Thr Ser Gly
                405                 410                 415

Gly Val Ser Pro Thr Asp Lys Ser Glu Tyr Pro Ala Asn Pro Gly Thr
            420                 425                 430

Thr Asp Gly Ser Pro Leu Pro Thr Asn Lys Pro Glu Ile Pro Thr Ser
        435                 440                 445

Cys Thr Pro Arg Thr Thr Cys Val Thr Tyr Thr Arg Ile Glu Thr Val
    450                 455                 460

Thr Tyr Ile Asn Lys Asn Pro Ala Pro Phe Gln Thr Gly Val Gln Ser
465                 470                 475                 480

Pro Thr Lys Ala Ser Gly Asp Asp Glu Ser Ile Ile Pro Ile Arg
                485                 490                 495


<210> SEQ ID NO 16
<211> LENGTH: 490
<212> TYPE: PRT
<213> ORGANISM: Histoplasma capsulatum

<400> SEQUENCE: 16

Met Arg Thr Thr Lys Leu Thr Leu Leu Ala Thr Leu Ala Lys Leu Ser
1               5                   10                  15

Ala Gly Thr Tyr Val Leu Lys Asp Asp Tyr Gln Pro Ser Asn Phe Phe
            20                  25                  30

Asp Asn Phe Asn Phe Phe Asn Gly Pro Asp Pro Ser Asn Gly Tyr Val
        35                  40                  45

Thr Tyr Leu Asp Lys Ser Asn Ala Val Asn Asn Gly Leu Ala Ser Asn
    50                  55                  60

Glu Asn Asp Phe Val Tyr Leu Gly Val Asp Ser Lys Asn Val Ala Lys
65                  70                  75                  80

Gly Leu Gly Arg Glu Ser Val Arg Leu Glu Thr Lys Lys Thr Tyr Lys
                85                  90                  95

His Gly Leu Ile Val Val Asp Ile Ser His Met Pro Gly Gly Ile Cys
            100                 105                 110

Gly Thr Trp Pro Ala Leu Trp Ser Thr Gly Ala Thr Trp Pro Glu Asp
        115                 120                 125

Gly Glu Leu Asp Ile Ile Glu Gly Val Asn Ser Gln Thr Lys Asn Val
    130                 135                 140

Val Ala Leu His Thr Thr Ala Gly Cys Lys Val Glu Asp Asn Ser Asn
145                 150                 155                 160
```

-continued

```
Tyr Ser Gly Glu Leu Val Thr Lys Asp Cys Asp Ile Asn Ser Pro Thr
                165                 170                 175

Gln Pro Gly Asn Gln Gly Cys Leu Phe Arg Ala Pro Ser Ser Met Ser
            180                 185                 190

Tyr Gly Asn Ser Phe Asn Ser Ile Gly Gly Gly Ile Tyr Ala Ala Glu
        195                 200                 205

Trp Thr Thr Asp Ser Ile Ser Val Trp Phe Phe Pro Arg Tyr Arg Ile
    210                 215                 220

Pro Ser Asp Ile Asn Ser Glu His Pro Asp Pro Ser Ser Trp Ala Arg
225                 230                 235                 240

Pro Ile Ala His Phe Thr Gly Cys Glu Phe Asp Lys Phe Phe Gln Glu
                245                 250                 255

Gln Arg Ile Ile Ile Asn Thr Ala Phe Cys Gly Asp Trp Ala Lys Asn
            260                 265                 270

Thr Trp Ser Gln Asp Ala Glu Cys Ala Ala Lys Ala Asp Ser Cys Glu
        275                 280                 285

Ala Tyr Val Gln Asn Asn Pro Ser Ala Phe Ser Glu Ala Tyr Trp Ser
    290                 295                 300

Ile Asn Tyr Met Lys Val Phe Gln Asp Glu Val Val Asp Tyr Pro Gly
305                 310                 315                 320

Asp Ser Thr Thr Thr Thr Thr Ser Thr Thr Ala Ser Gln Thr Asp Ser
                325                 330                 335

Thr Glu Pro Thr Thr Thr Thr Thr Thr Thr Ser Thr Thr Thr Thr Thr
            340                 345                 350

Ser Thr Gln Pro Ala Asp Thr Gly Ala Thr Asn Thr Asp Ser Ser Pro
        355                 360                 365

Ser Ala Ser Ala Thr Asn Glu Tyr Pro Thr Gly Ser Ala Ser Val Glu
    370                 375                 380

Pro Thr Asp Ile Ala Ser Cys Thr Pro Pro Pro Thr Glu Ser Cys Ile
385                 390                 395                 400

Thr Tyr Thr Thr Lys Thr Thr Ile Ala Val Val Val Thr Pro Thr Gly
                405                 410                 415

Tyr Asn Glu Ala Ile Ile Pro Ile Pro Thr Glu Ser Ala Glu Tyr Glu
            420                 425                 430

Thr Glu Pro Thr Glu Asn Pro Ile Glu Pro Ser Glu Tyr Pro Thr Ala
        435                 440                 445

Pro Val Gly Tyr Pro Thr Glu Pro Ile Gly Tyr Pro Thr Glu Pro Ile
    450                 455                 460

Gly Tyr Pro Thr Asn Asp Gln Asp Val Pro Leu Lys Arg Arg Gln His
465                 470                 475                 480

Ile Lys Lys His Ile Ala Gly Thr His His
                485                 490
```